United States Patent
Freeman et al.

(10) Patent No.: US 7,416,885 B2
(45) Date of Patent: Aug. 26, 2008

(54) PROLIFERATED CELL LINES AND USES THEREOF

(75) Inventors: Thomas B. Freeman, Tampa, FL (US); Pablo Caviedes, Santiago (CL); Raul Caviedes, Santiago (CL)

(73) Assignees: University of South Florida, Tampa, FL (US); University of Chile (CL)

( * ) Notice: Subject to any disclaimer, the term of this patent is extended or adjusted under 35 U.S.C. 154(b) by 744 days.

(21) Appl. No.: 10/359,854

(22) Filed: Feb. 7, 2003

(65) Prior Publication Data
US 2003/0232752 A1 Dec. 18, 2003

Related U.S. Application Data

(60) Provisional application No. 60/355,157, filed on Feb. 8, 2002.

(51) Int. Cl.
*C12N 5/00* (2006.01)
(52) U.S. Cl. ...................................... 435/325
(58) Field of Classification Search ............ None
See application file for complete search history.

(56) References Cited

OTHER PUBLICATIONS

Hartung T. et al. ATLA 30: 407-414, 2002.*
Allen, D.D. et al. "Impaired cholinergic function in cell lines derived from the cerebral cortex of normal and trisomy 16 mice" *Eur. J. Neuroscience*, 2000, 12:3259-3264.
Arriagada, C. et al. "Cells of the Neuronal Cell Line CTB, Derived from the Cerebral Cortex of a Trisomy 16 Mouse, Accumulate Amyloid in Intracytoplasmic Vacuole-Like Compartments" Society for Neuroscience Meeting Abstract, Sunday, Nov. 5, 2000.
Arriagada, C. et al. "Studies of aminochrome toxicity in a mouse derived neuronal cell line: is this toxicity mediated via glutamate transmission?" *Amino Acids*, 2000, 18:363-373.
Cardenas, A.M. et al. "Immortalized Neuronal Cell Lines From the Spinal Cord of Normal and Trisomy 16 Fetal Mice, an Animal Model of Down Syndrome" Society for Neuroscience Meeting Abstract, Wednesday, Nov. 14, 2001.
Cardenas, A.M. et al. "Calcium signals in cell lines derived from the cerebral cortex of normal and trisomy 16 mice" *NeuroReport*, 1999, 10:363-369.
Caviedes, P. et al. "Calcium Fluxes, Ion Currents and Dihydropyridine Receptors in a New Immortal Cell Line from Rat Heart Muscle" *Mol. Cell. Cardiol.*, 1993, 25:829-845.
Caviedes, P. et al. "The role of altered sodium currents in action potential abnormalities of cultured dorsal root ganglion neurons from trisomy 21 (Down syndrome) human fetuses" *Brain Res.*, 1990, 510:229-236.

(Continued)

*Primary Examiner*—Christopher H. Yaen
(74) *Attorney, Agent, or Firm*—Saliwanchik, Lloyd & Saliwanchik

(57) ABSTRACT

The subject invention pertains to tumor cell lines useful for increasing the proliferation potential of any human or animal cell in culture, thereby providing immortalized or continuous cell lines and cultures. The invention also concerns proliferation factors, and compositions containing the factors, which are capable of increasing the proliferation potential of any human or other animal cell in culture. The subject invention further pertains to a method for proliferation cells in culture by contacting cells with the proliferation factors. The proliferated cells can range in plasticity and can include, for example, blast cells, fertilized ova, non-fertilized gametes, embryonic stem cells, adult stem cells, precursor or progenitor cells, and highly specialized cells. Optionally, the cells can be induced to cease proliferation. The proliferation cells of the subject invention are useful for cell therapy, cell/gene therapy, biological production of molecules, and as in vitro models for research, toxicity testing, and drug development.

10 Claims, 29 Drawing Sheets

OTHER PUBLICATIONS

Caviedes, R. et al. "Ion Channels in a Skeletal Muscle Cell Line from a Duchenne Muscular Dystrophy Patient" *Muscle & Nerve*, 1994, 17:1021-1028.

Caviedes, R. et al. "A human skeletal muscle cell line obtained from an adult donor" *Biochimica et Biophysica Acta*, 1992, 1134:247-255.

Caviedes, R. et al. "Tetrodotoxin-Sensitive Sodium Channels in a Continuously Cultured Cell Line Derived from the Adult Rat Cerebellum" *Brain Res.*, 1986, 365:259-268.

Caviedes, R. and J.B. Stanbury "Studies on a Cell Line from a Functional Rat Thyroid Tumor in Continuous Culture" *Endocrinology*, 1976, 99:549-554.

Freeman, T.B. et al. "Neural Transplantation in Parkinson's Disease" *Parkinson's Disease: Advances in Neurology*, Chapter 46, 2001, 86:435-445.

Freeman, T.B. et al. "Transplanted fetal striatum in Huntington's disease: Phenotypic development and lack of pathology" *PNAS*, Dec. 5, 2000, 97(25):13877-13882.

Freeman, T.B. et al. "Neural transplantation for the treatment of Huntington's disease" *Progress in Brain Res.*, Chapter 18, 2000, 127:405-411.

Freeman, T.B. et al. "Bilateral Fetal Nigral Transplantation into the Postcommissural Putamen in Parkinson's Disease" *Annuals of Neurology*, Sep. 1995, 38(3):379-388.

Freeman, T.B. et al. "Cross-species intracerebral grafting of embryonic swine dopaminergic neurons" *Progress in Brain Res.*, Chapter 61, 1988, 78:473-477.

Hernandez, R.A. et al. "MPP+ but not MPTP Induces Toxicity and Apoptosis in the Neuronal Dopaminergic Cell Line RCSN-3" Society for Neuroscience Meeting Abstract, Tuesday, Nov. 5, 2002.

Kin, T. et al. "Development of an Immunoprivileged Site to Prolong Islet Allograft Survival" *Cell Transplantation*, 2002, 11:547-552.

Liberona, J.L. et al. "Differences in Both Inositol 1,4,5-Trisphosphate Mass and Inositol 1,4,5-Trisphosphate Receptors Between Normal and Dystrophic Skeletal Muscle Cell Lines" *Muscle Nerve*, 1998, 21:902-909.

Lima, A.C.P. et al. "Nitrophenols Reduce the content of Intracellular β Amyloid in the CTB Neuronal Cell Line, Derived from the Trisomy 16 Mouse" Society for Neuroscience Meeting Abstract, Tuesday, Nov. 5, 2002.

Martin, G.R. "Isolation of a pluripotent cell line from early mouse embryos cultured in medium conditioned by teratocarcinoma stem cells" *Proc. Natl. Acad. Sci.*, Dec. 1981, 78(12):7634-7638.

Sanberg, P.R. et al. "Transplantation of Testis-Derived Sertoli Cells into the Mammalian Brain" *Transplantation Proceedings*, 1997, 29:1926-1928.

Segura-Aguilar, J. et al. "The Dopamine Oxidation Product Aminochrome Induces Apoptosis in the RCSN-3 Dopaminergic Cell Line" Society for Neuroscience Meeting Abstract, Tuesday, Nov. 5, 2002.

Segura-Aguilar, J.E. et al. "The Role of DT-Diaphorase in Dopaminergic Neurons" Society for Neuroscience Meeting Abstract, Monday, Nov. 12, 2001.

Tsai, R. and R. McKay "A nucleolar mechanism controlling cell proliferation in stem cells and cancer cells" *Genes & Development*, 2002, 16:2991-3003.

Willing, A.E. et al. "Sertoli cells decrease microglial response and increase engraftment of human hNT neurons in the hemiparkinsonian rat striatum" *Brain Res. Bulletin*, 1999, 48(4):441-444.

Willing, A.E. et al. "Sertoli cells enhance the survival of co-transplanted dopamine neurons" *Brain Res.*, 1999, 822:246-250.

Hurtado-Guzman, C. et al. "J. Neurotoxicity of MAO inhibitors in adult rat hypothalamic cell culture" *Neurotoxicity Res.*, 2002, 4(2):161-163.

Cardenas, A.M. et al. "Cell lines derived from hippocampal neurons of the normal and trisomy 16 mouse fetus (a model for Down syndrome) exhibit neuronal markers, cholinergic function, and functional neurotransmitter receptors" *Exp. Neurol.*, Sep. 17, 2002, 177(1):159-170.

Paris, I. et al. "Copper neurotoxicity is dependent on dopamine-mediated copper uptake and one-electron reduction of aminochrome in a rat substantia nigra neuronal cell line" *J. Neurochemistry*, 2001, 77:519-529.

Dagnino-Subiabre, A. et al. "Angiotensin receptor II is present in dopaminergic cell line of rat substantia nigra and it is down regulated by aminochrome" *Mol. Cell. Biochemistry*, 2000, 212:131-134.

Amar, A.P. et al. "Endovascular Restorative Neurosurgery: A Novel Concept for Molecular and Cellular Therapy of the Nervous System" *Neurosurgery*, 2003, 52(2):402-413.

Bergers, G. and D. Hanahan "Cell factories for fighting cancer" *Nature Biotechnology*, Jan. 2001, 19:20-21.

Couzin, J. "Select T Cells, Given Space, Shrink Tumors" *Science*, Sep. 20, 2002, 297:1973.

Dove, A. "Cell-based therapies go live" *Nature Biotechnology*, Apr. 2002, 20:339-343.

Dudley, M.E. et al. "Cancer Regression and Autoimmunity in Patients After Clonal Repopulation with Antitumor Lymphocytes" *Science*, Oct. 25, 2002, 298:850-854.

Freed, W.J. "Functional Brain Tissue Transplantation: Reversal of Lesion-Induced Rotation by Intraventricular Substantia Nigra and Adrenal Medulla Grafts, with a Note on Intracranial Retinal Grafts" *Biological Psychiatry*, 1983, 18(11):1204-1267.

Griffith, L.G. and G. Naughton "Tissue Engineering—Current Challenges and Expanding Opportunities" *Science*, Feb. 8, 2002, 295:1009-1014.

Halvorsen, T. et al. "In Vivo Glucose-Responsive Insulin Secretion from a Human Pancreatic β-Cell Line" *Diabetes*, 2000, 4:(Suppl 1):A32 (abstract).

Joki, T. et al. "Continuous release of endostatin from microencapsulated engineered cells for tumor therapy" *Nature Biotechnology*, Jan. 2001, 19:35-39.

Kaufman, D.S et al. "Hematopoietic colony-forming cells derived from human embryonic stem cells" *PNAS*, Sep. 11, 2001, 98(19):10716-10721.

Kobayashi, N. and N. Tanaka "Engineering of Human Hepatocyte Lines for Cell Therapies in Humans: Prospects and Remaining Hurdles" *Cell Transplantation*, 2002, 11:417-420.

Langer, R. "Researchers Say Human Embryonic Stem Cells Can Develop into Blood Vessels" *Stem Cell Res. News*, Apr. 1, 2002, pp. 2-3.

Lee, S-H. et al. "Efficient generation of midbrain and hindbrain neurons from mouse embryonic stem cells" *Nature Biotechnology*, Jun. 2000, 18:675-679.

Lumelsky, N. et al. "Differentiation of Embryonic Stem Cells to Insulin-Secreting Structures Similar to Pancreatic Islets" *Science*, May 18, 2001, 292:1389-1394.

Mancardi, G.L. et al. "Autologous hematopoietic stem cell transplantation suppresses Gd-enhanced MRI activity in MS" *Neurology*, 2001, 57:62-68.

Mason, D.W. et al. "The Fate of Allogeneic and Xenogeneic Neuronal Tissue Transplanted into the Third Ventricle of Rodents" *Neuroscience*, 1986, 19(3):685-694.

Menasché, P. et al. "Myoblast transplantation for heart failure" *The Lancet*, Jan. 27, 2001, 357:279-280.

Nicholas, M.K. et al. "Rejection of Fetal Neocortical Neural Transplants by H-2 Incompatible Mice" *J. Immunology*, Oct. 1, 1987, 139(7):2275-2283.

Oktay, K. et al. "Endocrine Function and Oocyte Retrieval After Autologous Transplantation of Ovarian Cortical Strips to the Forearm" *JAMA*, Sep. 26, 2001, 286(12):1490-1493.

Read, T-A. et al. "Local endostatin treatment of gliomas administered by microencapsulated producer cells" *Nature Biotechnology*, Jan. 2001, 19:29-34.

Robertson, R.P. "Successful Islet Transplantation for Patients with Diabetes—Fact or Fantasy?" *New Eng. J. Med.*, Jul. 27, 2000, 343(4):289-290.

Ryan, E.A. et al. "Clinical Outcomes and Insulin Secretion After Islet Transplantation with the Edmonton Protocol" *Diabetes*, Apr. 2001, 50:710-719.

Sarkis, R. et al. "Semiautomatic Macroencapsulation of Fresh or Cryopreserved Procine Hepatocytes Maintain Their Ability for Treatment of Acute Liver Failure" *Cell Transplantation*, 2001, 10:601-607.

Shapiro, A.M. et al. "Islet Transplantation in Seven Patients with Type I Diabetes Mellitus Using a Glucocorticoid-Free Immunosuppressive Regimen" *New Eng. J. Med.*, Jul. 27, 2000, 343(4):230-238.

Suzuki, K. et al. "Normalization of Blood Glucose After Islet Cografting With Placental Tissues in Diabetic Mice" *Cell Transplantation*, 2002, 11:455-457.

Studer, L. et al. "Transplantation of expanded mesencephalic precursors leads to recovery in parkinsonian rats" *Neuroscience*, Aug. 1998, 1(4):290-295.

Tibell, A. et al. "Survival of Macroencapsulated Allogeneic Parathyroid Tissue One Year After Transplantation in Nonimmunosuppressed Humans" *Cell Transplantation*, 2001, 10:591-599.

Warren, J. "Tolerance, pig islet cells, transplanting HIV patients, hand transplant success headline congress news coverage" *Transplant News*, Sep. 27, 2002, pp. 4-6.

Winkler, C. et al. "Intranigral Transplants of GABA-Rich Striatal Tissue Induce Behavioral Recovery in the Rat Parkinson Model and Promote the Effects Obtained by Intrastriatal Dopaminergic Transplants" *Exper. Neurology*, 1999, 155:165-186.

Winslow, R. "Two Studies Show Stem Cells' Promise In Repairing Damage From Heart Attacks" *Wall Street Journal*, Apr. 2, 2001.

"Stem cells could help rebuild the immune system, repair vocal chords" *Transplant News*, Aug. 12, 2002, pp. 5-6.

Allen, D.D. et al. "A dorsal root ganglia cell line derived from trisomy 16 fetal mice, a model for Down syndrome" *Neuroreport*, Mar. 25, 2002, 13(4):491-496.

Cardenas, A.M. et al. "Establishment and characterization of immortalized neuronal cell lines derived from the spinal cord of normal and trisomy 16 fetal mice, an animal model of Down syndrome" *J. Neurosci Res.*, Apr. 1, 2002, 68(1):46-58.

Caviedes, P. "The Cell in Culture. In vitro Models for the Study of Cell Function and Transplant Therapy" in Mechanisms of Degeneration and Protection of the Dopaminergic System, Chapter 16, Eds. J. Segura-Aguilar, FP Graham Publishing Co., Johnson City, TN, 2001.

Arriagada, C. et al. "An immortalized neuronal cell line derived from the substantia nigra of an adult rat: application to cell transplant therapy" in Parkinson's Disease, Eds E. Ronken and G. van Scharrenburg, IOS Press, Amsterdam, Netherlands, 2002.

Sepulveda, D. "Optimization of culture techniques in dopaminergic cell lines: Aplications in the isolation cell products and of cell transplant therapy" Undergraduate thesis of Chemical Engineering, Mathematical and Physical Faculty of Sciences, University of Chile, Nov. 11, 2001.

Andrews, B.A. et al. "Factors for the Optimization of the Culture of Neuronal Cell Lines for the Development of Cell Transplant Material" Cell Culture Engineering VII, Snowmass Conference Center, Poster Session II, Apr. 3-4, 2002; poster II-20.

Aguilar Hernandez, R. et al. "MPP+induces toxicity and apoptosis and enhances free radical production in the neuronal cell line RCSN-3" 3rd Forum of European Neuroscience, Paris, Jul. 13-17, 2002, FENS Abstr. vol. 1, A226.2, 2002.

Caviedes, P. and J. Segura-Aguilar "The Price of Development in Chile" *Neuroreport*, Mar. 26, 2001, 12(4):A25.

Chilmonczyk, Z. "5-HT$_{1A}$ Receptors. Their role in Anxiety and Depression. Mechanism of Activation" *Pol. J. Pharmacol.*, 2002, 54:175-183.

Kostrzewa, R.M., and J. Segura-Aguilar "Program and Abstracts of the First Int'l Meeting: Mechanisms for Neurodegenerative Disorders—Alzheimer, Amyotropic Lateral Sclerosis (ALS) and Parkinson's Disease" *Neurotoxicity Res.*, 2002, 4(2):165-182.

Martinez-Alvarado, P. et al. "Possible Role of Salsolinol Quinone Methide in the Decrease of RCSN-3 Cell Survival" *Biochem. and Biophys. Res. Comm.*, 2001, 283:1069-1076.

Paris, I. et al. "DT-Diaphorase: A Neuroprotective Enzyme of Dopaminergic Systems" *Pol. J. Pharmacol.*, 2002, 54:175-183.

Carmona, M.T. and R. Caviedes "Effects of Factors Derived From a Tumor Clonal Cell Line on DNA Synthesis of Transformed and Non Transformed Cells" *Cell Biol. Int'l Reports*, Mar. 1985, 9(3):209-219.

Aguilar Hernandez, R. et al. "MPP+but not MPTP Induces Toxicity and Apoptosis by Enhanced Free Radical Production in the Neuronal Dopaminergic Cell Line RCSN-3" Soc. Neurosci. Abstr., Nov. 2002, 485.2

Segura-Aguilar, J. et al. "DT-Diaphorase: A Neuroprotective Enzyme of Dopaminergic Neurons" 11$^{th}$ Neuropsychopharmacological Meeting, Ustron-Jaszowiec, Poland, May 26-29, 2002.

Garcia, C. et al. "Characterization of Intracellular Ca$^{2+}$Signals Induced by Glutamate and Noradrenaline in Neuronal Cell Lines From Dorsal Root Ganglion of Normal and Trisomy 16 Mouse" International Neurotoxicity Meeting on Mechanisms for Degenerative Disorders, Mar. 16-18, 2001, Pucon, Chile.

Mendoza, I. et al. "Overexpression of a Metabolic Product of the Amyloid Precursor in the CTb Neuronal Cell Line" International Neurotoxicity Meeting on Mechanisms for Degenerative Disorders, Mar. 16-18, 2001, Pucon, Chile.

Salazar, J. et al. "La Linea Celular RCSN, Derivada de la Substantia nigra de una Rata Adults, Como Modelo de Estudio Enfermedad de Parkinson" XX Congreso de la Asociacion Latinoamericana de Ciencias Fisiologicas: Sep. 5-7, 2000, Cancun, Mexico.

Saud, K. et al. "The Effect of Aminochrome, a Dopamine-Derived Endogenous Neurotoxin, on Dopamine Receptors: A Proposed Mechanism in Parkinson's Disease" Satellite Symposium "Novel Therapeutic Strategies based on G-protein Coupled Receptors" of Joint Meeting of the International Society for Neurochemistry and the American Society for Neurochemistry, Buenos Aires, Argentina, Aug. 24-25, 2001.

Allen, D. et al. "Cell lines as in vitro models for drug screening and toxicity studies" *Drug Devel. Indust. Pharm.*, 2005, 31:757-768.

Ambesi-Impiombato, F.S. et al. "Culture of hormone-dependent functional epithelial cells from rat thyroids" *PNAS*, 1980, 77:3455-3459.

Beguinot, F. et al. "Thyrotropin regulation of membrane lipid fluidity in the FRTL-5 thyroid cell line" *J. Biol. Chem.*, 1987, 262:1575-1582.

Saji, M. et al. "Regulation of thyrotropin receptor gene expression in rat FRTL-5 thyroid cells" *Endocrinology*, 1992, 130:520-533.

Saud, K. et al. "Neuronal dysfunction in Down syndrome: Contribution of neuronal models in cell culture" *J. Physiology Paris*, 2006, 99(2-3):201-210.

* cited by examiner

Control | Differentiated
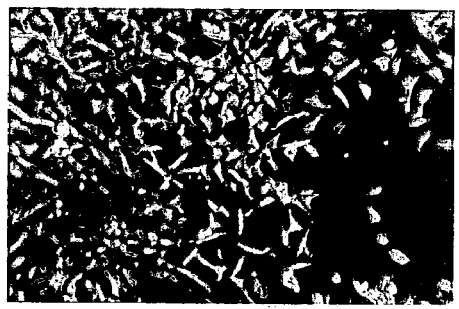 
FIG. 2A | FIG. 2B
H-E
 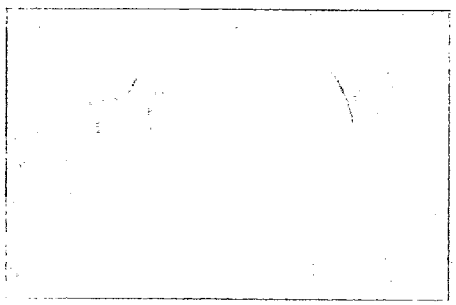
FIG. 2C | FIG. 2D
Melanin
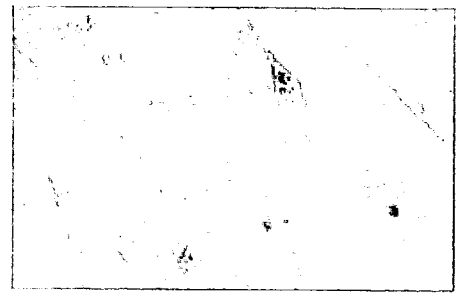 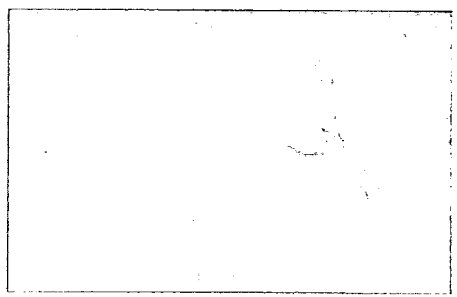
FIG. 2E | FIG. 2F NSE | Control | Differentiate

SNP

MAP-2

Neurofilament     Tetanus toxin

Non differentiated        Differentiated
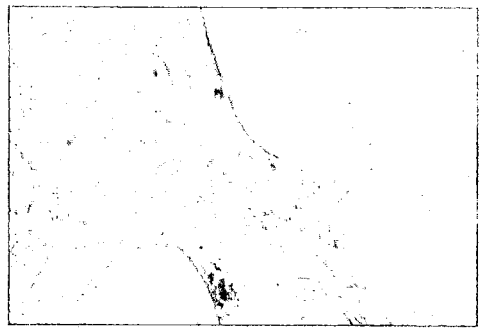    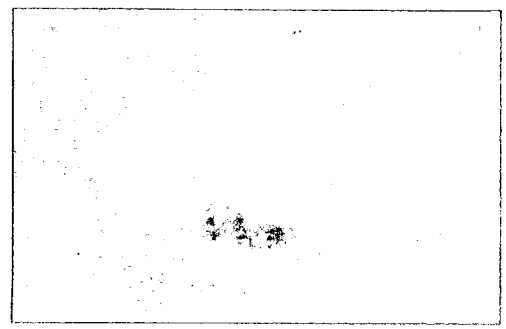
FIG. 4A            FIG. 4B
Paraformaldehyde-glyoxylate
    
FIG. 4C            FIG. 4D
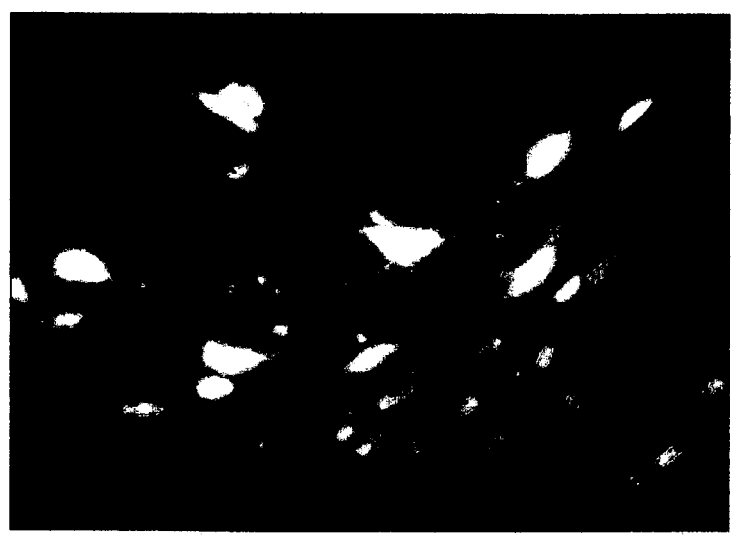
FIG. 5

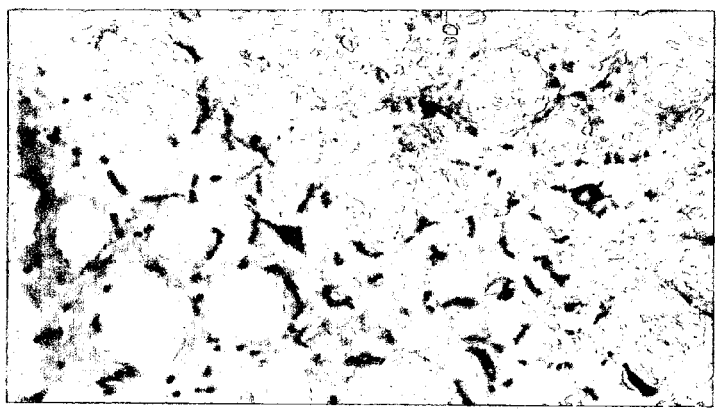
FIG. 7A — TH 10x
FIG. 7B — DOPA-DC 40x
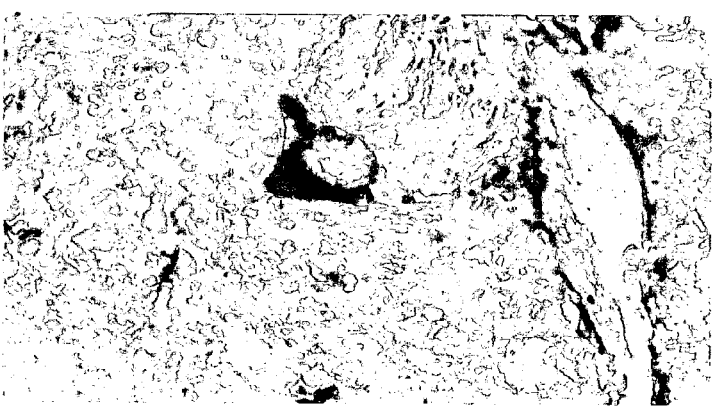
FIG. 7C — TH 40x

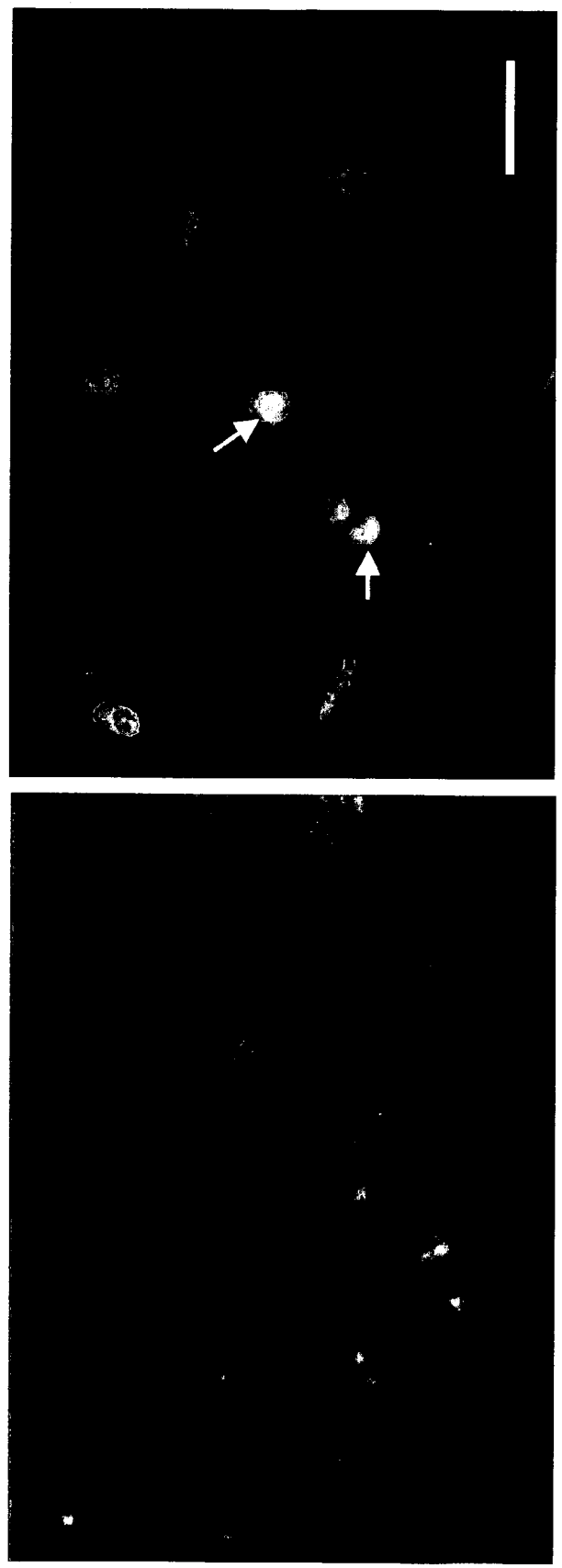

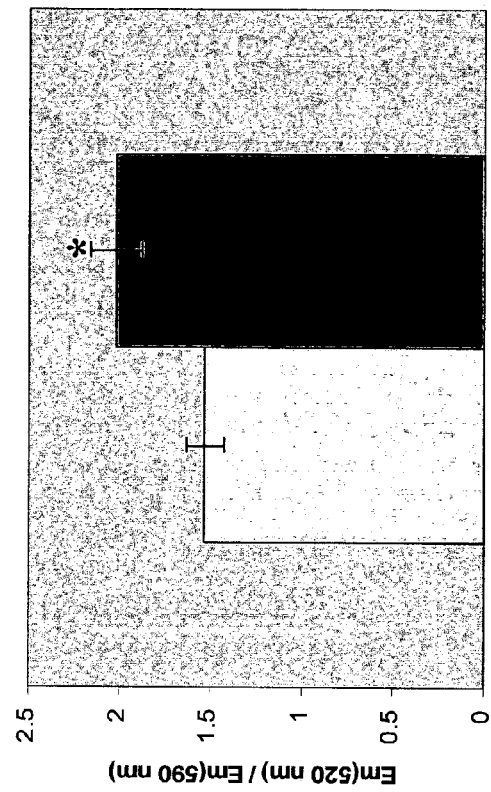
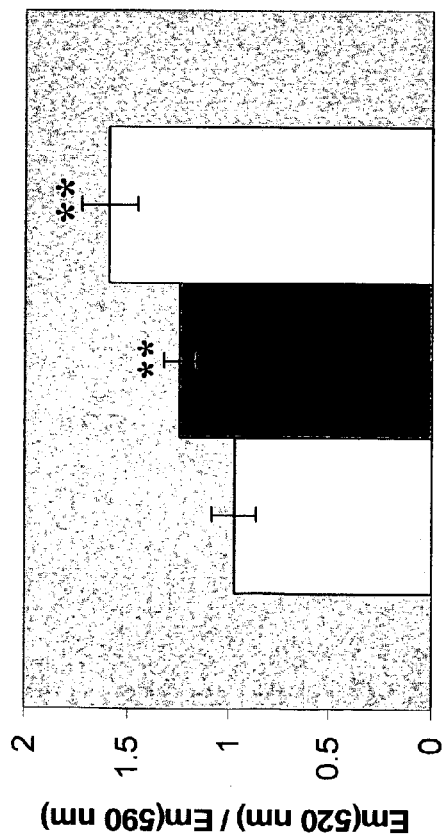
FIG. 22A
FIG. 22B

P: in proliferation; D: differentiated; GR: glucocorticoid receptor.

PROLIFERATED CELL LINES AND USES THEREOF

CROSS-REFERENCE TO RELATED APPLICATION

The present application claims the benefit of priority of U.S. Provisional Application Ser. No. 60/355,157, filed Feb. 8, 2002, which is hereby incorporated by reference herein in its entirety, including any figures, tables, nucleic acid sequences, amino acid sequences, or drawings.

BACKGROUND OF THE INVENTION

Most cells can be cultured in vitro to a limited extent using conventional cell culture technology, provided that suitable nutrients and other conditions for growth are supplied. Such cultures have been used to study genetic, physiological, and other phenomena, as well as to manufacture certain biomolecules using various fermentation techniques. In studies of mammalian cell biology, cell cultures derived from lymph nodes, muscle, connective tissue, kidney, dermis, and other tissue sources have been used, for example. However, most normal cells have a limited growth potential in culture. After a certain number of cell divisions (the Hayflick limit), they can no longer proliferate (Hayflick L., *Exp. Cell. Res.*, 1965, 37:614–636). This limited life span, termed replicative senescence, likely arose as a protective mechanism against unfettered clonal evolution and cancer in long-lived animals. Therefore, while it has long been a goal of scientists to be able to maintain all types of cells in vitro, standard culture conditions do not promote the long-term survival or proliferation of most cells.

"Immortalization" is the escape from the normal limitation on growth of a finite number of division cycles. Therefore, once immortalized, a cell line can be continuously cultured. However, immortal cell lines very rarely emerge spontaneously under usual culture conditions.

In order to increase the life span of cells in culture, published techniques have included the use of embryonic cells. The strategy of starting with embryonic cells is based on the fact that embryonic cells are relatively less differentiated than adult cells, and thus can be expected to go through several cycles of cell division before becoming terminally differentiated. It is an axiom of biology that undifferentiated cells proliferate at a greater rate than differentiated cells. It is generally believed that by the time a cell has developed the necessary intra-cellular machinery for hormone synthesis and secretion, for example, it is no longer able to divide rapidly, if at all.

Another known strategy for establishing cells in culture is to start with tumor cells, due to their greater potential for proliferation. While these types of cell lines are able to generate a large number of cells, the limited number of these types of lines, the limited number of phenotypes that they are able to generate, and their inherent tumorgenicity, make these types of cell lines less than ideal.

Normal cells have been transformed in culture by various means including the use of UV light, chemical carcinogens, and the introduction of oncogenes, which alters the genetic programming of the cell, thereby inducing the cell to proliferate indefinitely. Simian virus 40 (SV40) has been used for some time to immortalize human cells from different tissues in order to gain continuously growing cell lines (Sack, G. H. In vitro, 1981, 17:1–19). Rat granulose cells were transformed by co-transfection with the entire SV40 genome and the activated Ha-ras gene (Baum, G. et al. *Develop Biol*, 1990, 112:115–128). These cells were reported to retain at least some differentiated characteristics, i.e., they were able to synthesize steroids in response to cAMP. It has also been shown that expression of SV40 large T protein alone is sufficient to induce transformed properties in primary cells (Abcouver, S. *Bio/Technology*, 1989, 7:939–946). Other cell lines established in culture include UMR cells, derived from normal islets of neonatal rats (NG, K. W. et al., *J. Endocrinol.*, 1987, 113:8–10) and HIT cells, derived by SV40 infection of hamster islets (Santerre, R. F. et al., *PNAS*, 1981, 78:4339–4343). The insulin secretory output of these cell lines is low, however, and response to glucose is lost with passage in culture. Thus, while the proliferative status of these cell lines may prove useful for studying the decisions that occur during cell determination and differentiation, and for testing the effects of exogenous agents, these immortalization agents may affect other properties of the cell, such as the cell's ability to differentiate and express genes in a physiologically correct manner.

More recent methods of cell line immortalization that are still in the beginning stages of development involve telomeres, the ends of chromosomes composed of non-coding repeat DNA sequences. It has been suggested that the limited reproductive lifespan of normal (diploid) cells in culture may be explained by an inevitable shortening of one or more telomeres. It is known that cancer cells, germ cells, and some eucaryotic microorganisms have the ability to correct this phenomenon with the enzyme telomerase, which catalyzes telomere elongation. Normal cells modified to express telomerase are immortal in culture (Bodnar et al., *Science*, 1998, 279(5349):349–352), presumably by maintaining a constant telomere length. Furthermore, in vitro-aged fibroblasts treated with telomerase regain dermal function (Funk et al., *Exp. Cell. Res.*, 2000, 258(2):270–278).

Only a few neuronal cell types have been reported to divide in the adult brain and adult neurons do not survive well in vitro. The generation of clonal cell lines from different regions of the brain would greatly facilitate the discovery of new neurotrophic factors and their receptors, and enhance the understanding of their function. The central nervous system contains two major classes of cells known as neurons and glial cells. There are hundreds of different types of neurons and many different neurotrophic factors that influence their growth and differentiation. Depending upon the type of neuron and the region of the brain in which the neuron resides, a different neurotrophic factor or specific combination of factors affect the survival, proliferation, and differentiation of the neuron.

To date, neuropharmacological studies in the central nervous system (CNS) have been delayed by the lack of cell systems needed to investigate potentially useful neuroactive compounds. In live animals, the complexity of the brain makes it difficult to effectively measure which cellular receptors are being targeted by these compounds. Additionally, the expense involved in live animal research and the current controversies stemming from animal rights movements have made in vivo animal studies less acceptable for initial research. Primary cells from neuronal tissue are often used for CNS studies; however, long-term culture of primary neurons has not been achieved. Only a few attempts to achieve long term culture and proliferation of neuronal cells have been reported. In fact, the proliferation of neuronal cells has proven so elusive that it has become ingrained in the scientific community that neuronal cells do not proliferate in vitro. As a consequence, fresh dissections must be performed for each study in order to obtain the necessary neuronal cell types, resulting in costly research with increased variability in the experimental results.

While some neuronal tumor cell lines exist, they are few in number and are not well characterized. In general, these tumor cell lines do not mimic the biology of the primary neurons from which they were originally established. In vitro primary cultures that are more phenotypically representative of primary cells and that could generate continuous cultures of specific neuronal cell lines capable of proliferation would be invaluable.

Similar to neurons, the endocrine cells of the mammalian pancreas have been considered to be post-mitotic, i.e., terminal, essentially non-dividing cells. Recent work has shown that the cells of the mammalian pancreas (including those of humans) are capable of survival in culture, but are not capable of sustained cell division. Hence, a primary culture of the tissue cells can succeed, but due to a lack of sufficient cell divisions of the cultured cells, passaging of the primary culture to form serial cultures has not been possible. Although occasional cells in a metaphase stage, uptake of tritiated thymidine, and other evidence of cell division have been seen in these cultures (Clark et al., *Endocrinology*, 1990, 126:1895; Brelijie et al., *Endocrinology*, 1991, 128:45), the overall rate of cell division has been considered to be below the replacement rate (that is, more, or as many, cells die as are produced).

The culture of animal cells in vitro, as "biofactories," for the production of various proteins, peptides, hormones, growth factors, and other biologically active substances has been widely investigated. For example, pituitary cells have been cultured in vitro to produce growth hormone; kidney cells have been cultured to produce plasminogen activator; and hepatitis-A antigen has been produced in cultured liver cells. Other cells have been specifically cultured to produce various viral vaccines and antibodies. Interferon, insulin, angiogenic factor, fibronectin and numerous other biomolecules have been produced by the in vitro culture of various animal cells. Of course, the quantity of biomolecules produced by these biological factories is limited by the numbers of cells and range of cell types available.

Various cell lines have also been used in animal models of transplantation for a variety of purposes. Fetal kidney cells and amniotic cells have been transplanted as sources of trophic factors. Adrenal medullary cells, sympathetic ganglion cells, and carotid body cells have been transplanted as sources of dopamine. Fibroblasts and glial cells have been transplanted as sources of trophic factors, to carry genes through recombinant strategies, or for demyelinating diseases, for example. Corneal endothelial cells have been used for corneal transplants. Myoblasts have been transplanted for the treatment of muscular dystrophy and cardiac disease. Other cell lines include pancreatic islet cells for diabetes; thyroid cells for thyroid disorders; blood cells for AIDS, bone marrow transplant, and inherited disorders; bone and cartilage for osteoarthritis, rheumatoid arthritis, or for fracture repair; skin or fat cells for reconstructive purposes, such as in skin grafts after burns or cosmetic surgery; breast augmentation with fat; hair follicle replacement; liver cells for liver disorders inducing hepatitis; and retinal pigment epithelial cells (RPE) for retinitis pigmentosa and Parkinson's disease.

Unfortunately, the inability to procure large numbers of primary cells that are genetically stable has impeded the ability of medical science to progress in the area of cell transplant therapy. In addition, current sources for therapeutic donor cells are limited further by the inherent biological variability among the donors.

Stem cells are believed to have immense potential for therapeutic purposes for numerous diseases. Stem cells have been derived from numerous donor sources, including, but not limited to, embryonic, blast, tissue-derived, blood, and cord-blood cells; organ-derived progenitor cells; and bone marrow stromal cells; among others. Such stem cells can be differentiated along numerous pathways to produce virtually any cell type. These cells can be transplanted either before or after differentiation. From a therapeutic perspective alone, such cells may be useful for the treatment of a vast array of disorders. Examples of neurological disorders that can potentially be treated with stem cells include Parkinson's disease, Alzheimer's and Huntington's diseases, ALS, stroke, demyelinating disorders, epilepsy, head trauma, and spinal cord injury. However, stem cells share the same problem with other cells relating to the ability to proliferate the cells in vitro in sufficient quantities for diagnostic, investigational, or therapeutic purposes. Moreover, primary stem cells that have exhibited the most plasticity are embryonic stem cells. Obtaining large quantities of these cells is particularly problematic and raises ethical issues.

The above description of the state-of-the-art makes it apparent that there is a need for methods to maintain any and all cells in long-term cultures at increased proliferation rates, thereby providing a more plentiful and less costly supply of cells. Such long-term cultures could be developed as biological "factories" for the production of therapeutically useful proteins, for example. Well-established cell lines would also offer the possibility of in vitro bioassays based on the cells' responses to drugs and other chemicals (e.g., for toxicity and efficacy studies). There is also a need for the ability to produce a homogenous cell line, particularly a homogenous cell line of human origin. The availability of cells and cell lines that can be cryo-preserved is likewise lacking.

Continuously cultured cell lines would also be invaluable as a source of cells for cell transplant therapy, which has been found effective in correcting many disease states. For instance, diabetics could be stabilized and possibly cured through the implantation of cells that replace the function of insulin-secreting β-cells of the pancreas. Parkinson's patients could be treated with a ready supply of dopaminergic neurons, or stem cells giving rise to dopaminergic neurons. Such cell lines would also provide an endless supply of cells and tissue readily accessible for genetic modulation in vitro prior to transplant, for use in cell-mediated gene therapy. Thus, there exists a need for methods to produce cells and cell lines that would proliferate for extended periods in vitro yet faithfully retain their differentiated functions.

BRIEF SUMMARY OF THE INVENTION

The subject invention pertains to tumor cell lines useful for increasing the proliferation potential of cells, including cultures of human and other animal cells. The subject invention particularly pertains to a rat thyroid cell line (UCHT1) useful for increasing the proliferation potential of cells. The subject invention also concerns conditioned medium prepared from such tumor cell lines, and other tumor cell line extracts. The conditioned medium of the invention can be used to produce immortalized or continuous cell lines. The invention further pertains to the cell lines immortalized using the conditioned medium of the subject invention.

In a further aspect, the subject invention concerns a proliferation factor obtainable from a tumor cell line, such as the UCHT1 cell line, as well as methods of using a tumor cell line, its proliferation factor, tumor cell line conditioned medium, and/or other tumor cell line extracts, to increase the proliferation potential of cells. The proliferation factor is obtainable from tumor cells lines of various species, particularly mammalian species, such as rats and humans. The subject invention also concerns cell lines immortalized using a tumor cell line proliferation factor, or using compositions (e.g., conditioned medium and/or other tumor cell line extracts) containing such tumor cell line proliferation factors. In a specific embodiment, the proliferation factor is from about 30 kD to about 100 kD. The subject invention further pertains to fragments, analogues, or derivatives of the full-length tumor cell line proliferation factor. The methods of the subject invention can be used to enhance the proliferation potential of cells, including proliferation duration and/or proliferation rate. For example, the methods of the subject invention produce cell lines that proliferate indefinitely, and intervals between consecutive divisions of a cell as little as 24 hours can be achieved. Further, the cells of the subject invention can be grown in large-scale culture and cryopreserved with full retention of viability in vitro and in vivo.

In another aspect, the subject invention concerns methods for transplanting cells to a patient in need thereof. These methods can be used for alleviating the symptoms of a variety of disorders or trauma by administering proliferated cells of the invention to a patient (e.g., a human or other animal) in need thereof. For example, proliferated cells of the subject invention can be administered to a patient suffering from a pathological condition, such as a condition associated with cell death, cell loss, or cell dysfunction. Advantageously, using the methods of the subject invention, immortality can be conferred to cell lines without the necessity for incorporation of an oncogene. Therefore, the majority of proliferated cell lines produced by the methods of the subject invention are non-tumorgenic in vivo.

The proliferated cells of the invention can range in plasticity from totipotent or pluripotent stem cells (e.g., adult or embryonic), precursor or progenitor cells, to highly specialized cells, such as those of the central nervous system (e.g., neurons and glia). The proliferated stem cells of the subject invention can be obtained from a variety of sources, including embryonic tissue, fetal tissue, adult tissue, umbilical cord blood, peripheral blood, bone marrow, and brain, for example. Blast cells can be proliferated using the methods of the subject invention.

Using methods of the subject invention, stem cells can be modified, then subsequently proliferated. For example, stem cells can be modified through genetic modification (e.g., genetic engineering), differentiated with differentiation agents (e.g., trophic factors), or with adjuvants (e.g., chemotherapies, radiation therapies, and the like), then proliferated. Alternatively, stem cells can be proliferated, then subsequently modified.

Using methods of the subject invention, non-stem cells (e.g., specialized or mature cells, such as dopamine-producing neurons, or their precursors or progenitors) can be modified, then subsequently proliferated. For example, non-stem cells can be modified through genetic modification (e.g., genetic engineering), differentiated with differentiation agents (e.g., trophic factors), or with adjuvants (e.g., chemotherapies, radiation therapies, and the like), then proliferated. Alternatively, non-stem cells can be proliferated, then subsequently modified.

Cells of the subject invention, including B-cells and T-cells, for example, can be genetically modified to produce various biomolecules, such as trophic factors or antibodies, as well as to exhibit any number of bioactive properties. Cells can be genetically modified before, during, or after proliferation with a tumor cell line proliferation factor of the invention.

As will be understood by one of skill in the art, there are over 200 cell types in the human body. It is believed that the methods of the subject invention can be used to proliferate any of these cell types for therapeutic or other purposes. For example, any cell arising from the ectoderm, mesoderm, or endoderm germ cell layers can be proliferated using methods of the subject invention. It will be understood by one of skill in the art that the methods of the present invention are also applicable for veterinary purposes. For example, cells of non-human animals can find application either in human or animal patients (e.g., veterinary uses). Although dopamine neurons from human, pig, and rat are similar in that they synthesize dopamine and release synaptically into the brain, they differ immunologically, in extent of reinervation of the brain, in life span, and in infection agents associated with the specific donor or donor species. These traits can be exploited for their specific strengths and weaknesses.

The subject invention provides a ready source of cells for research, including pharmacological studies for the screening of various agents, and toxicologic studies for the cosmetic and pharmaceutical industries. The subject invention further provides cells that can be used as biofactories, for the large-scale production of biomolecules, either naturally or recombinantly.

The subject invention further pertains to nucleotide sequences, such as DNA sequences, encoding the proliferation factor of the subject invention disclosed herein, and the proliferation factor receptor. These nucleotide sequences can be synthesized by a person skilled in the art. The sequences may be used to genetically modify an appropriate host to confer upon that host the ability to produce the proliferation factor or its receptor. Hosts of particular interest include vertebrate cells disclosed herein, bacteria, and yeast, for example. The subject invention also concerns vectors containing nucleotide sequences encoding the proliferation factor or the proliferation factor receptor disclosed herein.

BRIEF DESCRIPTION OF THE DRAWINGS

FIGS. 2A–2F show phase contrast microscopic images of differentiated and undifferentiated RCSN cells. FIG. 2A (control) shows that undifferentiated RCSN cells tend to exhibit an epithelial-like morphology, with short or no processes and a more acidophylic cytoplasm. FIG. 2B shows that, after differentiation, cell proliferation is greatly reduced, and RCSN cells develop processes and establish contact with neighboring cells. FIGS. 2C and 2D show hematoxilin and eosin (H-E) staining, before and after differentiation, respectively. FIGS. 2E and 2F show melanin staining, before and after differentiation, respectively, using the ferrous ion capture technique, demonstrating a homogenous distribution of the pigment in cytoplasm, with faint labeling in undifferentiated stages and a substantial increase upon differentiation.

FIGS. 3A and 3B show RCSN cells stained for neuron specific enolase (NSE), before and after differentiation, respectively. FIGS. 3C and 3D show RCSN cells stained for synaptophysin (SNP), before and after differentiation, respectively. FIGS. 3E and 3F show RCSN cells stained for microtubular associated protein-2 (MAP-2), before and after differentiation respectively. FIGS. 3G and 3H show images of differentiated RCSN cells taken under epifluorescence conditions and stained for neurofilament and tetanus toxin, respectively.

FIGS. 4A–4D show immunohistochemical staining and micrographs of RCSN cells. FIGS. 4A and 4B show immunohystochemical staining for tyrosine hydroxilase (TH), under undifferentiated (control) and differentiated conditions, respectively. FIGS. 4C and 4D show micrographs using the ferrous ion capture technique, where fluorescent areas represent catecholamine deposits.

FIG. 5 shows $Ca^{2+}$ in fluo-3 loaded RCSN lines. The image shows cells three seconds after being stimulated with the addition of 200 μm glutamate, and even more intensely when using simultaneous depolarizing conditions (70 mM $K^+$). Fluorescence intensity is depicted in a pseudo color scale, which in ascending order is black-blue-green-yellow-orange-red.

FIGS. 7A–7C show micrographs of striatal sections of two rats sacrificed 16 weeks after RCSN-3 cell transplantation. FIGS. 7A and 7C show RCSN-3 cells immunostained with tyrosine hydroxilase (TH) at 10× and 40× magnification, respectively. FIG. 7B shows RCSN-3 cells immunostained for DOPA decarboxilase (DOPA-DC) at 40× magnification.

FIGS. 15A–15C show sections at the striatum level (2×, 5×, and 5× magnification, respectively) of a lesioned rat brain transplanted with RCSN-3 cells, with a $TH^+$ area in the middle of each section. In FIG. 15C, the diaphragm of the microscope is closed to contrast striasomes, and the $TH^+$ surrounds them (right) and in a linear projection (left). Somas are not evident at this magnification. FIGS. 15D and 15E show lesioned controls of rat striatum.

FIG. 16A shows calibration using 25 μM dopamine. FIGS. 16B and 16C show amperimetric signals of dopamine in RCSN-3 cells, after depolarizing stimulation with 70 mM external $K^+$. Deflections corresponding to dopamine are present, demonstrating that RCSN cells are capable of production and active secretion of dopamine in vitro.

FIG. 17A shows tissue culture media (control). FIG. 17B shows phosphate buffered saline (PBS) with antiproteases (AP) (control). FIG. 17C shows 10 μM MPTP with PBS and AP (control). FIG. 17D shows 10 μM $MPP^+$ with PBS and AP (control).

FIG. 18A shows 10 μM $MPP^+$ in RCSN-3 cell extract. FIG. 18B shows 10 μM MPTP in RCSN-3 cell extract. FIG. 18C shows 10 μM MPTP in RCSN-3 cell extract from differentiated cells. As expected, no $MPP^+$ peak is observed after incubation with MPTP, suggesting the lack of an MAO B activity in RCSN cells.

FIGS. 19A and 19B show DNA fragmentation in the RCSN-3 cell line treated with $MPP^+$ using the terminal deoxynucleotidyl transferase-mediated dUTP nick-end labeling technique (TUNEL). FIG. 19A shows RCSN-3 cells in the absence of $MPP^+$ (control) and FIG. 19B shows RCSN-3 cells treated with $MPP^+$.

FIG. 20A shows untreated RCSN-3 cells (control). FIG. 20B shows RCSN-3 cells in the presence of dopamine. FIG. 20C shows RCSN-3 cells in the presence of manganese.

FIG. 21A shows untreated RCSN-3 cells (control). FIG. 21B shows RCSN-3 cells in the presence of $MPP^+$.

FIGS. 22A and 22B show the ratio of emission of JC-1 monomer versus emission of "J" aggregate (Em(520 nm)/Em (590 nm)) in RCSN-3 cells.

FIG. 23 shows experimental results using four experimental conditions: (i) plastic dishes in the absence of L-Dopa; (ii) plastic dishes in the presence of L-Dopa; (iii) glass dishes in the absence of L-Dopa; and (iv) glass dishes in the presence of L-Dopa.

FIG. 25 shows that the main components are located at approximately 65 kD and 15 kD, which are associated with albumin and lactoalbumin, respectively. Most protein precipitates at 65%–80% of saturation with ammonium sulfate, but there are a greater number of proteins in the range of 40%–50% and 50%–65%. Theoretically, thyroglobulin precipitates at 40%–50%.

DETAILED DISCLOSURE OF THE INVENTION

Figure 1:
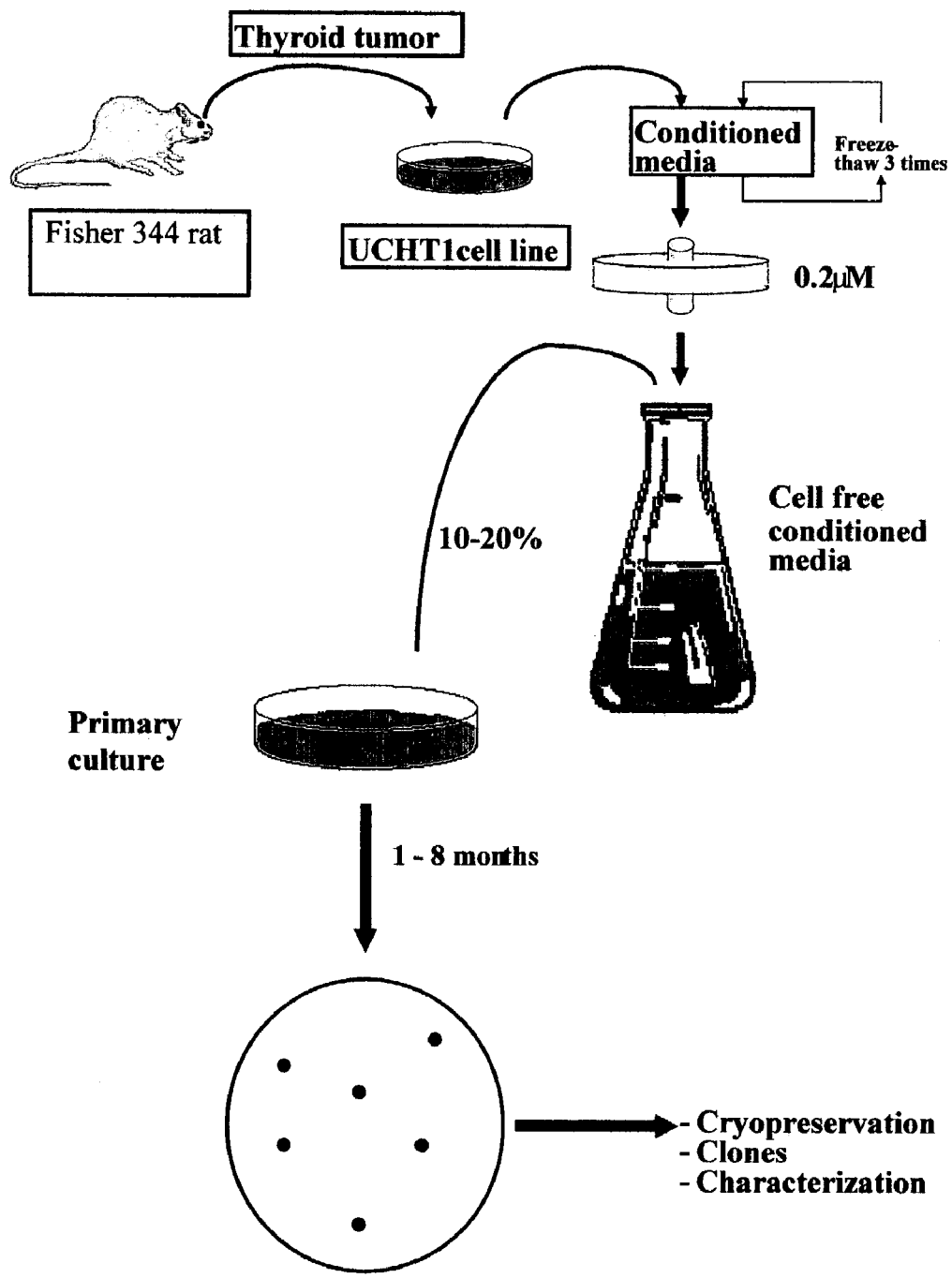
FIG. 1 shows a method of the subject invention, wherein media conditioned by the rat thyroid UCHT1 cell line for 48 hours is freeze-thawed 3 times in the absence of cryopreservants. The media is filtered through 0.2 µm filters to yield a cell free conditioned media. Primary cultures of mammalian origin are kept in the presence of 10–20% (v/v) for the time range indicated. Successful immortalization is assessed by the generation of transformation foci in the culture.
Figures 3A, 3B:
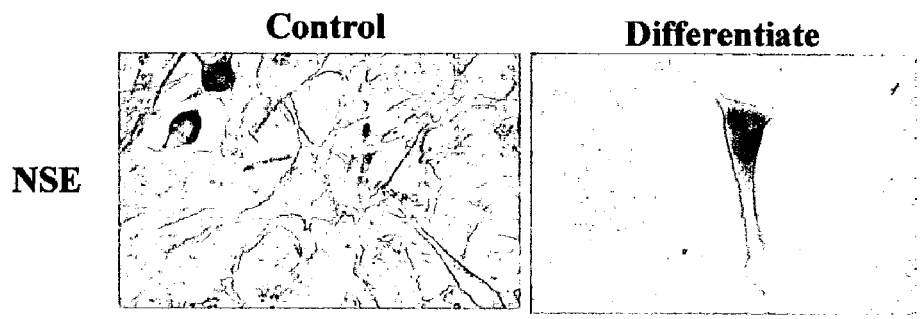
FIGS. 3A–3H show immunohistochemistry for neuronal markers.
Figures 3C, 3D:
Figures 3E, 3F:
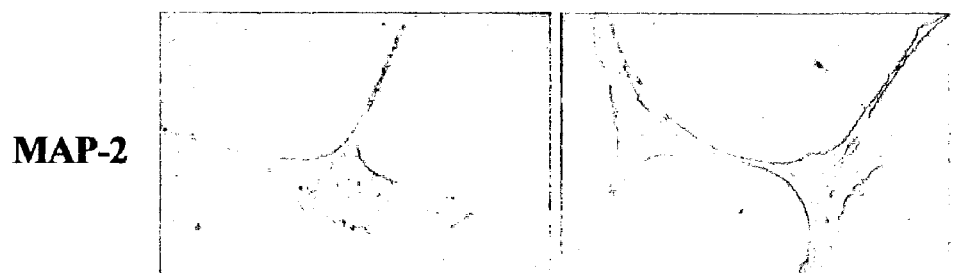
Figures 3G, 3H:
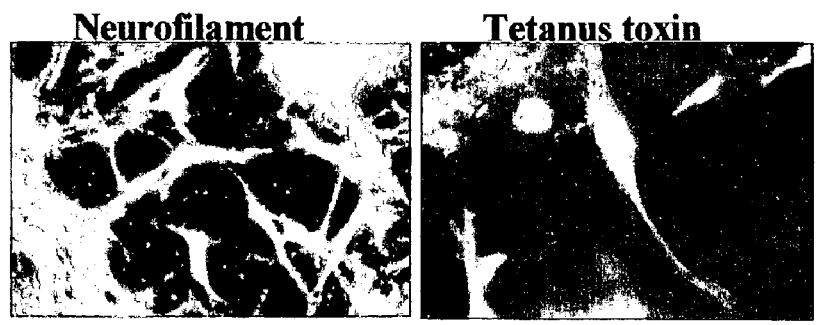

The subject invention pertains to tumor cell lines, such as the Fisher 344 rat thyroid cell line (UCHT1), useful for increasing the proliferation potential of cell cultures, including cultures of human and other animal cells, such that immortalized or continuous cell cultures are produced. The subject invention also concerns conditioned medium prepared from such tumor cell lines, which can also be used to produce immortalized or continuous cell lines. The invention further pertains to cell lines immortalized using conditioned medium of the subject invention.

In a further aspect, the subject invention concerns a proliferation factor produced by tumor cell lines, and methods of using tumor cell lines, their proliferation factor, conditioned medium, and/or other tumor cell line extracts, to increase the proliferation potential of cells. The subject invention also concerns cell lines immortalized using a tumor cell line proliferation factor, or using compositions (e.g., conditioned medium and/or other tumor cell line extracts) containing such tumor cell line proliferation factors. Conditioned medium can include medium in which the tumor cell lines of the subject invention (e.g., UCHT1) have been grown, wherein the proliferation factor is secreted or is otherwise delivered to the medium by the tumor cell line. In a specific embodiment, the proliferation factor is from about 30 kD to about 100 kD. The subject invention further pertains to polypeptides representing fragments, analogues, or derivatives of the full-length tumor cell line proliferation factor, or fusion proteins comprising such sequences, wherein the polypeptides retain some or all of the characteristic proliferating activity of the tumor cell line proliferation factors disclosed herein. The methods of the subject invention can be used to produce continuous cell lines that proliferate indefinitely. Many of these propagated cell lines have been maintained in vitro for one year and longer, and some for over 10 years, with retention of their differentiation markers. Using the methods of the present invention, it is possible to achieve a cell division period as little as 24 hours, or less.

The cells of the subject invention can be grown in large-scale culture and cryopreserved with substantial retention of viability. Advantageously, using the methods of the subject invention, cells can be transformed and continuous cell lines can be created without the necessity for incorporation of an oncogene within the target cell line. Hence, a tumor cell line, its proliferation factor, conditioned medium or other extract obtained from a tumor cell line, permits enhanced and/or sustained proliferation of a target cell. The tumor cell line can be derived from a wide variety of mammal species, including human. In one embodiment, the tumor cell line is a thyroid tumor cell line. In another embodiment, the tumor cell line is a rodent thyroid tumor cell line (e.g., rat or mouse cell line). In a still further embodiment, the tumor cell line is a rat thyroid cell line. In a specific embodiment, the tumor cell line is the rat thyroid tumor cell line, UCHT1.

The method for proliferating cells according to the subject invention, thereby producing immortalized or continuous cell lines, comprises the step of contacting a target cell or cells with a tumor cell line proliferation factor, such as the UCHT1 cell line proliferation factor. The proliferation factor induces or promotes the proliferation of the cells. In one embodiment, the method comprises culturing target cells in primary culture with conditioned medium from a tumor cell line, such as the Fisher 344 rat thyroid cell line, UCHT1. After a period of time in the range of about 1–8 months, cells become transformed into a continuously dividing but differentiated state. However, it should be understood that the duration of exposure to (e.g., contact with) a tumor cell line proliferation factor necessary to produce the continuous cell lines of the subject invention can vary with the type of target cell and the conditions under which contact is made. For example, durations of exposure shorter than one month and longer than eight months are also contemplated. The method for proliferating cells can also include the step of isolating the cell or cells from a human or other animal. The method for proliferating cells can optionally include a step of inducing the cells to differentiate.

In another aspect, the invention concerns a composition for proliferating cells. The composition of the invention comprises a proliferation factor produced by a tumor cell line, such as the UCHT1 cell line. In one embodiment, the composition is conditioned medium of a tumor line, wherein the conditioned medium contains a tumor cell line proliferation factor.

The tumor cell lines and proliferation factors of the subject invention are not the teratocarcinoma stem cell line (PSA-1) or factor described in Martin G. R., *Proc. Natl. Acad. Sci. USA,* December 1981, 78(12):7634–7638.

Various culturing methods known in the art can be used to contact the target cells with a tumor cell line proliferation factor (or compositions containing a proliferation factor) for a period of time, and in such a way that target cells are transformed and continuous cultures are produced. Propagation can be carried out under in vitro conditions, such as in suspension cultures or by allowing cells to adhere to a fixed substrate, or under in vivo conditions. For example, using a container with large growth surfaces, such as round bottles, cells can be grown in a confluent monolayer. The bottles can be rotated or agitated in motorized devices to keep the cells in suspension (e.g., the "roller flask" technique). Roller culture apparatus and similar devices are commercially available (WHEATON SCIENCE PRODUCTS).

The cells of the subject invention can be proliferated in culture as heterogeneous mixtures of cells or cell types, or clonally. A cell is said to be clonally derived or to exhibit clonality if it was generated by the division of a single cell and is genetically identical to that cell. Purified populations (clonal lines) are particularly useful for in vitro cell response studies, efficient production of specific biomolecules, and cell transplant therapy, because the exact identity of the cells' genetic capabilities and functional qualities are readily identified.

In order to produce the continuous cell lines of the subject invention, the target cells can be exposed to the tumor cell line proliferation factors disclosed herein by various methods known in the art. Furthermore, various techniques of isolating, culturing, and characterizing cells can be utilized to carryout the method of the subject invention, including those techniques described in Freshney R. I., ed., (2000), *Culture of Animal Cells: A Manual of Basic Technique,* Fourth edition, Wiley-Liss, New York. For example, the target cells can be exposed to a tumor cell line proliferation factor in the presence, or absence, of various substances, such as serum or other trophic factors.

A wide variety of media, salts, media supplements, and products for media formulation can be utilized to produce the continuous cell lines of the subject invention, depending upon the particular type of target cell. Examples of these substances include, but are not limited to, carrier and transport proteins (e.g., albumin), biological detergents (e.g., to protect cells from shear forces and mechanical injury), biological buffers, growth factors, hormones, hydrosylates, lipids (e.g., cholesterol), lipid carriers, essential and non-essential amino acids, vitamins, sera (e.g., bovine, equine, human, chicken, goat, porcine, rabbit, sheep), serum replacements, antibiotics, antimycotics, and attachment factors. These substances can be present in various classic and/or commercially available media, which can also be utilized with the subject invention. Examples of such media include, but are not limited to, Ames' Medium, Basal Medium Eagle (BME), Click's Medium, Dulbecco's Modified Eagle's Medium (DMEM), DMEM/Nutrient Mixture F12 Ham, Fischer's Medium, Minimum Essential Medium Eagle (MEM), Nutrient Mixtures (Ham's), Waymouth Medium, and William's Medium E.

The UCHT1 cell line was deposited with the following International Depository Authority (IDA): Deutsche Sammlung Von Mikroorganismen und Zellkulturen GmbH (DSMZ), Mascheroder Weg 1b, D-38124 Braunschweig, Germany on Feb. 1, 2002. The culture deposit number is DSM ACC2535.

The culture deposited for the purposes of this patent application was deposited under conditions that assure that access to the culture is available during the pendency of this patent application to one determined by the Commissioner of Patents and Trademarks entitled thereto under 37 C.F.R. § 1.14 and 35 U.S.C. § 122. The deposit will be available as required by foreign patent laws in countries wherein counterparts of the subject application, or its progeny, are filed. However, it should be understood that the availability of a deposit does not constitute a license to practice the subject invention in derogation of patent rights granted by government action.

Further, the subject culture deposit will be stored and made available to the public in accord with the provisions of the Budapest Treaty for the deposit of biological materials, i.e., they will be stored with all the care necessary to keep them viable and uncontaminated for a period of at least five years after the most recent request for the furnishing of a sample of the deposit, and in any case, for a period of at least thirty (30) years after the date of deposit or for the enforceable life of any patent which may issue disclosing the culture. The depositor acknowledges the duty to replace the deposit should the depository be unable to furnish a sample when requested, due to the condition of a deposit. All restrictions on the availability to the public of the subject culture deposit will be irrevocably removed upon the granting of a patent disclosing it.

In another aspect, the subject invention pertains to nucleotide sequences, such as DNA sequences, encoding the tumor cell line proliferation factor of the subject invention disclosed herein. The nucleotide sequences include not only the native sequences but also fragments of these sequences, analogues, and mutants of these sequences, wherein the encoded polypeptides retain some or all of the characteristic proliferating activity of the tumor cell line proliferation factors disclosed herein. These nucleotide sequences can be readily synthesized by a person skilled in the art. The sequences may be used to genetically modify eukaryotic or prokaryotic cells, for example, bacterial cells, mammalian cells, yeast cells or fungi cells for synthesis of the proliferation factor of the invention. Viruses may also be genetically modified using such polynucleotides, to serve as vectors for the delivery of the polynucleotides to host cells. Thus, in yet another aspect, the subject invention concerns vectors containing polynucleotides encoding the tumor cell line proliferation factor of the subject invention disclosed herein. Exemplary vectors include plasmids, cosmids, phages, viruses, liposomes, and lipid-conjugating carriers.

The various methods employed in the genetic modification of host cells are well known in the art and are described, for example, in Sambrook et al. (1989) *Molecular Cloning: A Laboratory Manual,* second edition, volumes 1–3, Cold Spring Harbor Laboratory, New York, and Gloves, D. M. (1985) *DNA Cloning, Vol. I: A Practical Approach,* IRL Press, Oxford. Thus, it is within the skill of those in the genetic engineering art to extract DNA from its source, perform restriction enzyme digestions, electrophorese DNA fragments, tail and anneal plasmid and insert DNA, ligate DNA, transform cells, e.g., prokaryotic and eukaryotic cells, prepare plasmid DNA, electrophorese proteins, and sequence DNA.

Using methods of the subject invention, stem cells can be modified, then subsequently proliferated. For example, stem cells can be modified through genetic modification (e.g., genetic engineering), differentiated with differentiation agents (e.g., trophic factors), or with adjuvants (e.g., chemotherapies, radiation therapies, and the like), then proliferated. Alternatively, stem cells can be proliferated, then subsequently modified.

Using methods of the subject invention, non-stem cells (e.g., specialized or mature cells, such as dopamine-producing neurons, or their precursors or progenitors) can be modified, then subsequently proliferated. For example, non-stem cells can be modified through genetic modification (e.g., genetic engineering), differentiated with differentiation agents (e.g., trophic factors), or with adjuvants (e.g., chemotherapies, radiation therapies, and the like), then proliferated. Alternatively, non-stem cells can be proliferated, then subsequently modified.

Accordingly, stem cells and non-stem cells (e.g., specialized or mature cells, or their precursors or progenitors) can optionally be modified before, during, and/or after proliferation, using the methods of the subject invention. The modification can be through one or more of the following interventions: genetic modification, differentiation with differentiation agents, or with adjuvants, for example. The differentiation induced can be partial differentiation or full differentiation along any number of phenotypic pathways, and can include changes to a cell's morphology and/or function.

Target Cells

The proliferated cells of the invention can be derived from humans or other mammals, including non-human primates, rodents, and pigs, for example. Specific examples of source species include, but are not limited to, apes, chimpanzees, orangutans, humans, monkeys; domesticated animals (pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, giant pandas, hyena, seals, sea lions, elephant seals, porpoises, dolphins, and whales. The target cells can also be derived from non-mammals, such as fish.

The proliferated cells of the invention can range in plasticity from totipotent or pluripotent stem cells (e.g., adult or embryonic), precursor or progenitor cells, to highly specialized or mature cells, such as those of the central nervous system (e.g., neurons and glia). Stem cells can be obtained from a variety of sources, including fetal tissue, adult tissue, umbilical cord blood, peripheral blood, bone marrow, and brain, for example. Stem cells and non-stem cells (e.g., specialized or mature cells, and precursor or progenitor cells) can be differentiated and/or genetically modified before, during, or after proliferation using the methods of the subject invention. As used herein, the term "embryo" is intended to include the morula, blastocyst, gastrula, and neurula. For example, blast cells can be proliferated using the methods of the subject invention.

Cloned cells, fertilized ova, and non-fertilized gametes can also be proliferated according to the methods of the invention. For example, fertilized ova or non-fertilized gametes can be used for reproductive purposes or cloning purposes.

Other cells that can be proliferated using methods of the subject invention include, but are not limited to, neural cells, including nigral dopaminergic neurons of fetal, neonatal, and adult origins; glial cell lines from mesencephalon and striatum, of fetal, neonatal, and adult origins; GABAergic cells from various areas of the brain, including striatum or cortex, of fetal, neonatal, and adult origins; cholinergic neurons from the striatum, septum, and nucleus basalis of fetal, neonatal, and adult origins; and serotogenic neurons derived from the lateral hypothalamus, dorsal raphe nucleus or hindbrain of embryonic, neonatal, or adult origins. Glial cells from numerous regions, including mesencephalon, striatum, cortex, subcortical white matter, spinal cord, or Schwann cells, of fetal, neonatal, and adult origins.

As will be understood by one of skill in the art, there are over 200 cell types in the human body. The methods of the subject invention are useful in proliferating any of these cell types, for therapeutic or other purposes. For example, cells that can be proliferated using the methods of the subject invention include those cells arising from the ectoderm, mesoderm, or endoderm germ cell layers. Such cells include, but are not limited to, neurons, glial cells (astrocytes and oligodendrocytes), muscle cells (e.g., cardiac, skeletal), chondrocytes, fibroblasts, melanocytes, Langerhans cells, keratinocytes, endothelial cells, epithelial cells, pigment cells (e.g., melanocytes, retinal pigment epithelial (RPE) cells, iris pigment epithelial (IPE) cells), hepatocytes, microvascular cells, pericytes (Rouget cells), blood cells (e.g., erythrocytes), cells of the immune system (e.g., B and T lymphocytes, plasma cells, macrophages/monocytes, dendritic cells, neutrophils, eosinophils, mast cells), thyroid cells, parathyroid cells, pituitary cells, pancreatic cells (e.g., insulin-producing $\beta$ cells, glucagon-producing $\alpha$ cells, somatostatin-producing $\delta$ cells, pancreatic polypeptide-producing cells, pancreatic ductal cells), stromal cells, Sertoli cells, adipocytes, reticular cells, rod cells, and hair cells. Other examples of cell types that can be proliferated using the methods of the subject invention include those disclosed by Spier R. E. et al., eds., (2000) *The Encyclopedia of Cell Technology,* John Wiley & Sons, Inc., and Alberts B. et al., eds., (1994) *Molecular Biology of the Cell,* $3^{rd}$ ed., Garland Publishing, Inc., e.g., pages 1188–1189.

Methods and markers commonly used to identify stem cells and to characterize differentiated cell types are described in the scientific literature (e.g., Stem Cells: Scientific Progress and Future Research Directions, Appendix E1–E5, report prepared by the National Institutes of Health, June, 2001). The list of adult tissues reported to contain stem cells is growing and includes bone marrow, peripheral blood, umbilical cord blood, brain, spinal cord, dental pulp, blood vessels, skeletal muscle, epithelia of the skin and digestive system, cornea, retina, liver, and pancreas.

According to methods of the subject invention, stem cells can be exposed to a tumor cell line proliferation factor by contact with the tumor cell line, tumor cell line conditioned medium, other tumor cell line extracts, or by contact with the purified proliferation factor itself. The stem cells can be exposed to the tumor cell line proliferation factor when the stem cells are at different stages of development, such as the blast stage, progenitor stage, stem cell stage, as well as committed to differentiated progenitor stage. It would be expected that the dividing cells would maintain a differentiated state proportional to the developmental stage in vitro, at which donor tissue is exposed to the conditioned medium.

Using methods of the subject invention, stem cells can be modified with differentiation agents (e.g., trophic factors), through genetic modification (e.g., genetic engineering), or with adjuvant (e.g., chemotherapies, radiation therapies, and the like), then subsequently proliferated. Alternatively, stem cells can be proliferated, then subsequently modified.

Undifferentiated stem cells can be cultured to a point where they are committed to becoming a particular cell type (e.g., dopamine neuron), then administered to a patient to complete their growth and differentiation within the host (e.g., within the host brain). Alternatively, less-committed stem cells can be administered to the patient, relying on "environmental" signals to guide them into becoming the appropriate type of replacement cells.

The cells of the subject invention can be induced to reduce their proliferation rate to the point that proliferation is arrested. For example, if cells have been proliferated using the methods of the subject invention such that their proliferation rate has been increased from its basal rate in culture, proliferation can be induced to cease simply by removing the proliferating cells from contact with the proliferation factor, or removing the proliferation factor from contact with the cells. If cells have been proliferated with the proliferation factor for a period of time sufficient to immortalize the cells (thus producing a continuous cell line) such that contact with the proliferation factor is no longer necessary to maintain proliferation, the cells can be induced to cease proliferation by differentiating the cells through differentiation protocols, such as serum deprivation, or contacting the cells with one or more differentiation agents, as described below. Advantageously, the cells of the subject invention can be induced to cease proliferation prior to administration to a patient.

Although the methods of the subject invention permit the proliferation of cells with at least some retention of their differentiated attributes, the cells of the subject invention can be induced to differentiate further along particular developmental paths, depending upon the particular cell's plasticity. For example, when cell proliferation is stopped, the cells of the subject invention can be categorized along a continuum that includes, but is not limited to, "wild type" cells having the exact cell type of the starting cell material and "wild type-like" cells such that they retain at least some of the properties or produce at least of the products of the starting cells, but not having fully differentiated into the starting cell type.

Depending upon cell type, differentiation of the cells can be induced by any method known in the art that activates the cascade of biological events that lead to cell growth. For example, cells can be induced to differentiate by plating the cells on a fixed substrate, such as a flask, plate, or coverslip, or a support of collagen, fibronectin, laminin, or extracellular matrix preparation such as MATRIGEL (Collaborative Research), or removal of conditioned medium. Cells can be incubated in dishes and on cover slips coated with MATRIGEL to allow gellification and subsequently seeded onto the treated surface (Cardenas, A. M. et al., *Neuroreport.*, 1999, 10:363–369). Differentiation can be induced by transfer to GM with 1% bovine serum and 10 µg/ml of both insulin and transferrin, wherein differentiating media is F12/D supplemented with 1% bovine serum and 1% stock supplement (Liberona, J. L. et al., *Muscle & Nerve*, 1998, 21:902–909). Horse serum can be utilized to increase fusion rate. Further differentiation procedures and agents can be found, for example, in Caviedes, R. et al., *Brain Research*, 1996, 365: 259–268, where preconfluent cultures were incubated in complete growth medium plus 2% dimethylsulfoxide for 10 days, and in Arrigada, C. et al., *Amino Acids*, 2000, 18(4): 363–373, where differentiation medium consisted of DMEM/Ham F12 nutrient mixture, supplemented with 2% adult bovine serum and 1% (v/v) of N3 supplement and 1% (v/v) Site+3 (SIGMA), and cells were allowed to differentiate for 1 week.

Cells can be stimulated to differentiate by contact with one or more differentiation agents (e.g., trophic factors, hormonal supplements), such as forskolin, retinoic acid, putrescin-transferrin, cholera toxin, insulin-like growth factor (IGF), transforming growth factor (e.g., TGF-α, TGF-β), tumor necrosis factor (TNF), fibroblast growth factor (FGF), epidermal growth factor (EGF), granulocyte macrophage-colony stimulating factor (GM-C SF), hepatocyte growth factor (HGF), hedgehog, vascular endothelial growth factor (VEGF), thyrotropin releasing hormone (TRH), platelet derived growth factor (PDGF), sodium butyrate, butyric acid, cyclic adenosine monophosphate (cAMP), cAMP derivatives (e.g., dibutyryl cAMP, 8-bromo-cAMP) phosphodiesterase inhibitors, adenylate cyclase activators, prostaglandins, ciliary neurotrophic factor (CNTF), brain-derived neurotrophic factor (BDNF), neurotrophin 3, neurotrophin 4, interleukins (e.g., IL-4), interferons (e.g., interferon-gamma), leukemia inhibitory factor (LIF), potassium, amphiregulin, dexamethasone (glucocorticoid hormone), isobutyl 3-methyulxanthine, somatostatin, lithium, and growth hormone.

The subject invention provides a ready source of cells for research, including pharmacological studies for the screening of various agents, and toxicologic studies for the cosmetic and pharmaceutical industries. The cells of the subject invention can be used in methods for determining the effect of a synthetic or biological agent on cells. The term "biological agent" refers to any agent of biological origin, such as a virus, protein, peptide, amino acid, lipid, carbohydrate, nucleic acid, nucleotide, drug, pro-drug, or other substance that may have an effect on cells, whether such effect is harmful, beneficial, or otherwise. Thus, the cells of the present invention can be used for screening agonists and antagonists of compounds and factors that affect the various metabolic pathways of a specific cell, for example. The choice of cell will depend upon the particular agent being tested and the effects one wishes to achieve. For example, cells from a cardiac muscle cell line can be incubated in a dose-escalation manner in vitro to evaluate changes in membrane potential, etc. Chemotherapies, such as the administration of ADRIAMYCIN, are known to cause cardiac toxicity. Therefore, cardiac cell lines of the subject invention are useful for testing such chemotherapies for cardiac toxicity. For example, the RCVC cell line of the subject invention described in Example 5 can be exposed to various synthetic or biological agents and the effects of the agents on the physiology of the cell can be determined by comparison of physiological criteria in a control (e.g. in the absence of the agents) (Caviedes, P. et al., *J. Molec. & Cell Cardiol.*, 1993, 25(1993):829–845). Further, sulfonamides induce toxicity of the pancreas acinar cells. Therefore, pancreatic acinar cell lines and other cell lines of the subject invention would be useful for testing the toxicity of such agents. As shown in FIGS. 19A–B, 20A–C, 21A–B, and 22A–B, RCSN-3 cells produced using the methods of the subject invention present characteristic properties of neuronal dopaminergic cells in vitro, presenting apoptotic phenomena when exposed to pro-neurodegenerative agents. Many drugs are known to induce liver damage. Therefore, to address this, a liver cell line of the subject invention can be used for toxicity testing. A kidney cell line can be proliferated and used similarly according to the methods of the subject invention.

The effects of synthetic or biological agents on the cells can be identified on the basis of significant difference relative to control cultures with respect to criteria such as the ratios of expressed phenotypes, cell viability and alterations in gene expression. Physical characteristics of the cells can be analyzed by observing cell morphology and growth with microscopy. Increased or decreased levels of proteins, such as enzymes, receptors and other cell surface molecules, amino acids, peptides, and biogenic amines can be analyzed with any technique known in the art which can identify the alteration of the level of such molecules. These techniques include immunohistochemistry, using antibodies against such molecules, or biochemical analysis. Such biochemical analysis includes protein assays, enzymatic assays, receptor binding assays, enzyme-linked immunosorbent assays (ELISA), electrophoretic analysis, analysis with high performance liquid chromatography (HPLC), Western blots, and radioimmune assays (RIA). Nucleic acid analysis, such as Northern blots and polymerase chain reaction (PCR) can be used to examine the levels of mRNA coding for these molecules, or for enzymes which synthesize these molecules.

Alternatively, cells treated with these agents can be transplanted into an animal, and their survival and biochemical and immunological characteristics examined as previously described.

Proliferated cells can be used as a platform for growing virus particles for vaccine production or other purposes. For example, human cervical epithelium can be proliferated in culture and used to support papopavirus in the development of a vaccine. In addition, fetal kidney cells are commonly used for the production of several different vaccines.

Cells proliferated by the methods of the subject invention can have a naturally occurring or induced defect, such that the cells provide an in vitro model of disease. As described above with respect to normal cells, these cells can be used to test effects of synthetic or biological agents in a disease model. For example, the establishment of stable, in vitro models of the nervous system will provide an important tool to rapidly and accurately address various neurological disorders. Therefore, a cell line proliferated according to the methods of the subject invention can be obtained having similar dysfunction mechanisms as the originating tissues, and which would serve as a model to study potential therapies and/or further alterations of the cell function. For example, muscle isolated from Duchenne muscular dystrophy patients can be used for investigating specific biochemical and genetic abnormalities associated with that disease.

In addition, the cells of the subject invention can be used to generate antibodies for cell-specific proteins, and elucidate the interactions between cell types and cell matrix components. Immune cells can be proliferated for administration to patients as immunotherapy. For example, B cell and T cell lines with specific anti-cancer properties can be proliferated and used for cell vaccine therapy (Couzin, J. *Science, Sep.* 20, 2002, 297:1973; Dudley M. E. et al. *Science, Oct.* 25, 2002, 298:850-854). Furthermore, antibody producing cell lines directed against tumor necrosis factor can be utilized for treatment of rheumatoid arthritis or psoriatic arthritis, and other autoimmune disorders. Antibodies to cell-surface markers may be generated and used to purify a subpopulation from a heterogenous population of cells using a cell sorting system. Using membrane fragments of cells of the subject invention, monoclonal antibodies can be produced according to methods known in the art (Kohler et al., *Nature,* 1975, 256:495; Kohler et al., *Eur. J. Immunol.,* 1976, 6:511-519) and screened using a variety of cell lines to identify antibodies that display cell specificity. In addition, cell-specific monoclonal antibodies can be used to purify cell-surface markers and identify their function. Stem cells and precursor cells of the subject invention can be labeled, for example, using β-galactosidase, and their ontogeny followed in heterogenous cell and nutrient environments.

Once an immortalized cell line has been established, genetic material from the cells can be used to construct cDNA libraries. Methods for preparing cDNA libraries are well known in the art (Sambrook et al., (1989) *Molecular Cloning: A Laboratory Manual, 2nd* Ed., Cold Spring Harbor Laboratory Press, Cold Springs Harbor, N.Y.; Ausabel et al., eds., *Current Protocols in Molecular Biology,* John Wiley and Sons, Inc. New York). By selecting cells at various stages of differentiation, the biological functions that are associated with a specific stage in the differentiation pathway can be identified once a cDNA library is prepared from that cell's mRNA. The libraries can be used to clone novel factors produced by specific cell types, such as differentiation factors, growth hormones, and other cytokines and growth factors.

Cell lines prepared by the methods of the subject invention can also be used to prepare a protein library, which is complementary to the cDNA library. Amino acid sequence information obtained from the library enables rapid isolation of cDNAs encoding proteins of interest. Coupling of protein and cDNA libraries also facilitates the targeted cloning of sequences of particular interest. A protein library is prepared by extracting protein (total proteins or fractions of interest) from cells according to known methods, and separating the proteins by two-dimensional gel electrophoresis, for example. Isolated proteins can then be subjected to in situ digestion (e.g., tryptic digestion) followed by separation by micro-bore HPLC. The separated fragments can then be analyzed by mass spectrometry. The resulting mass profile can be searched against a protein sequence database to infer protein identity. Unidentified peptides can be sequenced by Edman degradation. The resulting cDNA and protein libraries are valuable sources of new proteins and the sequences encoding them.

Cell Products

Cells can be proliferated using the methods of the subject invention and the cells' products harvested using methods known in the art. Various biomolecules produced by genetically modified or non-genetically modified cells that are proliferated using the methods of the subject invention can be harvested (e.g. isolated from the biomolecule-producing cells using methods known in the art) for various uses, such as the production of drugs and for pharmacological studies. Thus, using the methods of the subject invention, cells can be proliferated to produce continuously growing cells and be used as biological "factories" to provide the product of exogenous DNA and/or the natural product of the cells in vitro, or in vivo within an animal. The term "biomolecule" refers to any molecule or molecules that can be produced by cells. Such biomolecules include, but are not limited to, proteins, peptides, amino acids, lipids, carbohydrates, nucleic acids, nucleotides, viruses, and other substances. Some specific examples of biomolecules include trophic factors, hormones, and growth factors, such as brain-derived growth factor (BDNF) and glial-derived neurotrophic factor (GDNF). For example, pituitary cells can be proliferated to produce growth hormone; kidney cells can be proliferated to produce plasminogen activator; bone cells can be proliferated to produce bone morphogenetic protein (BMP) or other proteins involved in bony fusions or prosthetic surgery (Urist, M. R. and Strates, B. S. *J. Dent. Res. Suppl.,* 1971, 50:1392-1406; Boden, S. D. et al., *Spine,* 1995, 20:2633-2644; Boden, S. D. and Sumner, D. R. *Spine,* 1995, 20(Suppl. 24):102S-112S) and hepatitis-A antigen can be produced from proliferated liver cells. Cells can be proliferated to produce various viral vaccines and antibodies. Interferon, insulin, angiogenic factor, fibronectin and numerous other biomolecules can be produced by proliferating cells to establish continuous cell lines. The biomolecules can be intracellular, transmembrane, or secreted by the cells, for example.

Administration of Cells

In another aspect, the subject invention concerns methods for treating a variety of disorders or traumatic injury by administering cells from immortalized cell lines of the invention to a patient (e.g., a human or other animal) in need thereof. Optionally, the proliferated cells can be isolated (removed from contact with) the proliferation factor of the invention prior to their administration to a patient. Advantageously, because cells of the subject invention do not require the incorporation of an oncogene, and can be induced to arrest proliferation in vitro or in vivo, they can express a differentiated phenotype in vitro or in vivo. The majority of cell lines of the subject invention are non-tumorgenic in vivo. Therefore, non-tumorgenicity of a particular cell line can be determined using methods known in the art and the cells can be administered to a patient in need thereof.

The cell lines of the subject invention can be administered as cell therapy to alleviate the symptoms of a wide variety of disease states and pathological conditions, in various stages of pathological development. For example, cells of the subject invention can be used to treat acute disorders (e.g., stroke or myocardial infarction), and administered acutely, sub-acutely, or in the chronic state. Similarly, the cells of the subject invention can be used to treat chronic disorders (e.g., Parkinson's disease, diabetes, or muscular dystrophy), and administered preventatively and/or prophylactically, early in the disease state, in moderate disease states, or in severe disease states. For example, the cells of the subject invention can be administered to a target site or sites on or within a patient in order to replace or compensate for the patient's own damaged, lost, or otherwise dysfunctional cells. This includes infusion of the cells into the patient's bloodstream. The cells to be administered can be cells of the same cell type as those damaged, lost, or otherwise dysfunctional, or a different cell type. For example, insulin-producing pancreatic islet beta cells supplemented with other types of cells of the subject invention can be administered to the liver (Goss, J. A., et al., Transplantation, Dec. 27, 2002, 74(12):1761–1766). As used herein, patients "in need" of the cells of the subject invention include those desiring elective surgery, such as elective cosmetic surgery.

The cells of the invention can be administered as autografts, syngeneic grafts, allografts, and xenografts, for example. As used herein, the term "graft" refers to one or more cells intended for implantation within a human or other animal. Hence, the graft can be a cellular or tissue graft, for example.

Proliferated cells can be administered to a patient by any method of delivery, such as intravascularly, intracranially, intracerebrally, intramuscularly, intradermally, intravenously, intraocularly, orally, nasally, topically, or by open surgical procedure, depending upon the anatomical site or sites to which the cells are to be delivered. Proliferated cells can be administered in an open manner, as in the heart during open heart surgery, or in the brain during stereotactic surgery, or by intravascular interventional methods using catheters going to the blood supply of the specific organs, or by interventional methods such as intrahepatic artery injection of pancreatic cells for diabetics.

The cells of the subject invention can be administered to a patient in isolation or within a pharmaceutical composition comprising the cells and a pharmaceutically acceptable carrier. As used herein, a pharmaceutically acceptable carrier includes solvents, dispersion media, coatings, antibacterial and antifungal agents, isotonic agents, and the like. Pharmaceutical compositions can be formulated according to known methods for preparing pharmaceutically useful compositions. Formulations are described in a number of sources that are well known and readily available to those of ordinary skill in the art. For example, Remington's Pharmaceutical Science (Martin E. W., Easton Pa., Mack Publishing Company, 19$^{th}$ ed.) describes formulations that can be used in connection with the subject invention. Formulations suitable for parenteral administration, for example, include aqueous sterile injection solutions, which may contain antioxidants, buffers, bacteriostats, and solutes that render the formulation isotonic with the blood of the intended recipient; and aqueous and nonaqueous sterile suspensions that may include suspending agents and thickening agents. It should be understood that in addition to the ingredients particularly mentioned above, the formulations of the subject invention can include other agents conventional in the art having regard to the type of formulation and route of administration in question.

The cells of the subject invention can be administered on or within a variety of carriers that can be formulated as a solid, liquid, semi-solid, etc. For example, genetically modified cells or non-genetically modified cells can be suspended within an injectable hydrogel composition (U.S. Pat. No. 6,129,761) or encapsulated within microparticles (e.g., microcapsules) that are administered to the patient and, optionally, released at the target anatomical site (Read T. A. et al., Nature Biotechnology, 2001, 19:29–34, 2001; Joki T. et al., Nature Biotechnology, 2001, 19:35–38; Bergers G. and Hanahan D., Nature Biotechnology, 2001, 19:20–21; Dove A. Nature Biotechnology, 2002, 20:339–343; Sarkis R. Cell Transplantation, 2001, 10:601–607).

Microcapsules can be composed of various polymers and, in addition to cells, their contents can include enzymes and other materials. Preferably, the microcapsules are prepared in such a way as to prevent their contents from leaking out and potentially causing an immunological reaction, while permitting nutrients and metabolites to exchange freely. Microencapsulation of hepatocytes has been used to prepare so-called "bio-artificial liver assist devices" (BLAD). The high surface-to-volume ratio of a spherical microcapsule facilitates maximal transport of nutrients, gases, or metabolites exchange across the membrane. In addition, encapsulation of living cells allows better control of the microenvironment for optimal cellular functions via selection of suitable substrates and incorporation of controlled release features, as described below. Such devices can be used to deliver various types of cells proliferated according to the methods of the subject invention. Microcapsules can carry a payload of more than one type of cell. For example, islet cells can be encapsulated with Sertoli cells and administered to a patient.

Carriers are preferably biocompatible and optionally biodegradable. Suitable carriers include controlled release systems wherein the cells and/or the biological factors produced by the cells are released from the carrier at the target anatomic site or sites in a controlled release fashion. The mechanism of release can include degradation of the carrier due to pH conditions, temperature, or endogenous or exogenous enzymes, for example.

The cells of the invention can be administered in or on various scaffolds, such as synthetic or biological tissue scaffolds (Griffith G. and Naughton G., *Science*, 2002, 295:1009–1013; Langer R., *Stem Cell Research News*, Apr. 1, 2002, pp. 2–3). Porous scaffold constructs can be composed of a variety of natural and synthetic matrices, such as biominerals (e.g., calcium phosphate) and polymers (e.g., alginate) that are optionally cross-linked, and serve as a template for cell proliferation and ultimately tissue formation. Three-dimensional control of pore size and morphology, mechanical properties, degradation and resorption kinetics, and surface topography of the scaffold can be optimized for controlling cellular colonization rates and organization within an engineered scaffold/tissue construct. In this way, the morphology and properties of the scaffold can be engineered to provide control of the distribution of bioactive agents (e.g., proteins, peptides, etc.) and cells. In addition to use as vehicles for delivery of the proliferated cells, scaffolds can be utilized to grow the cells in vitro. Optionally, cells can be proliferated on the scaffolds themselves using the methods of the subject invention.

Scaffolds can contain interconnecting networks of pores and facilitate attachment, proliferation, and biosynthesis of cartilaginous matrix components, where desired. For example, synthetic or biological scaffolds carrying bone cells, such as chondrocytes, of the subject invention can be administered to a patient in need thereof. Chitosan scaffolds, which are biocompatible and enzymatically degraded in vivo, can be seeded with chondrocytes proliferated according to the methods of the subject invention and implanted. An alginate scaffold can be fabricated in the shape of a heart valve, seeded with proliferated cells of the invention, and implanted within a patient in need thereof. Because alginate does not naturally provide anchorage points for cells, in order to facilitate cell attachment, the peptide sequence R-G-D (Arginine-Glycine-Aspartic acid) can be utilized to act as a ligand for cell integrins and can be linked to alginate.

The cells of the subject invention are preferably administered to a patient in an amount effective to provide a therapeutic benefit. A "therapeutically effective amount" is that amount effective to treat a pathological condition. For purposes of the subject invention, the terms "treat" or "treatment" include preventing, inhibiting, reducing the occurrence of and/or ameliorating the physiological effects of the pathological condition to be treated. Preferably, the cells are administered to the patient in an amount within the range of about $10^4$ to about $10^{10}$ cells. More preferably, the cells are administered to the patient in an amount within the range of about $10^7$ to about $10^{10}$ cells. Doses of cells can be determined by one of ordinary skill in the art, with consideration given to such factors as cell survival rate following administration, the number of cells necessary to induce a physiologic response in the normal state, and the species of the patient.

Mammalian species which benefit from the disclosed methods of treatment include, and are not limited to, apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. As used herein, the term "patient" refers to a recipient of the cells of the subject invention. For example, suitable patients include the foregoing mammalian species.

The cell lines of the subject invention have advantages over other cells known in the art that are currently being utilized for transplantation purposes. The cell lines of the subject invention can be of human origin. The subject invention makes it possible to proliferate otherwise nondividing or very slowly dividing cells (e.g., dopaminergic neurons or insulin-producing beta-cells), which is an important aspect for the production of biological molecules and from a cell therapy perspective. Therefore, such cells can serve as clinical allografts from an immunological perspective, are available in adequate quantities, can be manufactured using good manufacturing processes, and can be produced free of contaminants from other cell types that might contaminate non-proliferated cells or cells derived from stem cells. The cells can be cryopreserved, are available for elective surgery, can be standardized and characterized before use. The cells can be rendered non-dividing and can have known HLA types that may facilitate advantageous immunologic matching or intentional mismatching, or allow for the production of multiple immunologically matched cell lines.

Using the methods of the subject invention, multiple identical cell lines from different donors can be created that vary only in their immunologic expression of surface antigens, based on the donor from which they are derived. Therefore, a cell line that has a close immunologic match to a particular potential recipient can be more closely customized. It is therefore possible using this technique to make a donor-specific cell line that is immunologically matched to the donor, or to make intentionally mismatched but related cell lines if so desired, for example, for the transplantation in genetic disorders where it may be desired to have a genetically mismatched cell line. Based upon the human population's various histotypes as well as current immunosuppression techniques, it has been determined that no more than twelve cell lines would be a sufficient donor source for the majority of ABO and type II antigen combinations found in 70%–80% of all Anglo Saxon patients in American and Europe. Furthermore, if the donor is type O, less than eleven cell lines would be a sufficient donor source.

For systemic transplants (e.g., pancreas), multiple different cell lines can be produced. Thus, a cell line that is similar to each patient can be available if enough cell lines are available, minimizing rejection risk. Additionally, if a patient requires a second transplant, a cell line that is different immunologically from the first can be transplanted, and there will not be induction of second-set rejection of the first cell line transplant. Furthermore, if the cell lines are not exactly immunologically the same as the patient, then discontinuation of the immunosuppression will cause graft rejection. This strategy can be used for elimination of toxicity if too many cells are transplanted or unexpected adverse events develop. In the CNS, immunologically unmatched cells will not be rejected, even in the absence of immunosuppression. Thus, for safety purposes, it may be necessary to be able to reject a neural graft if toxicity develops. For this, it would be necessary to grow a neural and skin cell line from the same donor (or, for example, dopamine neuron, retinal pigment epithelial cell, kidney cell, and skin cell, if these are to be transplanted into the CNS). Transplantation of the immunologically identical skin cell line orthotopically (into the periphery) will induce second set rejection of the neural graft (Freed, W. J., *Biological Psychiatry* [1983] 18:1204–1267; Nicholas, M. K. et al. *J. Immunology* [1987] 139:2275–2283; Mason D. W. et al. *Neuroscience* [1986] 19:685–694).

Combinations of cell lines can be co-administered to enhance therapeutic potential. For example, a trophic factor-producing cell line can be co-administered with a neuronal cell line. An insulin-secreting cell line and a glucagon cell line, with or without a pancreatic ductal cell line, can be co-administered for the treatment of diabetes. Methods of co-administration may include production of cell lines together (e.g., in a roller flask), or individually in separate batches that are mixed before implantation. Ratios and volumes of cells proliferated in culture can have some influence on efficacy and viability of cells in vitro or in vivo. A Sertoli cell line can be co-administered with a cell line of another species (as a xenograft), such that the Sertoli cells provide local immunosuppression of the xenograft. Sertoli cells can provide local immunosuppression for allografts (in addition to xenografts) transplanted systemically, such that immunosuppression may not be necessary (or only reduced amounts may be necessary).

Using normally non-dividing cell lines from the pancreas, the subject invention can provide a treatment for patients suffering from type 1 or type 2 diabetes, pancreatitis, post resection, or any condition requiring replacement of the pancreas. For example, human alpha and/or beta cells in the pancreas can be proliferated using the methods of the subject invention, for the purpose of replacing both glucagon and/or insulin-secretion properties of the pancreas. Entire pancreas islets containing a repertoire of pancreas cell types (e.g., α cells, β cells, δ cells, pancreatic polypeptide-producing cells) can also be proliferated and administered.

Further, proliferation of cells from other organs and tissues can be performed, including, but not limited to, cells of blood vessels, skin, fat, chondrocyte/bone, tendon, ligaments, and cartilage. Skin cells can be useful, for example, in treating chronic ulcers (e.g., decubitus or diabetic foot ulcers); tendon, ligament, and cartilage cells can be useful for treatment of degenerative diseases, osteoarthritis, and rheumatoid arthritis, as well as for orthopedic reconstructions. In addition, cardiac muscle or heart valve cells can be proliferated using the methods of the subject invention and administered to a patient following myocardial infarction or other causes of damage to heart muscle or valve. Liver cells can be proliferated for treatment of hepatitis or liver failure. Corneal cells can be proliferated for corneal transplants. Neuroendocrine chromaffin cells of the adrenal medulla can be proliferated using methods of the subject invention. Neuroendocrine chromaffin cells secrete opioid peptides, catecholamine, and several neuropeptides, including somatostatin, neuropeptide Y, and neurostatin, and can be administered to a patient (e.g., into the subarachnoid space, spinal cord, or brain) for acute or chronic pain conditions, such as inflammatory arthropathies and neuropathic pain. Sympathetic chain adrenergic neuron cells can also be proliferated. Chondrocytes can be proliferated for patients with arthrosis. For example, such cells can be obtained from the patient's other joints, proliferated to produce a chondrocyte cell line using the methods of the subject invention, and subsequently administered to the patient's diseased or damaged joints.

Hepatocytes of the subject invention can be administered directly to the patient's liver. However, in an alternative embodiment, hepatocytes proliferated using the methods of the subject invention can be placed within a device to be administered into the patient's circulatory system so that the cells can perform liver function at sites anatomically separate from the patient's liver (Sarkis R. et al., *Cell Transplantation*, 2002, 10:601–607). In addition to the administration of liver cells as therapy for hepatitis and metabolic disorders, these cells can also be administered for treatment of acute or chronic liver failure, either as a bridge for a patient awaiting liver transplantation or as a definitive therapy requiring no further liver transplantation (Kobayashi, N. and Tanaka, N., *Cell Transplantation*, 2002, 11:417–420). Further, liver cells can be administered as a cancer treatment for patients who require curative doses of hepatic radiation.

According to methods of the subject invention, it is also possible to proliferate hematogenous and lymphoid cells for the treatment of cancers such as lymphoma, myeloma, and leukemia, as well as for bone marrow transplantation purposes. Further, the proliferation of human dendritic (blood-derived) cells can be used in the restoration, repair, or augmentation of the immune system in immunotherapy, either in a disease state, such as in HIV, an autoimmune disorder, or cancer, or following chemotherapy or radiation therapy. Adrenal cortical tissue can also be proliferated for addressing adrenocortical insufficiency, such as in Addison's disease. Proliferated pituitary tissue is useful for pituitary insufficiency, such as for specific hormonal needs (i.e., TSH, prolactin, ACTH, or other hormone-producing cells from the pituitary), which is useful in transplantation following menopause, hysterectomy, or chemotherapy. Proliferated ovarian cells are also useful in similar situations. Further, egg cells can be proliferated for a variety of uses, such as cloning, research, or in vitro fertilization. Pulmonary mesenchymal cell line can be proliferated and administered for treatment of diseases of the lung including cystic fibrosis and emphysema. Cells of the vocal cords or stem cells can be proliferated and administered for the repair vocal cords or production of vocal cord organs. Likewise, thymus cells or stem cells can be proliferated for the production of immune cells, such as T cells, or the repair or production of thymus organs.

It has been observed that bone marrow transplants will induce tolerance before kidney transplantation of allogeneically related kidney donor. Therefore, using the methods of the subject invention, a bone marrow hematogenous cell line derived from the same donor as an organ cell line (e.g., pancreatic, heart, etc.) can be utilized to induce tolerance of the proliferated bone marrow hematogenous cell line (Dove A., *Nature Biotechnology*, 2002, 20:339–343).

Retinal cells can also be proliferated for transplantation to treat pathological conditions of the eye such as retinitis pigmentosa (a rhodopsin defect), ischemic retinopathy, and macular degeneration. Human retinal pigment epithelial cells and human iris pigment epithelial cells can be proliferated and administered to a patient for the restoration of vision or Parkinson's disease. Embryonic or other stem cells can be proliferated and administered subretinally to rescue photoreceptor cells from degeneration, for example.

According to the methods of the subject invention, neutrophils can be proliferated and be intravenously administered for treatment of septic shock in children, for example. This treatment can be utilized in cases of sepsis, as well as cancer patients that are immunocompromised following chemotherapy. Conventionally, it is not possible to obtain a sufficient amount of neutrophils for use in adult patients. For example, current protocols exist where neutrophil production is stimulated in patients with bone marrow suppression using colony stimulating factors, which is very expensive. Advantageously, using the methods of the subject invention, a neutrophil cell line can be proliferated and utilized for treatment of adult (and pediatric) sepsis patients. It should be understood that, even if the cells are rejected, it is expected that they would attack the infectious agents responsible for induction of septic shock before the cells are rejected.

The methods of the subject invention contemplate intracerebral grafting of donor cells to a region of the CNS, such as a region having sustained defect, disease, or trauma. Neural transplantation or "grafting" involves transplantation of cells into the central nervous system or into the ventricular cavities, or subdurally onto the surface of the host brain. Conditions relevant to successful transplantation include: (i) viability of the implant; (ii) retention of the graft at the appropriate site of transplantation; (iii) minimum amount of pathological reaction at the site of transplantation; (iv) maintenance of specific cell function; (v) prevention of immune reaction; and (vi) provision of trophic support and vascular supply. Parameters relevant to the above conditions include source of tissue, donor age, number of donors, distribution of grafted tissue, site of implantation, method of cell storage, and type of graft (cell suspension or solid).

Methods for transplanting various nerve tissues as allografts and xenografts have been described previously (Freeman T. B. et al., *Progress in Brain Research*, 1988, Chapter 61, 78:473–477; Freeman T. B. et al., *Parkinson's Disease: Advances in Neurology*, 2001, Chapter 46, 86:435–445; Freeman T. B. et al., *Annals of Neurology*, 1995, 38(3):379–387; Freeman T. B. et al., *Progress in Brain Research*, 2000, Chapter 18, 127:405–411; Olanow C. W. et al. *The Basal Ganglia and New Surgical Approaches for Parkinson's Disease, Advances in Neurology*, 1997, 74:249–269; Bjorklund et al., Neural Grafting in the Mammalian CNS, 1985, p. 709, Elsevier, Amsterdam; Das G. D., Neural Grafting in the Mammalian CNS, 1985, Chapter 3, p. 23–30, Elsevier, Amsterdam). These procedures include intraparenchymal transplantation, i.e., within the host brain tissue (as compared to outside the brain or extraparenchymal transplantation) achieved by injection or deposition of tissue within the host brain so as to be opposed to the brain parenchyma at the time of transplantation.

Methods for intraparenchymal transplantation include, for example: (i) injecting the donor cells within the host brain parenchyma (e.g., stereotactically, using image guidance, and/or with a catheter attached to a pump, such as a MEDTRONIC system); and (ii) preparing a cavity by surgical means to expose the host brain parenchyma and then depositing the graft into the cavity. Such methods provide parenchymal apposition between the graft and host brain tissue at the time of grafting, and both facilitate anatomical integration between the graft and host brain tissue.

Alternatively, the graft can be place into the cerebral spinal fluid (CSF), either by open surgical injection, intraventricularly via a needle or ventricular reservoir, into the lumbar subarachnoid space using a lumbar puncture, or into any CSF site using a pump and a catheter (e.g., MEDTRONIC). These methods would lend themselves to repeated administration over time, to the CSF or to the brain. Grafting to the ventricle may be accomplished by injection of the donor cells or by growing the cells in a substrate such as 3% collagen to form a plug of solid tissue which may then be implanted into the ventricle to prevent dislocation of the graft. For subdural grafting, the cells may be injected around the surface of the brain after making a slit in the dura. Injections into selected regions of the host brain can be made by drilling a hole and piercing the dura to permit the needle of a microsyringe to be inserted. The microsyringe can be mounted in a stereotactic frame and three-dimensional stereotactic coordinates are selected for placing the needle into the desired location of the brain or spinal cord. Image guidance methods can also be utilized. The cells of the subject invention can also be introduced into the putamen, caudate nucleus, pallidum, nucleus basalis, hippocampus, cortex, cerebellum, subcortical white matter, other regions of the brain, as well as the spinal cord using intravascular technique (Amar A. P. et al. Neurosurgery [2003] 52:402–413).

Many of the aforementioned cell lines produce trophic factors, including the Sertoli cell line, glial cell lines, and many of the aforementioned neuronal cell lines. Retinal pigment epithelial (RPE) cells, iris pigment epithelial (IPE) cells, kidney cells, and hNT cells, among others, produce neurotrophic factors. These cell lines are useful for their trophic factor production properties for the treatment of neurologic disorders, including, but not limited to, Parkinson's disease, Huntington's disease, amyotrophic lateral sclerosis (ALS), and stroke. For example, cells from immortalized cell lines of the subject invention can be administered to a patient to supplement the pool of dopaminergic neurons and to reinstate the dopaminergic input in the striatum. In addition, cells that natively or are modified to secrete ciliary neurotrophic factor (CNTF) and/or brain-derived neurotrophic factor (BDNF) can be proliferated and administered to a patient for treatment of Huntington's disease. Numerous trophic factors remain to be identified that play an important role in the development or maintenance of various cells in the body, both in normal and pathophysiological states. Using the methods of the subject invention, proliferation of cells that produce these factors is contemplated for both therapeutic and manufacturing purposes, as well as for investigational and laboratory purposes.

Adult stem cells or nondividing cells from a recipient with a disease of a particular organ can be proliferated using the methods of the subject invention for transplantation purposes. These cells can be isogenic (immunologically matched, donor-specific) with the particular patient. For example, if a pancreas has to be removed following an episode of pancreatitis, a similar piece of tissue can be proliferated for that individual patient and implanted without the need for immunosuppression. Heart muscle cells can likewise be proliferated and administered to replace damaged heart muscle in a patient suffering from congestive heart failure. This is particularly advantageous in non-life-threatening disorders, wherein the risk of immunosuppression is a concern. Such diseases include proliferation of corneal tissue for cornea replacement; tendon, ligament, and cartilage proliferation for orthopedic procedures or for treatment of degenerative disorders; ovarian cortical cell proliferation for hormonal replacement following menopause or hysterectomy; and keratinocyte and collagen preparations for diabetic ulcers, for example.

Genetically Modified Cells

The methods of the subject invention also contemplate the administration of genetically modified cells alone or in combinations with different types of cells. Thus, genetically modified cells of the invention can be co-administered with other cells, which can include genetically modified cells or non-genetically modified cells. Genetically modified cells may serve to support the survival and function of the co-administered cells, for example.

The term "genetic modification" as used herein refers to the stable or transient alteration of the genotype of a cell of the subject invention by intentional introduction of exogenous nucleic acids by any means known in the art (including for example, direct transmission of a polynucleotide sequence from a cell or virus particle, transmission of infective virus particles, and transmission by any known polynucleotide-bearing substance) resulting in a permanent or temporary alteration of genotype. The nucleic acids may be synthetic, or naturally derived, and may contain genes, portions of genes, or other useful polynucleotides. The term "genetic modification" is not intended to include naturally occurring alterations such as that which occurs through natural viral activity, natural genetic recombination, or the like. However, such naturally altered cells can also be proliferated according to the methods of the subject invention.

Exogenous nucleic acids can be introduced into a cell of the subject invention by viral vectors (retrovirus, modified herpes virus, herpes virus, adenovirus, adeno-associated virus, and the like) or direct DNA transfection (lipofection, calcium phosphate transfection, DEAE-dextran, electroporation, and the like), for example.

In another embodiment, the cells are derived from transgenic animals, and thus are in a sense already genetically modified. There are several methods presently used for generating transgenic animals. A typical technique is direct microinjection of DNA into single-celled fertilized eggs. Other methods include retro-viral-mediated transfer, or gene transfer in embryonic stem cells. These techniques and others are detailed by Hogan et al. in Manipulating the Mouse Embryo, A Laboratory Manual (Cold Spring Harbor Laboratory Ed., 1986).

The genetically modified cells (so called "designer cell lines") of the subject invention can be administered to a patient for cell/gene therapy, e.g., for in vivo delivery of various biomolecules, such as the trophic factors described above. Alternatively, the genetically modified cells can be used as biological "factories" to provide the product of the exogenous DNA and/or the natural product of the modified cells in vitro, or in vivo within an animal. Genetically modified cells can be stem cells or non-stem cells, for example.

The cells of the subject invention, whether genetically modified or non-genetically modified, can be co-administered with therapeutic agents useful in treating defects, trauma, or diseases, such as growth factors, antibiotics, or neurotransmitters.

The cells of the subject invention can be genetically modified (e.g., genetically engineered) to produce a vast array of biologically active molecules, such as cytokines, growth factors, antigens, receptors, glycoproteins, and enzymes, before, during, or after proliferation. Cells can be genetically modified to produce toxins, drugs for cell-based delivery, chemotherapy, neurotransmitters, and other biomolecules. Cells can be genetically modified to include regulators, inducible promoters, tissue-specific promoters, on-off genes, or suicide genes. Exogenous genes that interfere with oxidative stress (e.g., glutamate transporter) could be added to cells. B cells and T cells can be genetically modified to make monoclonal antibodies with targets for specific cancer cells, or against tumor necrosis factor (TNF), for treatment of rheumatoid arthritis or psoriatic arthritis.

Genetically modified cell lines can include more than one genetic construct. For example, a dopamine cell line can be constructed from embryonic stem cells, hNT neurons, or some other source. A secondary construct for glial-derived neurotrophic factor (GDNF), a potent factor for dopamine cell lines, can be added to the genetically modified dopamine cell line. The modified cell line can then be proliferated using the methods of the subject invention. Similarly, a secondary construct encoding antiapoptotic agents can be added. For example, genetic constructs encoding caspase inhibitors or interleukins can benefit a cell's function and survival.

Furthermore, sonic hedgehog (Shh) and FGF-8 are required for the induction of midbrain dopaminergic neurons during normal development, and the combination of Shh and FGF-8 can induce neurons with a dopaminergic phenotype in ectopic regions along the anterior neural tube (Ye, W. et al., Cell, 1998, 93:755–766). Cells of the subject invention (e.g., fibroblasts) can be genetically modified to produce Shh and/ or FGF-8 for therapeutic, manufacturing, or research purposes. For example, such genetically modified cells can be administered to a patient to significantly increase the number of surviving co-administered dopaminergic neurons (Yurek, D. M. et al., Cell Transplantation, 2001, 10:665–671).

Stem cells can be genetically modified, then subsequently proliferated using the methods of the subject invention. Alternatively, stem cells can be proliferated using the methods of the subject invention, then subsequently genetically modified.

Non-stem cells (e.g., specialized or mature cells, and their precursor or progenitor cells) can be genetically modified, then subsequently proliferated using methods of the subject invention. Alternatively, non-stem cells can be proliferated using the methods of the subject invention, then subsequently genetically modified.

Proliferation Factor and Receptor

There are at least two possible mechanisms for the activity of the tumor cell line proliferation factor described herein, which are not necessarily mutually exclusive. These mechanisms include, for example, phosphorylation of cyclin-dependent kinases (CDKs) or inhibition CKIs (CDK inhibitors); and/or interaction with telomerase or other DNA repair mechanisms (e.g., ligases), impairing normal DNA repair without compromising function. A further aspect of the subject invention includes methods of modulating the growth cycle of a cell or cells. Possible target cells include those described herein with respect to other methods of the subject invention. Modulation of a cell's growth cycle can be carried out by contacting or otherwise exposing the cells to the tumor cell line proliferation factor (including biologically active fragments or analogues thereof), agonists of the proliferation factor receptor, or functional antagonists of the proliferation factor receptor, such as antagonistic antibodies. Such agonists and antagonists may operate directly or indirectly on the proliferation factor receptor, and/or within the proliferation pathway.

The UCHT1 proliferation factor and its receptor are merely exemplary of other tumor cell line proliferation factors and corresponding proliferation factor receptors of the subject invention. Thus, the subject invention also includes variant or equivalent tumor cell line proliferation factors and proliferation factor receptors, such as the homologous human proliferation factor and proliferation factor receptor. Variant or equivalent tumor cell line proliferation factors and receptors (and nucleotide sequences coding for equivalent proliferation factors and receptors) have the same or similar activities to the UCHT1 proliferation factor and receptor. Equivalent proliferation factors and proliferation factor receptors will typically have amino acid homology with the exemplified UCHT1 proliferation factor and receptor, respectively. This amino acid identity will typically be greater than 60%, preferably greater than 75%, more preferably greater than 80%, more preferably greater than 90%, and can be greater than 95%. These identities are determined using standard alignment techniques. The amino acid homology will be the highest in critical regions of the proliferation factor and receptor which account for biological activity or are involved in the three-dimensional configuration which ultimately is responsible for the biological activity. In this regard, certain amino acid substitutions and/or deletions are acceptable and can be expected if these substitutions and deletions are in regions which are not critical to activity or are conservative amino acid substitutions or deletions which do not affect the three-dimensional configuration of the molecule. For example, amino acids can be placed in the following classes: non-polar, uncharged polar, basic, and acidic. Conservative substitutions whereby an amino acid of one class is replaced with another amino acid of the same type fall within the scope of the subject invention so long as the substitution does not completely eliminate the biological activity of the proliferation factor or proliferation factor receptor; however preferred substitutions are those which result in the retention of most or all of the biological activity of the proliferation factor or proliferation factor receptor. Table 1 provides a listing of examples of amino acids belonging to each class.

TABLE 1

| Class of Amino Acid | Examples of Amino Acids |
| --- | --- |
| Non polar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not completely eliminate the biological activity of the receptor; however, preferred substitutions are those which result in the retention of most or all of the biological activity of the proliferation factor or proliferation factor receptor. The use of polynucleotide probes is well known to those skilled in the art. In one specific example, a cDNA library for tumor cells (e.g., a thyroid tumor cell line) can be created by routine means, and DNA of interest can be isolated from the cDNA library. Polynucleotides of the subject invention can be used to hybridize with DNA fragments of the constructed cDNA library, allowing identification of and selection (or "probing out") of the genes of interest, i.e., those nucleotide sequences which hybridize with the probes of the subject invention and encode polypeptides having proliferation factor activity or proliferation factor receptor activity. The isolation of these genes can be performed by a person skilled in the art having the benefit of the instant disclosure, using techniques which are well-known in the molecular biology art.

Thus, it is possible, without the aid of biological analysis, to identify polynucleotide sequences encoding tumor cell line proliferation factors and corresponding receptors. Such a probe analysis provides a rapid method for identifying genes encoding proliferation factors and proliferation factor receptors from a wide variety of hosts. The isolated genes can be inserted into appropriate vehicles which can then be used to transform a suitable host. The presence of genes encoding the proliferation factors and proliferation factor receptors of the subject invention can be determined in a variety of hosts, including cells other than those of tumor cell lines.

Various degrees of stringency of hybridization can be employed. The more severe the conditions, the greater the complementarity that is required for duplex formation. Severity of conditions can be controlled by temperature, probe concentration, probe length, ionic strength, time, and the like. Preferably, hybridization is conducted under moderate to high stringency conditions by techniques well known in the art, as described, for example, in Keller, G. H., M. M. Manak (1987) *DNA Probes,* Stockton Press, New York, N.Y., pp. 169–170.

Examples of various stringency conditions are provided herein. Hybridization of immobilized DNA on Southern blots with $^{32}$P-labeled gene-specific probes can be performed by standard methods (Maniatis et al. (1982) *Molecular Cloning: A Laboratory Manual,* Cold Spring Harbor Laboratory, New York). In general, hybridization and subsequent washes can be carried out under moderate to high stringency conditions that allow for detection of target sequences with homology to the exemplified polynucleotide sequence. For double-stranded DNA gene probes, hybridization can be carried out overnight at 20–25° C. below the melting temperature (Tm) of the DNA hybrid in 6×SSPE, 5× Denhardt's solution, 0.1% SDS, 0.1 mg/ml denatured DNA. The melting temperature is described by the following formula:

$$Tm = 81.5° C. + 16.6 \text{Log } [Na+] + 0.41(\% \ G+C) - 0.61(\% \text{ formamide}) - 600/\text{length of duplex in base pairs}$$

(Beltz et al. (1983) *Methods of Enzymology,* R. Wu, L. Grossman and K. Moldave [eds.] Academic Press, New York 100: 266–285).

Washes are typically carried out as follows:
(1) twice at room temperature for 15 minutes in 1×SSPE, 0.1% SDS (low stringency wash);
(2) once at Tm −20° C. for 15 minutes in 0.2×SSPE, 0.1% SDS (moderate stringency wash).

For oligonucleotide probes, hybridization can be carried out overnight at 10–20° C. below the melting temperature (Tm) of the hybrid in 6×SSPE, 5× Denhardt's solution, 0.1% SDS, 0.1 mg/ml denatured DNA. Tm for oligonucleotide probes can be determined by the following formula:

$$Tm(° C.) = 2(\text{number } T/A \text{ base pairs}) + 4(\text{number } G/C \text{ base pairs})$$

(Suggs, S. V., et al. (1981) *ICN-UCLA Symp. Dev. Biol. Using Purified Genes,* D. D. Brown [ed.], Academic Press, New York, 23:683–693).

Washes can be carried out as follows:
(1) twice at room temperature for 15 minutes 1×SSPE, 0.1% SDS (low stringency wash);
(2) once at the hybridization temperature for 15 minutes in 1×SSPE, 0.1% SDS (moderate stringency wash).

In general, salt and/or temperature can be altered to change stringency. With a labeled DNA fragment >70 or so bases in length, the following conditions can be used:

| Low: | 1 or 2X SSPE, room temperature |
| --- | --- |
| Low: | 1 or 2X SSPE, 42° C. |
| Moderate: | 0.2X or 1X SSPE, 65° C. |
| High: | 0.1X SSPE, 65° C. |

Duplex formation and stability depend on substantial complementarity between the two strands of a hybrid and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions and deletions can be produced in a given polynucleotide sequence in many ways, and these methods are known to an ordinarily skilled artisan. Other methods may become known in the future.

As used herein, the terms "proliferate" and "propagate" are used interchangeably to refer to cell division. In the context of proliferating cells by contacting or otherwise exposing the cells to a tumor cell line proliferation factor, a tumor cell line that produces such a proliferation factor, or a composition containing a tumor cell line proliferation factor (e.g., conditioned medium), it is intended that proliferation can include proliferation to the point of production of a continuous cell line (e.g., immortalization, non-neoplastic, or non-malignant transformation). The proliferation factors of the subject invention have a pro-proliferative effect on cells contacted with the factor. When contacted with the factor, the cells are induced to attain a proliferation rate that is higher than the cells' normal proliferation rate in vitro, thus increasing the cells' potential for proliferation.

As used herein, the term "culture" is used to denote the maintenance or cultivation of cells in vitro including the culture of single cells. Cultures can be cell, tissue, or organ cultures, depending upon the extent of organization.

As used herein, the term "cell line" is used to refer to cells which have arisen from a primary culture and capable of successful subculture.

As used herein, the term "continuous cell culture" or "continuous cell line" is used to refer to a culture or cell line which is capable of an unlimited number of population doublings; often referred to as an immortal cell culture or cell line. Such cells may or may not express the characteristics of in vitro neoplastic or malignant transformation. This is antithesis of a finite cell culture or cell line, which is capable of only a limited number of population doublings after which the culture or cell line ceases proliferation (i.e., in vitro senescence).

As used herein, the term "immortalization" refers to the attainment by a finite cell culture, whether by perturbation or intrinsically, of the attributes of a continuous cell line. An immortalized cell line is not necessarily one which is neoplastically or malignantly transformed.

As used herein, the term "isolated" means removal from its native environment, and can include removal from its immediate native environment. As used herein, the term "isolated factor" or "isolated proliferation factor" indicates that the factor has been isolated from the tumor cell line (e.g., the UCHT1 cell line) that produces it.

As used herein, the term "differentiated" refers to those cells that maintain in culture all, or a substantial amount of, their specialized structure and function typical of the cell type in vivo. Partially differentiated cells maintain less than a substantial amount of their full complement of specialized structure and/or function.

As used herein, the term "stem cell" is an unspecialized cell that is capable of replicating or self renewal, and developing into specialized cells of a variety of cell types. The product of a stem cell undergoing division is at least one additional stem cell that has the same capabilities of the originating cell. For example, under appropriate conditions, a hematopoietic stem cell can produce a second generation stem cell and a neuron. Stem cells include embryonic stem cells (e.g., those stem cells originating from the inner cells mass of the blastocyst) and adult stem cells (which can be found throughout the more mature animal, including humans). As used herein, stem cells are intended to include those stem cells found in animals that have matured beyond the embryonic stage (e.g., fetus, infant, adolescent, juvenile, adult, etc.). The list of tissues reported to contain stem cells is growing and includes, for example, bone marrow, peripheral blood, brain, spinal cord, umbilical cord blood, amniotic fluid, placenta, dental pulp, blood vessels, skeletal muscle, epithelia of the skin and digestive system, cornea, retina, liver, and pancreas.

As used herein, the term "progenitor cell" (also known as a precursor cell) is unspecialized or has partial characteristics of a specialized cell that is capable of undergoing cell division and yielding two specialized cells. For example, a myeloid progenitor/precursor cell can undergo cell division to yield two specialized cells (a neutrophil and a red blood cell).

As used herein, the term "phenotype" refers to all the observable characteristics of a cell (or organism); its shape (morphology); interactions with other cells and the non-cellular environment (e.g., extracellular matrix); proteins that appear on the cell surface (surface markers); and the cell's behavior (e.g., secretion, contraction, synaptic transmission).

As used herein, the terms "administer", "apply", "treat", "transplant", "implant", "deliver", and grammatical variations thereof, are used interchangeably to provide cells of the subject invention to a patient.

As used herein, the term "co-administration" and variations thereof refers to the administration of two or more agents simultaneously (in one or more preparations), or consecutively.

All patents, patent applications, and publications referred to or cited herein are incorporated by reference in their entirety, including any figures, tables, nucleic acid sequences, amino acid sequences, or drawings, to the extent they are not inconsistent with the explicit teachings of this specification.

Materials and Methods

Establishment of RCSN-3 cell line. The RCSN-3 cell line was derived from the substantia nigra of 4 month old normal Fisher 344 rats. The cells used to establish primary cultures were immortalized by exposing them to media conditioned by UCHT1 cells (as shown in FIG. 1). For standard culture conditions, the cells were kept in feeding medium consisting of DMEM/Ham F12 nutrient mixture (1:1) (SIGMA Chemical Co., Saint Louis, Mo., USA) modified to contain 6 g/l glucose, 10% bovine serum, 2.5% fetal bovine serum, 100 U/mL penicillin, 100 μg/mL streptomycin (SIGMA) supplemented with 10% (v/v) with UCHT1 conditioned medium. The cultures were maintained in an incubator at 37° C. with 100% humidity and an atmosphere of 10% $CO_2$ and were monitored routinely for the appearance of transformation foci or morphological changes. After 10 weeks in culture, transformation foci were evident. The cultures were expanded and part was cryopreserved in liquid nitrogen. The cell line was cloned by dilutional culturing, giving rise to the clonal line RCSN-3. Cells were passaged at confluence with trypsinization (1% trypsin, GIBCO, Grand Island, N.Y., USA). For standard growth conditions, RCSN-3 cells were cultured in feeding medium. Media was renewed completely twice a week. For differentiation, the cells were kept in a media consisting of DMEM/Ham F12 nutrient mixture, supplemented with 2% adult bovine serum and 1% (v/v) of N3 supplement as previously described (Cardenas A. M. et al., *Neuroreport*, 1999, 10(2):363–369) and 1% (v/v) Site+3 supplement (SIGMA). Cells were allowed to differentiate for one week.

Cytology of RCSN-3 cell line. Cells were fixed in formaldehyde 4% in phosphate buffer pH 7.4. Cytochemical reactions included: Hematoxilin-eosin staining, ferrous ion capture to demonstrate the presence of melanin in the form of neuromelanin, paraformaldehyde-glyoxylate staining to demonstrate the presence of catecholamines.

Immunohistochemistry of RCSN-3 cell line. Fixed cells were permeabilized in an ascending/descending alcohol battery ranging from 50% to 96%. The blocking reaction was carried out using BSA 1% in phosphate buffer. The antibodies utilized were: (i) neuronal markers: NSE (pre-diluted, BIOGENEX) Synaptophysin (pre-diluted, BIOGENEX), MAP-2 (1:1000, SIGMA); (ii) glial markers: GFAP (pre-diluted, BIOGENEX), S-100 (pre-diluted, BIOGENEX); and (iii) functional markers: TH (1:1000-1:1500, SIGMA). The incubation with the primary antibodies was carried out overnight and an ABC detection kit (BIOGENEX) was used to develop the reaction and utilizing DAB as chromogen. Specific primary antibodies, fluorescein labeled secondary antibodies and tetanus toxin were used to evaluate the presence of neurofilament 200 kD and tetanus toxin receptor.

Intracellular $Ca^{2+}$ measurements. For intracellular $Ca^{2+}$ measurements, the cells were replated onto 35 mm culture dishes. The variations of intracellular $Ca^{2+}$ were assessed by $Ca^{2+}$-imaging techniques using Fluro-3. The cells were incubated at 37° C. for 40–60 minutes with the indicator. The dishes were visualized in an OLYMPUS BH2 microscope equipped with epifluorescence (halogen lamp). The microscope was connected to a Cooled Extended Isis digital camera (PHOTONIC SCIENCE, Ltd, Robertsbridge, UK) connected to a dedicated PC equipped with an AXON DIGIDATA 2000 digitizing board (AXON Instruments, Foster City, Calif.). Images were acquired at 12 bit resolution and 1 Hz using customized software AXON Imaging Workbench 2.1.80 (AXON). The compositions of the normal extracellular solutions were (in mM): 135 or 145 NaCl, 5 KCl, 2 $MgCl_2$, 1.5 or 2.5 $CaCl_2$, 10 4-(2-hidroxyethil) piperazine-1-ethanesulfonic acid (HEPES)-NaOH, 10 Dextrose (pH=7.4).

Surgical procedures and behavioral testing. Four adult male Fisher 344 rats (200–250 g) were lesioned by unilateral injection of 6-hydroxydopamine bromide at two sites along the medial forebrain bundle. Assessment of apomorphine induced rotational behavior (i.e. injection of 5 mg apomorphine per kg body weight, National Health Service, Chile) was carried out visually twice, once per week, before transplantation. Only rats with more than 160 rotations every 30 minutes were utilized after three times after transplantation (days 30, 55, and 80). For transplant, confluent cultures were washed in PBS and dissociated with 1% trypsin. 500,000 cells in a volume of 4 μL were implanted through blunt Hamilton syringes and deposited at AP +1.0 mm, ML −2.5 mm, and V −4.7 mm (coordinates relative to bregma), toothbar set at −2.5. Rotational behavior was assessed visually every two weeks after transplantation.

Purification and characterization of UCHT1 proliferation factor. A two-stage approach was used for the isolation and characterization of the UCHT1 proliferation factor: (i) collection of media conditioned by UCHT1 cell line; and (ii) identification of the proliferation factor (i.e., transformation promoting factor(s)) associated with the UCHT1 tumor cell line, and testing in bioassay. Culture media is composed of DMEM/Ham F12 nutrient mixture (1:1) (SIGMA Chemical Co, St. Louis, Mo. Cat# D8900), supplemented with 1 g/l bicarbonate. To this basal media, the following modifications were made: complete media: Contains 87.5% basal media, 10% adult bovine serum and 2.5% fetal bovine serum; 2% Serum media: 98% basal media+2% fetal bovine serum; and cryopreservation media: 70% basal media, 20% fetal bovine serum and 10% DMSO. When not in use, cells were stored in cryotubes with cryopreservation media, and kept in liquid nitrogen. Cells were thawed within 90 seconds in a water bath at 37° C. Thawed cells were seeded onto culture dishes and fed complete medium. The dishes were kept at 37° C., 100% humidity and 10% $CO_2$, and media was renewed every 3 days. When the cells reached confluence, a passage was performed. The cells were then washed with PBS and detached by trypsinization (trypsin 0.1%) and resuspended by pipetting. The cells were centrifuged at 1000 r.p.m. for 10 minutes, and the supernatant was discarded. Cells were then seeded onto new dishes at a 1/20 slit and fed complete medium.

Cryopreservation for purification and characterization of UCHT1 proliferation factor. Media was aspirated from the culture dishes, and the cells were washed with PBS and detached with trypsin 0.1%. The suspension was centrifuged at 1000 r.p.m. and the cell pellet was resuspended in cryopreservation media, at a density of $1\times10^6$ per ml. The suspensions were placed in cryotubes and frozen in a first stage to −86° C., at a rate of 1° C./minute. After 24 hours, the cryotubes were transferred to liquid nitrogen for the final storage.

Collection and pretreatment of UCHT1 conditioned media for purification and characterization of UCHT1 proliferation factor. UCHT1 cells were cultured in 15 cm diameter Petri dishes to confluence. At this time, conditioned media was collected and frozen at −20° C. Media was thawed and refrozen in 3 more cycles. Later, the media was centrifuged at 5000 r.p.m. for approximately 20 minutes and the supernatant was filtered through 0.2 μm porosity nitrocellulose filters. Media with serum and basal media without serum exposed to confluent UCHT1 cultures for 24 hours were collected. For chromatography studies, desalinization and concentration procedures were performed. Media samples were passed through PD-10 columns containing SEPHADEX G-25 M (PHARMACIA BIOTECH), where the sample was diluted by a factor of 1.4. The samples were then concentrated in CENTRICON molecular filter vials (AMICON) by centrifuging in a SORVALL RC-28S refrigerated centrifuge (DUPONT) at 4800 r.p.m. for 2.5 hours 100 μl of Tween 80 at 0.1% was added per vial.

Gel electrophoresis for purification and characterization of UCHT1 proliferation factor. Polyacrilamide gels containing sodium dodecyl sulfate (SDS, SDS-PAGE) were used. A total of 1.4 g SDS for the union of 1 g protein was considered, to achieve an adequate charge-mass correlation. The gels were run in a BIORAD electrophoresis chamber (MINI PROTEAN II), at 12.5% acrylamide and 10 columns per sample. The sensitivity of this gel is 0.1 μg to 1.0 μg of protein per band dyed with bright Coomassie blue and 2 ng to 10 ng in silver stains. The resolution is 15 kDa–60 kDa (Bollag, D. et al. (1996) *Protein Methods,* $2^{nd}$ Edition). Gels ran at 200V for 45 minutes, using an EPS 3500 XL Electrophoresis Power Supply, (PHARMACIA BIOTECH) or Power Pac 1000 (BIORAD). Isoelectric focusing (IEF) allows separation of proteins by net charge, as they migrate in a pH gradient generated by an electrical field, indicating the isoelectric point of the proteins. The Phast System method was used, with a commercial gel Phast Gel 1% Agarosa IEF containing Pharmalyte 3 to 9. This gel was selected to its broad spectrum of pI. The focusing stage is carried out continuously, and the gels are later dyed with silver nitrate and later the dye is removed. The gel has no gradient, so the respective pI is visualized linearly.

Chromatography for purification and characterization of UCHT1 proliferation factor. Hydrophobic interaction and ion exchange resins were used. An FPLC liquid chromatography kit was used, commanded by a software FPLC DIRECTOR. Appropriate binding and deadsorption buffers were used. Elution gradients, column volumes and flows were determined for operation. The information gathered corresponded to conductivity and absorbance at 280 nm which determine chromatographic profiles. An EXPRESS-ION, Exchanger D column (WHATMAN INTERNATIONAL) using diethylaminoethyl in a cellulose matrix, DEAE-cellulose. The adsorption capacity is 61 mg of protein per ml. The buffer used was Bis-Tris 20 mM pH 7.0 for linking, and the same buffer with NaCl 1 M was used for elution. For hydrophobic interaction chromatography, 1 ml columns of phenyl-sepharose and Butyl-SEPHAROSE FAST FLOW (SIGMA) were used. The union buffer was Bis-Tris or Bis-Tris Propane 20 mM pH 7.0 with $(NH_4)_2SO_4$ 0.7M. To create the gradient, the same buffer lacking ammonium sulfate is used (Andrews, B. A. et al., *Bioseparations,* 1996, 6:303–313). The strategy contemplates high salt concentration and pH between 6.5–8.0. Since the proteins are not well characterized, a resin column substituted with phenyl groups was preferable.

Protein content in UCHT1 conditioned media. Protein was determined by the Bradford method with modifications (Deutscher, M. P. [1990] "Guide to Protein Purification-Methods in enzymology" Academic Press, Inc., 182), using Coomassie Brilliant Blue G-250. BSA (SIGMA) was used for standardization. An ULTRASPEC 3000 spectrophotometer (PHARMACIA BIOTECH) was used. Exceptionally, protein was determined by the bicinconinic acid method, using a Protein assay kit (PIERCE).

Bio Assay of UCHT1 conditioned media fractions. The selection of an adequate bioassay to detect transformation with the various fractions of UCHT1 media collected was desired. The cell lines used were the KGFR cell line, the NRK 52E cell line, and the human nueroblastoma cell line. The KGFR cell line was derived from the mouse fibroblast 3T3 cell line, and transfected with the receptor for EGF. The cells grow attached to surfaces, in media composed of DMEM/F12 (1:1) (SIGMA) supplemented with 10% fetal bovine serum, and passaged with standard trypsinization. The KGFR cell line was used to establish a soft agar and a liquid media assay to test fractions of the UCHT1 conditioned media. The NRK 52E cell line (ATCC:CRL-1571), derived from normal kidney epithelia of a rat (*Rattus norvegicus*). The NRK 52E cell line expresses receptors for EGF and multiplication stimulating activity (MSA), and grows attached to surfaces. NRK 52E cells are not transformed and exhibit contact inhibition in culture, a fundamental property in assays of transformation and malignancy. The cells grow in DMEM/F12 1:1 media (SIGMA) supplemented with 10% fetal bovine serum (FBS). Passages were done with standard trypsinization. Split ratio 1:3–4, with media renewals twice a week. Human neuroblastoma cells derived from an explant of tissue were derived from a biopsy of a patient and subsequently cultured. The cells grow adhered to substrate in DMEM/F12 1:1 media (SIGMA) supplemented with 10% FBS, 10% adult serum and NGF (CALBIOCHEM) 10 ng/ml. They were later adapted to 10% adult serum, 7.5% FBS and 5 ng/ml NGF.

Soft Agar Technique for purification and characterization of UCHT1 proliferation factor. This technique correlates in 90% to transformation, and is faster and less costly than working with animal models such as the Nude mouse to detect tumorogenicity. Cells are grown in soft agar for a week, and colonies are the evidenced with dyes. Cells growing on this environment due so independently of anchoring, which correlated with a transformed phenotype. The protocol for the soft agar technique is as follows: (1) dilute agar 5% 10 times in culture media, to final concentration: 0.5%; (2) add 0.7 ml agar 0.5% to 3.5 cm diameter culture dishes (base); (3) mix 0.2 ml cell suspension (Approx. $3 \times 10^4$ cells/ml) per dish; (4) 0.7 ml agar 0.3% is placed over the base agar, and the dishes are kept in the incubator for 1 week (37° C., 100% humidity, 10% $CO_2$); (5) after 1 week, cells are dyed with p-iodonitrotetrazolium 0.5 mg/ml; and (6) cells are incubated for 24 hours incubation size and number of colonies are estimated.

Precipitation with acetone. Two methods were used for precipitation: (1) with acetone; and (2) with ammonium sulfate. For precipitation with acetone, media lacking serum and kept in UCHT1 conditioned medium for 24 hours was used. Total protein content was assessed with the bicoconinic acid assay. The proceeding begins with the centrifugation of serum free conditioned media at 5,000 rpm for 20 minutes, after which the supernatant is filtered at 0.2 µm porosity. Acetone was later added at −20° C., and precipitate was collected by centrifugation at 10,000 rpm for 30 minutes. The supernatant was collected and more acetone was added. The precipitate was resuspended in 1 ml cold sterile PBS. A second precipitation followed with excess acetone, using 0.1 ml of every PBS fraction and 1.5 ml acetone.

Precipitation with Ammonium sulfate. Serum free, UCHT1 conditioned media was centrifuged at 5,000 rpm for 20 minutes, after which the supernatant was filtered at 0.2 µm porosity. pH was maintained in the range of 7.0–7.5 and temperature at 4° C. at all times. Ammonium sulfate was added and mixed for 30 minutes to equilibrate the solvent with protein. The precipitate was collected after centrifugation at 10,000 rpm for 30 minutes. The supernatant was reutilized for further precipitations, and the final precipitates were resuspended in 200 µl cold sterile buffer.

Adaptation to defined media, serum deprivation. Defined media corresponds to DMEM/F-12, enriched with the supplements listed in Table 2, which are trophic for thyroid cells Scopes, R. [1988] "Protein Purification—Principles and Practice" Springer-Verlag Inc., New York). UCHT1 cells were gradually adapted to defined media using a gradual decrease of the serum content: 12.5% to 9.4%, 6.3%, 3.1% and finally 1.25%. The conditions were kept for two passages in each serum concentration.

TABLE 2

| Media composition per ml | | | |
|---|---|---|---|
| | | | Origin |
| TSH | 10 | mU | bovine |
| Transferrin | 5 | µg | human |
| Insulin | 10 | µg | bovine |
| Somatostatin | 10 | ng | synthetic |
| GlyHisLys | 10 | ng | synthetic |
| Hydrocortisone | 1.00E−08 | M | synthetic |

UCHT1 cells were gradually adapted to defined media using a gradual decrease of the serum content: 12.5% to 9.4%, 6.3%, 3.1% and finally 1.25%. The conditions were maintained for two passages in each serum concentration.

Culture media, solutions. All solutions were prepared in sterile, tridistilled and deionized water. Phosphate buffered saline (PBS) pH 7.4, contained 8.0 g/l NaCl (136.9 mM); 0.2 g/l KCl (2.7 mM); 1.5 g/l NaHPO$_4$ (10.6 mM); 0.2 g/l KH$_2$PO$_4$ (1.5 mM); D solution, pH 7.4 contained 8.0063 g/l NaCl (137 mM); 0.4026 g/l KCl (5.4 mM); 24.1 mg/l Na$_2$HPO$_4$ (0.17 mM); 29.9 mg/l KH$_2$PO$_4$ (0.22 mM); 1.0899 g/l glucose (5.5 mM); 2.0196 g/l (5.9 mM). Trypsin was diluted 0.1% w/v in PBS. Culture media contained DMEM/F-12 supplemented with 1 gr/l bicarbonate and 40 µg/ml gentamicyn if required (Laboratorio Chile, 80 µg/ampoule)

Following are examples which illustrate procedures for practicing the invention. These examples should not be construed as limiting. All percentages are by weight and all solvent mixture proportions are by volume unless otherwise noted.

EXAMPLE 1

Rat Thyroid Cell Line (UCHT1)

A clonal cell line derived from a functional and transplantable rat thyroid tumor was established in continuous monolayer culture by the use of enzymatic dissociation followed by an alternate culture-animal passage procedure (Caviedes, R. and Stanbury J. B., *Endocrinology*, 1976, 99:549–554). Autonomous and transplantable tumors were used as a cell source for cultures (Matovinovic, J. et al., *Cancer Res.*, 1970, 30:540; Matovinovic, J. et al., *Cancer Res.*, 1971, 31:288).

Tumors were developed by implanting thyroid tissue from rats that had been fed on an iodine-deficient diet for 14–18 months into $^{131}$I-thyroidectomized animals on a similar diet. After approximately 9 months, the tumors were transplanted to animals on a regular diet. Well-differentiated follicular and function tumors, which arose 6 months later (second generation), were selected to establish serial cultures.

Cells from several tumors were introduced into monolayer culture through enzymatic dispersion, followed by the alternate culture-animal passage (Buonassisi, B. et al., *Proc. Natl. Acad. Sci.,* 1962, 48:1184). The nutrient mixture Ham's F-10, supplemented with 15% horse serum and 2.5% fetal calf serum, was employed for the establishment of the cell line. As soon as the cells had adapted to these culture conditions, they were transferred to Dulbecco and Freman's modified Eagle Essential medium with the same serum complement. Cultures were grown in Falcon plastic flasks in a humidified atmosphere (air containing 5% $CO_2$) at 37° C. Medium was renewed every 3 days, and the cells subcultured at intervals of 8 days. At confluence, the cells from two Petri dishes were suspended in 0.5 mL of isotonic saline solution and injected subcutaneously into the thigh of each rat (2–3 months old). After approximately 2 months, the tumors were removed, dissociated by enzymatic exposure, and again plated in culture. A clonal line was isolated from one of the tumors, according to the single cell plating technique. Others were kept in primary culture.

After being implanted back into the animal and again plated in culture, epithelial-like cells aggregated and rearranged themselves over the bottoms of dishes in structures resembling cross sections of a normal thyroid gland. The same morphology and growth pattern were maintained after innumerable subcultures and freeze/thawing periods. Cells grew with a population-doubling time of about 24 hours in serum-supplemented synthetic medium. Cell monolayers stained with periodic acid-Schiff (PAS) showed a uniformly epithelial-like morphology; their cytoplasm contained abundant PAS-positive material that was resistant to enzymatic digestion with amylase. Thin-layer chromatography of acid-butanol cell extracts in primary and clonal cultures, followed by a specific and sensitive staining method for iodine compounds, demonstrated the presence of monoiodotyrosine (MIT), diiodotyrosine, and triiodothyronine-thyroxine. In contrast, in similar extracts obtained from a cultured liver cell line, the only iodinated amino acid was MIT. Thus, with regard to the above criteria, this cell line preserved specialized thyroid cell morphology and function. Further details regarding materials and methods utilized, and observations as to culture morphology and hormone detection, can be found in Caviedes, R. and Stanbury J. B., (1976).

EXAMPLE 2

Preparation of UCHT1 Conditioned Medium (UCHT1-CM)

Glass Petri dishes (15 cm diameter) were inoculated with approximately $5 \times 10^5$ mycoplasma free UCHT1 cells (as described in Example 1) in a mixed solution consisting of equal volumes of Ham $F_{12}$ and Dulbecco's modified Eagle's medium ($F_{12}$/D) supplemented with 10% bovine serum, 2.5% fetal bovine serum, 0.015M HEPES (n-2-hydroxyethylpiperazine-N'-2 ethane sulfonic acid) buffer pH 7.2, 50 mg/i streptomycin sulphate and 100 mg/l sodium-penicillin-G, which was used as the basal growing medium (BGM). Cultures were incubated at 36° C., 100% humidity in an incubator with controlled 10% $CO_2$, 90% air atmosphere and total media changes every three days. UCHT1-CM was collected from exponentially growing cultures and harvested from four subsequent culture periods of 24 hours, obtaining a total amount of 80 mL per dish at the end of the four days; the extensive cell detachment after confluence prevents further UCHT1-CM collection. Finally, UCHT1-CM was filtered through 0.2 µm Gelman SUPOR-200 nitrocellulose membranes and stored frozen at −20° C.

EXAMPLE 3

Immortalized Skeletal Muscle Cell Line

A cell line (RCMH) in permanent culture was established from surgically removed adult normal human skeletal muscle by exposure to conditioned media obtained from thyroid cells. Cells proliferated indefinitely but displayed density inhibition of growth while maintaining some differentiated markers. Under certain incubation conditions, cells fused into myotube-like structures, with a concomitant increase in muscle specific proteins, such as human myoglobin, skeletal muscle myosin, desmin and dystrophin, as identified using immunocytochemical procedures. In addition, RCMH cells displayed high affinity receptors for α-bungarotoxin ($B_{max}$=0.7 pmol/mg protein, $K_d$=1.5 nM) and dihydropyridines ($B_{max}$=0.3 pmol/mg protein, $K_d$=0.5 nM for [$^3$H] PN200-110). These values are comparable to those reported for normal muscle cells in primary culture. Patch-clamp studies showed the presence of 42 pS carbachol gated channels and of 5 pS calcium channels (current carried by barium); chloride and potassium channels were also seen. Details regarding establishment of culture, culture conditions, immunocytochemical procedures, binding experiments, and single channel recording carried out on the RCMH cell line, and results, are described in Caviedes, R. et al., *Biochimica et Biophysica Acta,* 1992, 1134:247–255.

EXAMPLE 4

Immortalized Cerebellar Cell Line

Ten Fisher, 6-month-old female rats were injected with $10^6$ UCHT1 cells subcutaneously. After developing a tumor within 3 months, the animals were anesthetized and portions of cerebellar cortex were dissected and placed on watch glasses containing a mixture 1:1 of Eagles modified Dulbecco's and Ham's F12 media (GRAND ISLAND BIOL. Co., NY, U.S.A.) without serum. Cerebellar explants of approximately 1 mm³ were prepared, placed in glass petri dishes and allowed to and grow in the same medium mixture containing 15% bovine, 2.5% fetal bovine serum, 0.015H M Hepes buffer, pH 7.2, plus 50 mg/l streptomycin sulphate, 100 mg/l sodium-penicillin-G and sufficient glucose for a total amount of 6 g/l. Cultured explants were incubated at 36° C., 100% humidity. Clones were isolated from cerebellar established cultures at the 25th passage and after 15 months in vitro. One clone (UCHCC1) was maintained in culture and studied while the others were frozen. The cerebellar cell line UCHCC1 retained a neuronal-like morphology; the addition of dimethylsulfoxide (DMSO) to the culture medium elicited a reproducible morphological "differentiation" event, characterized mainly by process extension. In "differentiated" cells, veratridine significantly increased the update of $^{22}$Na. Such enhanced uptake was blocked by tetrodotoxin (TTX) with a half-maximal inhibitory concentration of 0.9 nM. Binding of an [$^3$H]ethylenediamine derivative of TTX ([$^3$H] en-TTX) to the microsomal fraction prepared from the same DMSO-treated cells, showed a single class of receptors with a maximal binding ($B_{max}$) of a 173 fmol/mg protein and a $K_d$ of 1.1 nM. Thyroid UCHT1 cells and "undifferentiated" (cultured without DMSO) cerebellar cells, did not show significant effects of veratridine on $^{22}$Na-uptake, or [$^3$H]en-TTX binding. The "differentiated" nerve-like properties, induced by appropriate environmental manipulation, demonstrate the usefulness of cerebellar UCHCC1 cells as a model system for the developing central neuron. Further details regarding establishment of culture, culture conditions, sodium flux assays, binding assays with [$^3$H]ethylenediamine-tetrodotoxin ([$^3$H]en-TTX), morphological studies carried out on the UCHCC1 cell line, and results, are described in Caviedes R. et al. *Brain Res.*, 1986, 365:259–268.

EXAMPLE 5

Immortalized Myocardial Cell Line

A cell line (RCVC) in permanent culture was developed from adult rat ventricular cells; transformation was attained by incubation with conditioned media from the UCHT1 rat thyroid cell line. Specifically, ventricular cavities were removed from the hearts of decapitated Fisher 344 normal male rats and removed of fat and mesenchymal envelopes, and finely minced. The myocardial explants of approximately 1 mm$^3$ were prepared, seeded onto 10 cm diameter glass dishes and allowed to attach and grow in BGM plus 20% UCHT1 conditioned medium (UCHT1-CM). Approximately 25% of ventricular explants attached, started an outgrowth in two weeks, and attained confluence in 40 days. Initial outgrowth were split by trypsinization and EDTA, and sorted out using the "selective serial passage" method. Three successive passages followed by the corresponding preplating period of 24 hours were carried out to select the slowest attaching cells. Cultures were incubated for periods devoid of cysteine, glutamine, and sera to eliminate fibroblasts. Myoblast enriched cultures were subcultured by trypsinization and diluted 1:2 to 1:10, depending on proliferative capacity. After 3 months of continuous propagation in culture, UCHT1-CM was removed from BGM without significant effect on cell growth parameters.

Immortalized ventricular cells having a doubling time of 20 hours, contact inhibition of growth, and which display some muscle markers such as a high glycogen content and positive immunoreaction for myoglobin, α-sarcomeric actin, α-actinin and desmin were obtained. A microsomal fraction from these cells was shown to bind $^3$H-nitrendipine with a maximal capacity of 295 fmol/mg protein and an equilibrium dissociation constant of 0.7 nM. Nifedipine-sensitive $^{45}$Ca$^{2+}$ influx was evident in partially depolarized cells (40 mM K$^-$ in the incubation medium). An equivalent influx, induced by the calcium channel agonist BAYK-8644 and CGP-28392, was obtained in normally polarized cells.

Patch clamp studies show slow inward currents that can be completely blocked by 5 μM nifedipine; cells were induced to further differentiation by culturing in a hormone supplemented medium for 30 days. Under this condition, fast, inactivating inward currents and a large outward current became apparent. After 40–60 days, the cells exhibit La$^{3-}$-sensitive fast and slow inactivating inward currents that resemble T and L-type Ca$^{2+}$ currents. Further details regarding establishment of the RCVC cell line, culture conditions, immunocytochemical studies, $^3$H-Nitrendipine binding studies, $^{45}$Ca$^{2-}$ flux experiments, patch clamp methodologies, and results, are described in Caviedes, P. et al., *Mol. Cell. Cardiol.*, 1993, 25:829–845.

EXAMPLE 6

Impaired Cell Lines as Models of Disease

Cells proliferated according to the methods of the subject invention can have a naturally occurring or induced pathological defect, such that the cells provide an in vitro model of disease. Thus, mutant, diseased, or otherwise impaired cells can be proliferated for drug screening for that particular disease. For example, pathological tissue has been transformed using UCHT1 conditioned medium, producing cell lines from skeletal muscle of patients bearing Duchenne muscular dystrophy, pancreatic ducts of patients with cystic fibrosis, and from nervous tissue of a murine model of human Down syndrome and Alzheimer's disease.

Knowledge of neuronal dysfunction in Human trisomy 21 (Down's syndrome) is critical for understanding of the mechanisms that give rise to nervous system impairment. Cholinergic function is one of the most compromised in Alzheimer's disease and Down syndrome, two conditions that demonstrate similar pathologies (Caviedes, P. et al., *Brain Res.*, 1990, 510:229–236) and altered choline transport. The establishment of stable, in vitro models of the nervous system would provide an important tool to rapidly and accurately address these problems. Therefore, a cell line proliferated according to the methods of the subject invention can be obtained having similar neurotransmitter dysfunction mechanisms as the originating tissues, and which would serve as a model to study potential therapies and/or further alterations of the cell function.

A cell line (CTb) from a T16 trisomic mouse continuously cultured using the UCHT1 rat thyroid cell line has been established (Allen, D. D. et al., *Euro. J. Neurosci.*, 2000, 12:3259–3264), which can be used as an in vitro model for Down syndrome. Trisomic 16 and normal fetuses were obtained by breeding double heterozygous (Rb 2H/RB 32 Lub) males with normal C5B7BL females. Pregnant females were anesthetized and killed after 12–16 days of gestation. The fetuses were placed in phosphate buffered saline (PBS) and the trisomic fetuses were identified by their characteristic massive edema. Whole brains from trisomic fetuses were removed and meninges were withdrawn, and the cerebral cortex was carefully dissected. The tissues were sliced and suspended in 3 mL of PBS containing 0.12% (w/v) of trypsin (SIGMA) and incubated for 30 minutes at 37° C. The trypsin reaction was stopped by adding an equal volume of plating medium, consisting of DMEM/Ham $F_{12}$ nutrient mixture (1:1) (SIMA) modified to contain 6 g/l glucose, 10% bovine serum, 10% fetal bovine serum, 100 U/mL penicillin, 100 μg/mL streptomycin (SIGMA). The suspension was centrifuged and the pellet was resuspended in 2 mL plating medium. The tissue was dissociated by passages through a fire-polished Pasteure pipette, and the cells were then plated in a collagen-coated (CALBIOCHEM) culture dish at a density of 40,000/cm$^2$. At the time of seeding, the plating medium was supplemented with 10% (v/v) of UCHT1 conditioned medium. After 24 hours, the initial plating medium was replaced by feeding medium consisting of DMEM/Ham $F_{12}$ nutrient mixture (1:1) modified to contain 6 g/l glucose, 10% bovine serum, 2.5% fetal bovine serum, 100 U/mL penicillin, 100 μg/mL streptomycin, and 10% UCHT1 conditioned medium. The cultures were kept in an incubator at 37° C. with 100% humidity and an atmosphere of 10% CO$_2$ and were monitored routinely for the appearance of transformation foci or morphological changes, which became evident after variable periods of time (7–8 months) and signaled the establishment of cell lines CNh (derived from normal cortex)

and CTb (derived from trisomic cortex). Further details regarding the establishment and characterization of the CTb trisomic cell line are described below and in Allen, D. D. et al. (2000) and Cardenas A. M. et al., *Neuroreport*, 1999, 10(2): 363–369. Normal and trisomy 16 spinal cord cell lines and dorsal root ganglion cell lines have also been produced.

A human muscle cell line (RCDMD) was established from a Duchenne muscular dystrophy patient by culturing explants in the presence of UCHT1 conditioned medium. The cell line has had over thirty passages and has recently been cloned. The mother cell line is immunohistochemically positive for desmin, myoglobin, skeletal myosine, and a actinin, and is negative for dystrophin. Further details regarding establishment characterization of the RCDMD cell line are described in Caviedes, P. et al., *Muscle & Nerve*, 1994, 17:1021–1028 and Liberona, J. L. et al., *Muscle & Nerve*, 1998, 21:902–909.

EXAMPLE 7

Miscellaneous Immortalized Cell Lines from Rat, Mouse, Bovine, and Human Sources Two rat cell lines (RCHT-1 and RCHT-2) have been established by culturing explants from the hypothalamus of Fisher 344 rats in the presence of UCHT1 conditioned medium. Markers detected by immunohistochemistry in cell perikarya (% of positive cells) are presented. Values are those obtained from non-differentiated cells. LHRH (+): 10%; tetanus toxin (+): 50–60%; neurophysin: 1%; ACTH: 1%; α MSH: 1%; β endorphin: 1%; somatostatin: 1%; methenkephalin: 0.5%; TRH: 0.5%; vasopressin: 0.1%; oxytocin: 0.1%; tyrosine hydroxilase: 0.1%; GAD: 0.1%; CRH (−); GFAP (−); S100 (−); NSE (−); N-epinephrine uptake: present; norepinephrine (by HPLC): >10 ng/mg protein; and dopamine (by HPLC): 13 ng/mg protein.

A rat atriocardiocyte cell line (RCAC) has been established by culturing explants in the presence of UCHT1 conditioned medium.

Several cell lines have been established from the nervous system of normal and trisomy 16 fetal mice by culturing explants in the presence of UCHT1 conditioned medium. As described above, the latter is considered an animal model of human trisomy 21 (Down Syndrome) and Alzheimer's disease. The murine cell lines originated from the cerebral cortex, hippocampus, spinal cord, and dorsal root ganglia of both normal and trisomic subjects. Cortical cell lines CNH (normal) and CTb (trisomic) immunohistochemically possess neuronal markers (NF, NSE, synaptophysin, MAP-2, etc.) and lack glial markers (GFAP, S-100). These murine neural cell lines respond to glutamatergic (glutamate, NMDA, AMPA, and kainite) and cholinergic (nicotine) stimuli with increase in intracellular $Ca^{2+}$. The CTb cell line expresses large intracellular vacuolized deposits of amyloid, evidenced by both Congo Red staining and immunohistochemistry. Further details regarding the establishment and characterization of these immortalized murine cell lines are described in Cardenas A. M. et al., (1999); Allen, D. D. et al. (2000).

A bovine corneal endothelial cell line has been established by culturing explants in the presence of UCHT1 conditioned medium. The immortalized cell line is immunohistochemically positive for Von Willebrand Factor and PECAM. The cells develop tube like structures when cultured on MATRI-GEL.

A human ovarian granulose cell line was established by culturing explants in the presence of UCHT1 conditioned medium. The immortalized cells produce estrogen and progesterone at basal levels, and respond to FSH and LH with increments in the production of the former steroidal hormones.

A human thyroid cell line was established by culturing explants in the presence of UCHT1 conditioned medium. The immortalized thyroid cells produce thyroglobulin and incorporate tritiated iodine.

EXAMPLE 8

Immortalized RCSN-3 Cell Line and Transplantation into Rat Striatum

Primary cultures of the RCSN-3 cell line, derived from the substantia nigra of an adult rat, were grown in the presence of UCHT1 conditioned media. The RCSN-3 cell line was grown on monolayers, with a doubling time of 52 hours, a plating efficiency of 21% and a saturation density of 410,000 cells/cm, when kept in feeding medium. FIGS. 2A–2F show that undifferentiated RCSN cells tend to exhibit an epithelial like morphology, with short or no processes and a more acidophylic cytoplasm. After differentiation, cell proliferation is greatly reduced, and the RCSN cells develop processes and establish contact with neighboring cells. The presence of melanin was evidenced with the ferrous ion capture technique, demonstrating a homogenous distribution of the pigment in the cytoplasm, with faint labeling in undifferentiated stages and a substantial increase upon differentiation.

Immunohistochemical characterization demonstrated that RCSN cells express neuronal traits, evidenced by the positive immunolabelling for NSE, synaptophysin and MAP-2. NSE and synaptophysin show a fine granular pattern evenly distributed in the cytoplasm, as shown in FIGS. 3A–3H. Synaptophysin is especially intense at the zone of cell-cell interaction. MAP-2 shows a fibrillary pattern of labeling, surrounding vacuole-like cytoplasmic structures. Neurofilament 200 kD labeled differentiated cells homogenously, and tetanus toxin is present in the cell membrane in a patch-like distribution. Functional neuronal markers are shown in FIGS. 4A and 4B, which present immunohistochemical staining for tyrosine hydroxylase. The labeling is slightly less intense in non-differentiated cells, and the label is distributed in the entire cytoplasm following a granular pattern. The presence of catecholamines is also clear from the micrographs presented in FIGS. 4C and 4D, with a cytoplasmic distribution. Glial markers GFAP and S100 were negative in both control and differentiated conditions. When differentiated, up to 40% of Fluo-3 loaded RCSN cells responded with increases in $Ca^{2+}$ when stimulated externally with 200 μm glutamate, and even more intensely when using simultaneous depolarizing conditions (70 mM $K^+$), a situation depicted in FIG. 5. Of 16 cells explored, the $Ca^{2+}$ signal peaks after one second of stimulation, and returns to basal level between 30–40 seconds after the peak. These experiments show that the RCSN-3 clonal cell line retains general properties of neuronal tissue, and possesses specific characteristics of the SN, such as the presence of tyrosine hydroxylase, DOPA decarboxylase, and catecholamines.

Figure 6A:
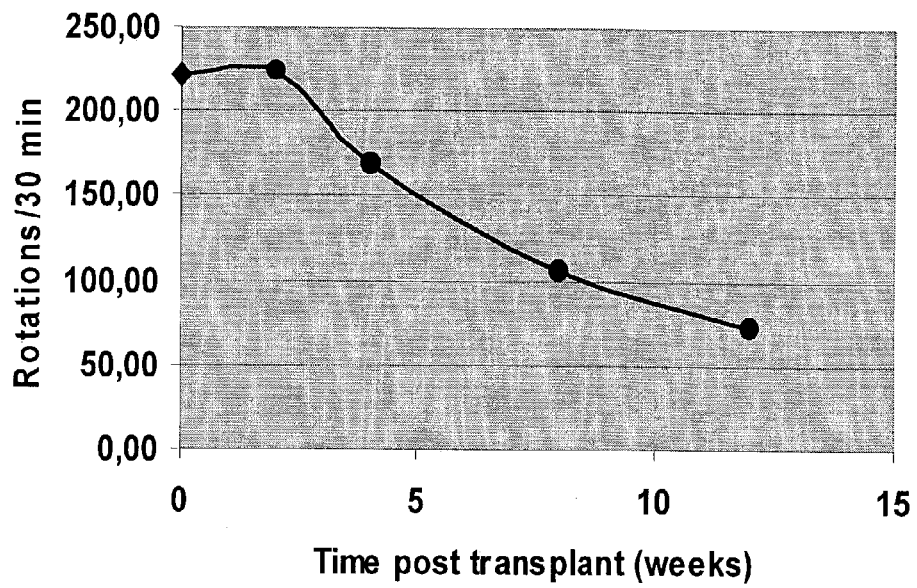
FIGS. 6A and 6B show graphs representing patterns of decrease in the rate of rotation after transplant of RCSN-3 cells into the striatum of 6 hydroxy dopamine (6 OHDA)-lesioned rats.
Figure 6B:
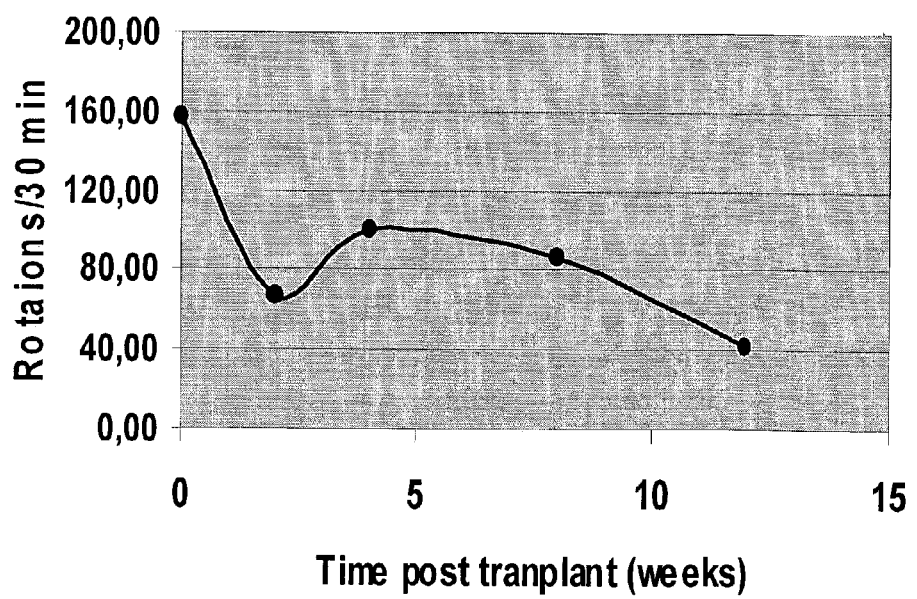

Suspensions of RCSN cells were transplanted into the striatum of rats with 6-OH dopamine-induced lesions of the substantia nigra. FIGS. 6A and 6B show typical patterns in the evolution of the rotational behavior after transplantation, one of which is characterized by a smooth, decreasing exponential-type curve, which levels off after 12 weeks at approximately 25% of the initial rotation rate, as shown in FIG. 6A. Another pattern involves a greater drop in rotations 2 weeks after transplantation, followed by an increase and later a sustained decrease in the rate of rotation to again plateau after 12 weeks, as shown in FIG. 6B. At 16 weeks, the rats were sacrificed, and sections of the striatum were taken and immunohistochemically strained with TH and DOPA decaroxylase antibodies. As shown in FIGS. 7A–7C, cells staining positively for both markers are present in the striatum, showing intense labeling and neurite formation.

As described above, the RCSN-3 cell line induces a sustained and progressive reduction in the rotational behavior of 6-OH dopamine-lesioned rats (75% of the initial rotation values after 16 weeks post implant). No previous in vitro differentiation agents were utilized in these transplantation experiments. This may prove a practical asset, as the cells either have enough dopaminergic function at the time of inoculation, or the in vivo microenvironment in the striatum may be enough to sustain or induce a differentiated phenotype in the RCSN-3 line.

EXAMPLE 9

Immortalized RCSN-3 Cell Line in Hemiparkinson Model

Five Fisher 344 rats with weights between 180 and 200 g. were used (Group A: control (n=1), no lesion or transplant; Group B: control lesion (n=1), lesioned rat, no transplant; Group C: experimental group (n=3), lesioned and transplanted rats). Animals were fed similar ad libitum diets and water. Both transplant and lesion procedures were made under general anesthesia with ketamine and using a David Kopf stereotome. In order to induce the parkinsonian model, a estereotaxic lesion with 8 microg of 6-OHDA in 4 microl of saline solution was injected in the ventral tegmental area that contains the ascending mesoestriatal dopaminergic pathway without jeopardizing the neuronal bodies. The coordinates were 4.4 mm AP, 1.2 mm lateral with respect to bregma and 7.8 mm vertical with respect to the surface of the brain. The injections were made with 50 microl Hamilton syringes. This lesion denervates the areas with dopaminergic inervation of the ipsilateral striatum (Urgenstedt and Herrera-Marschitz, 1981). The 6-OHDA causes the death of dopaminergic neurons of the substantia nigra and therefore the interruption of the nigroestriatal pathway.

In the experimental group, after 8 weeks post lesion, a total of 6 implants of RCSN-3 cell suspensions were made at different depths in the striatum ipsilateral to the lesion, in order to restore the nigroestriatal circuit locally. After 6 weeks, the rats were sacrificed to carry out the morphologic evaluation. The rats were anesthetized with ether and perfused via ventricule with a PBS solution for 10 minutes approximately, to obtain a better fixation and clean the sample of red blood cells. Later, postfixation was carried out in two stages: First, the complete brain was fixed during 4 days, and a second fixation of the tissue sample to analyze (corresponding to the SN and striatum) for a minimum of 7 days. 25 microns thick frozen sections were made in a criostat at –20° C. The sections were collected in 0.05%sodium azide in PBS.

The immunoenzymatic technique used was the detection of the enzyme tyrosine-hydroxilase. The sections obtained were washed with PBS and the blockade of endogenous peroxidase was performed with hydrogen peroxide diluted to 3% in PBS at saturating concentrations. Washing with PBS was repeated twice and the block of non-specific labeling was carried out with BSA 1%, sodium azide 0.05%, Triton X100 1% in PBS during 60 minutes. Sections were then incubated without washing in primary antibody 1:2500 (MONOCLONAL ANTI-TYROSINE HYDROXYLASE, CLONE TH-2) at 4° C. for 12 hours. The sections were then washed with BSA 1% in PBS twice (all the subsequent washes were made with the same solution) and incubated with secondary antibody 1:100 (ANTI-MOUSE INMUNOGLOBULINS, Biotin conjugate) for 60 minutes. Three 10 min washes were made and three sections were incubated with the Avidine-HRP complex 1:100 (EXTRAVIDIN Peroxidase conjugate 0.5 mg/ml) for 60 minutes and a second sequence of three washes of 10 minutes each was performed. The samples were incubated in chromogen DAB (3.3 diaminobenzidine), for 3 to 5 minutes, were washed twice, mounted and covered for later analysis at the microscope.

Figure 8:
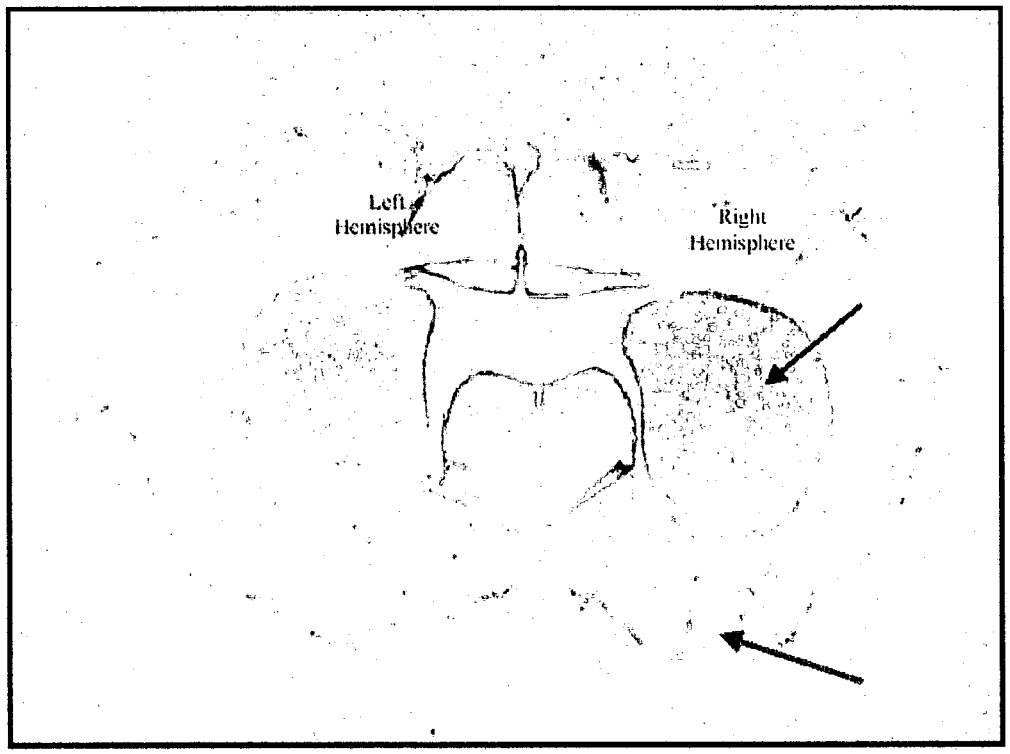
FIG. 8 shows a panoramic view of a brain section of a control rat without injury (lesion) or transplant of RCSN-3 cells. Strong brown colored zones correspond to TH-positive ($TH^+$) cells. The normal rat displays symmetry in the labeling of both hemispheres, where the striatum (top arrow) and the substantia nigra (SN) (lower arrow) exhibit TH.

The analysis of the histological sections positive for TH shows the cerebral areas that express this enzyme with a strong brown color label in the cytoplasm and axonic terminals of $TH^+$ neurons (FIG. 8). In the sections, certain areas with a tenuous positive coloration due to the presence of certain degree of background can be appreciated, due to proteins that bind to the antibody non specifically, that are not comparable with the TH-positive areas where a strong labelling is evident in the zone of implants.

Figure 9:
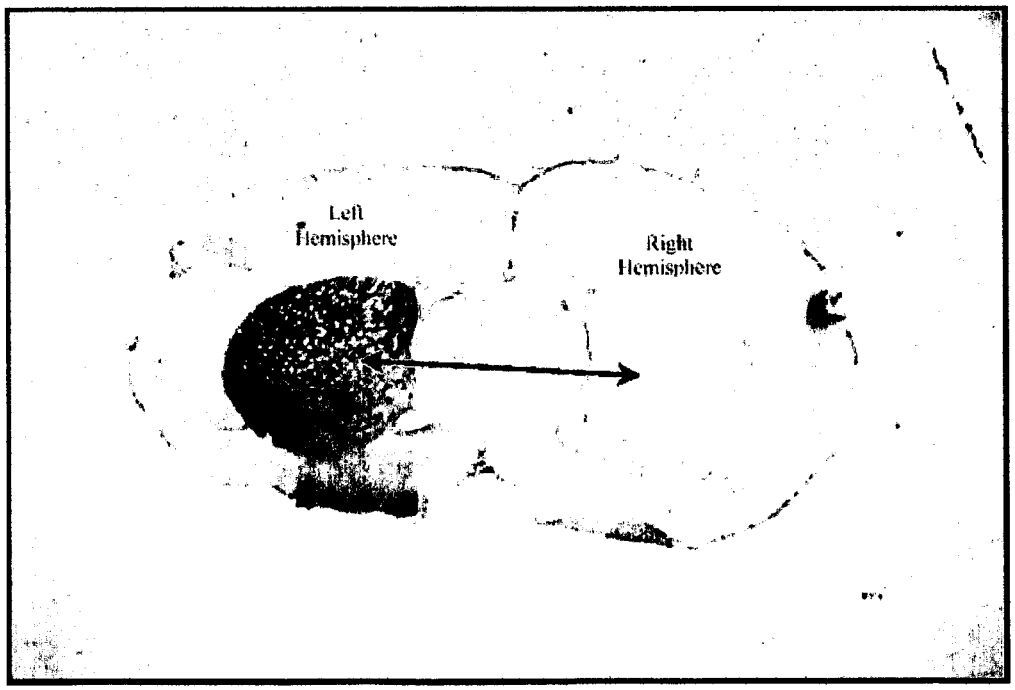
FIG. 9 shows a panoramic view of a brain section of a control rat with a 6 hydroxy dopamine (6-OHDA)-induced lesion of the ventral tegmental area, without transplant of RCSN-3 cells. A marked difference in labeling is observed in the region of the striatum (black arrow). This figure confirms the destruction of dopaminergic terminals in the right striatum that proceeded from the nigrostriatal pathway.

When observing sections of the normal rats (control group A, FIG. 8) a clear symmetry in the labelling is observed, with labelling in striatal areas. When compared with the sections of the lesioned rats (lesion control group of B, FIG. 9) they display a noticeable asymmetry in the labelling pattern, lacking the characteristic $TH^+$ labelling in the 6 OH dopamine-lesioned side, reflecting the absence of dopaminergic terminals.

Figure 10:
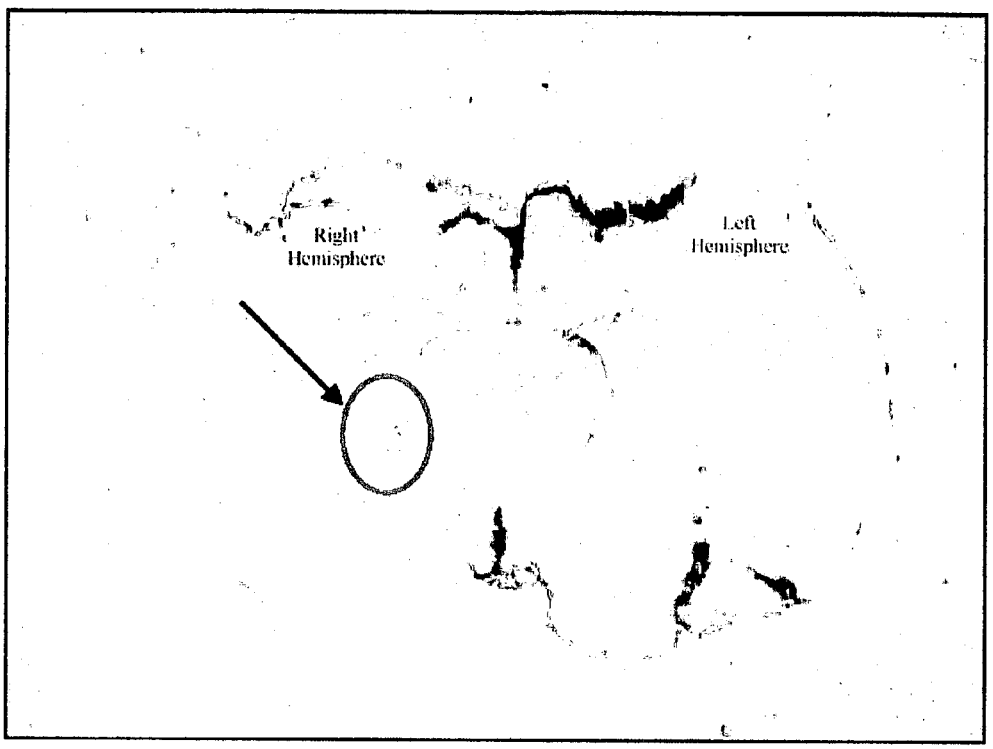
FIG. 10 shows a panoramic view of a section of the rat brain in the experimental group (i.e., 6-OHDA-induced lesion, and transplanted with RCSN-3 cells). A $TH^+$ zone (arrow, circle) corresponds to an accumulation of transplanted RCSN-3 cells, near the lateral ventricle (circle).

At 4× magnification, in the sections of the experimental group (FIG. 10), a $TH^+$ localized region is evident, specially when comparing with the rest of the striatum. When analyzing the lesioned area, small zones of dark brown color are evident, in special in proximity to the lateral ventricles, that correspond to the viable transplanted cells.

Figure 11:
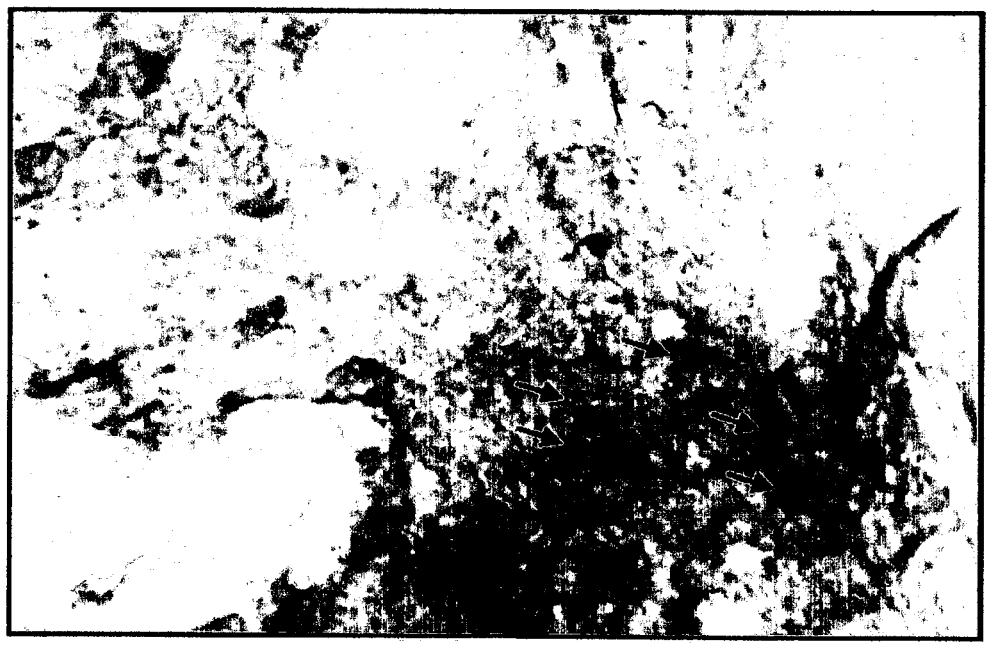
FIG. 11 shows a photomicrograph of the implant zone within the brain of a lesioned rat transplanted with RCSN-3 cells. $TH^+$ reaction is observed. Arrows indicate the accumulation of $TH^+$ cells surrounding the area of the needle tract (40× magnification). The neuronal density of implants does not permit distinction of individual neurons clearly.

At greater magnification (20×) (FIG. 11) in this zone, an accumulation of TH+ structures can be observed in the zone of implants, associated with the needle tract and near the ventricles, where theoretically the restoration of dopaminergic interaction with striatum is most necessary.

Figure 12:
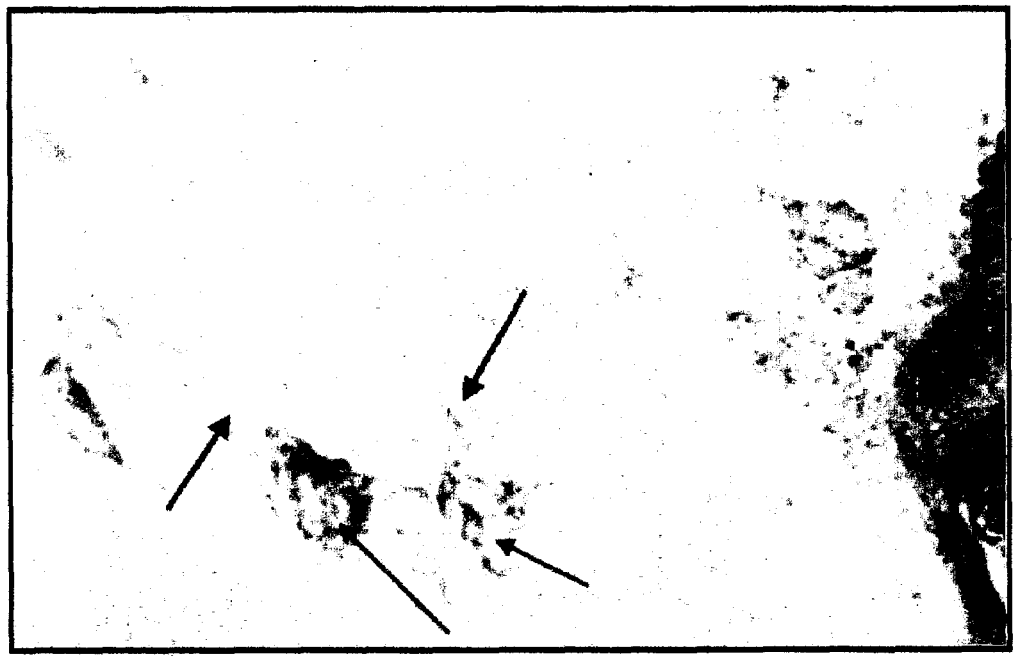
FIG. 12 shows a photomicrograph of implanted RCSN-3 cells with neuronal morphology in the striatum of a lesioned recipient rat (100× magnification). Note the presence of process (thicker, upper arrows) extending from the somas (thin, lower arrows).
Figure 13:
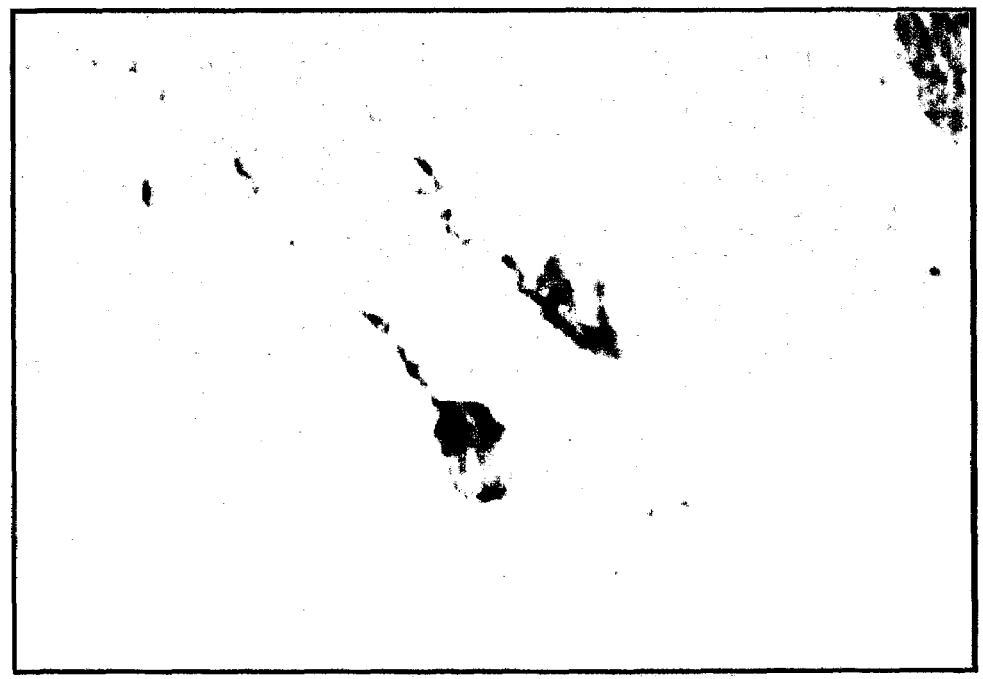
FIG. 13 shows a photomicrograph of implanted RCSN-3 cells in the striatum of a lesioned recipient rat (100× magnification). Note the existence of a significant number of processes oriented predominantly toward the striatum.
Figure 14:
FIG. 14 shows a photomicrograph of implanted RCSN-3 cells within the striatum of a lesioned recipient rat (100× magnification). The presence of $TH^+$ somas single lower grey arrow and processes (four upper black arrows).
Figure 15A:
FIGS. 15A–15E show lower magnification photomicrographs of rat striatum.
Figure 15B:
Figure 15C:
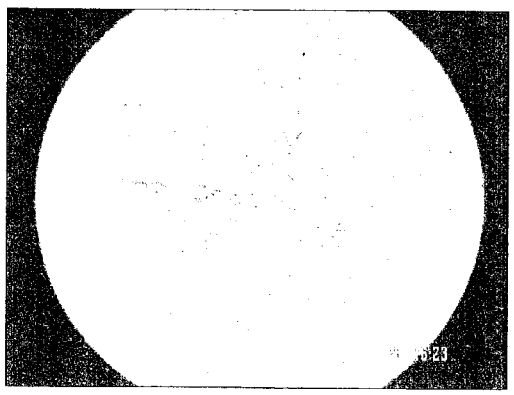
Figure 15D:
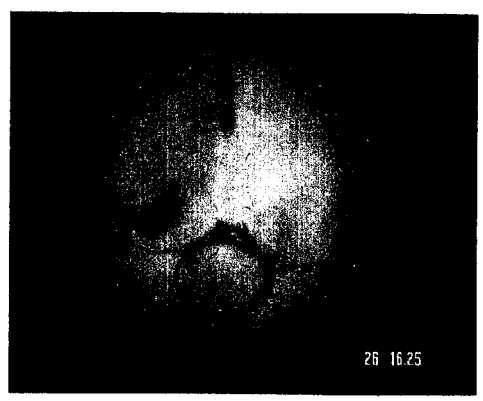
Figure 15E:
Figure 16A:
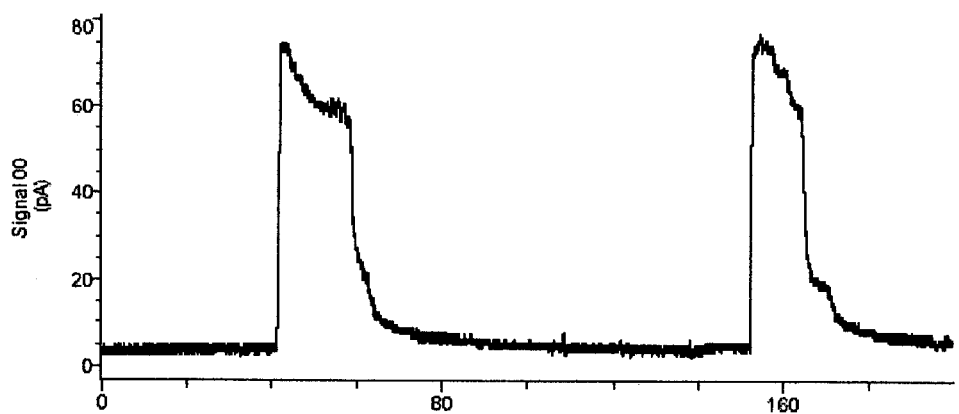
FIGS. 16A–16C show amperimetric detection of dopamine.
Figure 16B:
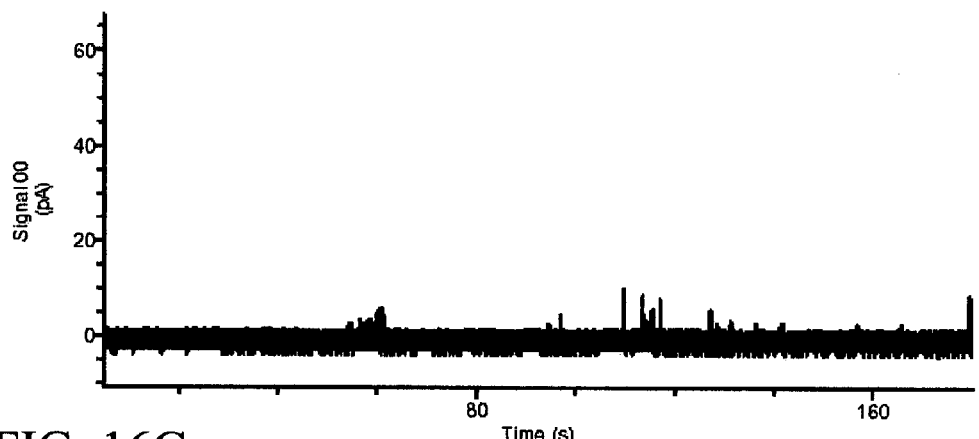
Figure 16C:
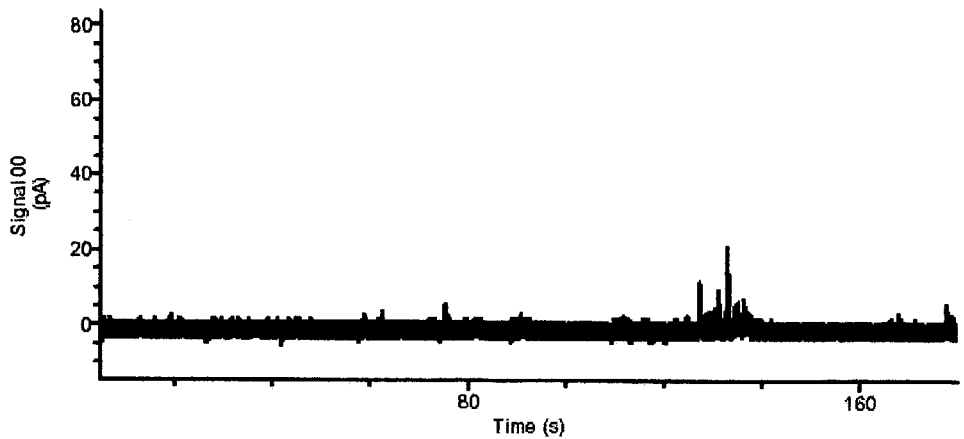
Figure 17C:
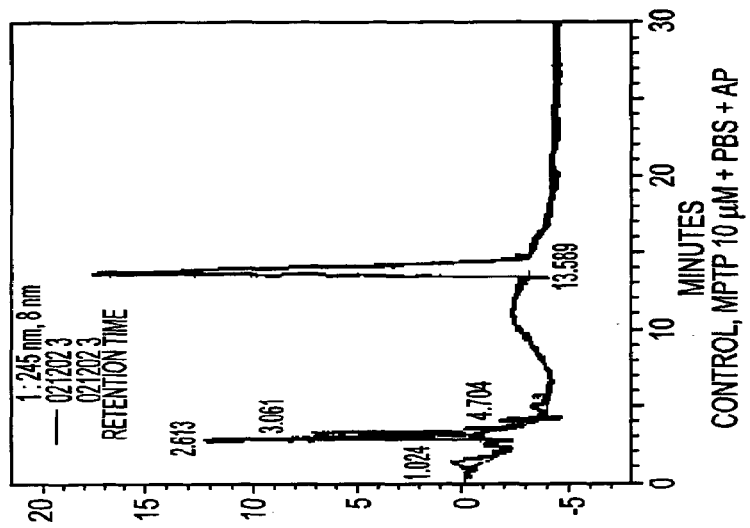
FIGS. 17A–17D show controls for the evaluation of 1-methyl-4-phenylpyridinium ($MPP^+$) production by cell lysates incubated with 1-methyl-4-phenyl-1,2,3,6-tetrahydropyridine (MPTP).
Figure 17B:
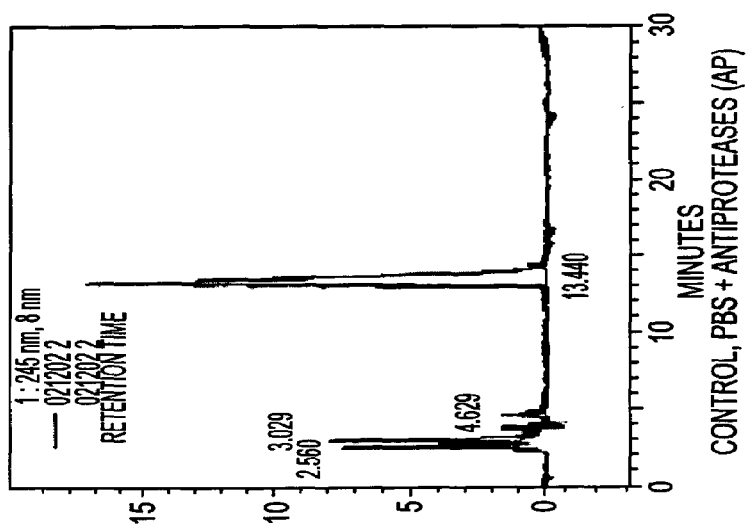
Figure 17A:
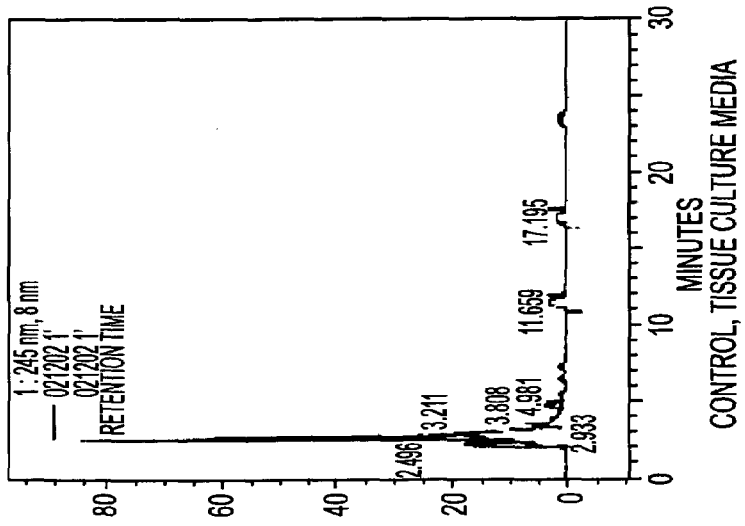
Figure 17D:
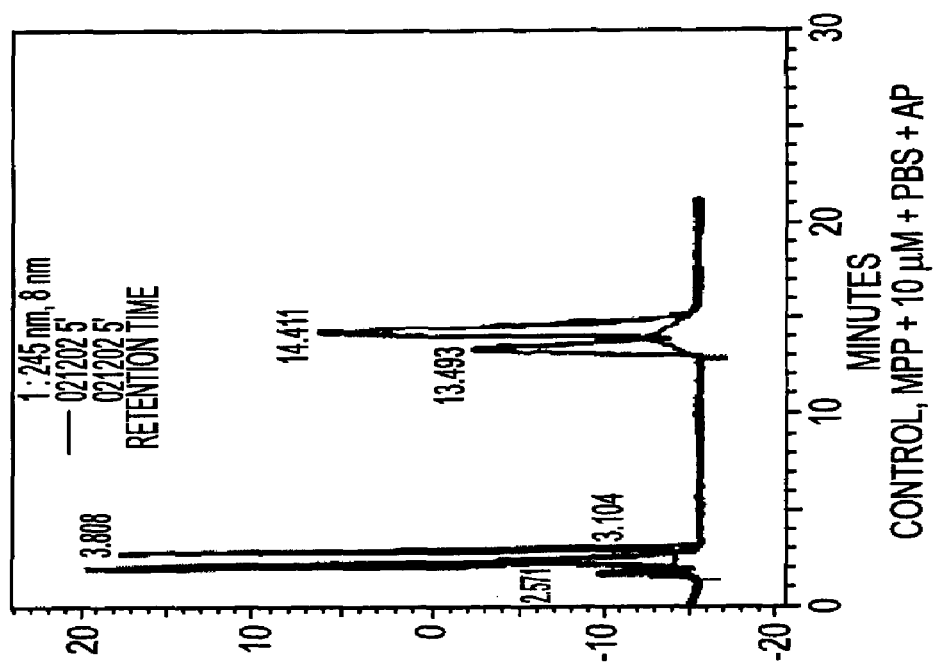

Through further magnification (40×; 100×) and with greater detail (FIGS. 12, 13, and 14) it is possible to observe that these $TH^+$ zones correspond to cells with a morphology that exhibits a body and processes of a neuronal type. These processes, which present some ramifications, follow a direction towards the striatum. In addition, these cells are not isolated, they appear in small groups, associated to the zones of greater labelling (where it is not possible to recognize individual cells, due to high cell density and strong labelling).

Positive TH labelling confirms the existence of dopaminergic neurons in different areas from the brain, since such cells express within their enzymatic machinery this rate limiting enzyme that converts of tyrosine into L-Dopa, which in turn undergoes decarboxilation to become dopamine (Adams, R. et al. (1999) Principios de Neurologia. Editorial McGraw-Hill Interamericana, México DC, 6th Edition, pp. 925–931). In addition, according to our results, a strong $TH^+$ reaction is observed in zones rich in dopaminergic terminals such as the substantia nigra and striatum, which confirms that $TH^+$ neurons (terminals) are indeed present given their morphologic location, since the nigroestriatal pathwaye acts mainly as a modulator of the basal ganglia by dopamine (Kandel, E. et al., (2000) Principles of Neural Science, Editorial McGraw-Hill, USA, 4th edition, Chapter 15, Neurotransmitters, pp. 280–297).

The sections studied in control rats show symmetry in labelling between both striatum, since they have both nigroestriatal pathways intact. Conversely, lesioned injured rats display a unilateral neuronal degeneration of the pathway, losing all connections between the substantia nigra and the striatum, which is confirmed in the sections cuts of the lesioned rats.

In this study, the presence of implanted dopaminergic RCSN-3 neurons was comfirmed, as evidenced by the presence of discrete regions of $TH^+$ cells in the striatum the lesioned side limited to the lateral wall of the lateral ventricle, and which present the same morphology that those neurons that are adhacent to the space left by the veedle tract.

The present work is the result of the experience of implants of immortalized cells of adult substantia nigra in an animal hemiparkinsonian model (Cenci, M.A. et al, *Nature Reviews Neuroscience*, July 2002, 3(7):574–9), that allows us to envision a possible development of definitive therapies for Parkinson's disease, which can replace present pharmacological therapies (Rascol, O., *J. Neurology*, April 2000, 247(Suppl. 2):II 51-7; Weiner, W., *Archives of Neurology*, March 2000, 57:408). The model of implants of immortalized cells presents advantages over other experimental and applied techniques in medicine for the surgical treatment of the disease. Firstly, the immortalized cells derived from dedifferentiated adult tissue which does not involve ethical conflicts like transplants of embryonic cells (Jong-Hoon, K. et al., *Nature*, Jul. 4, 2002, 418:50–56; Björklund, L., et al., *PNAS*, February 2002, 99:2344–2349; Freed, C., *PNAS*, February 2002, 99:1755–1757), fetal (Blanco, L. et al., *Reviews Neurology*, March 1998, 26(151):361–5; Vogel, G., *Science*, March 2001, 291:2060–2061), or from stem cells (McKay, R., *Nature*, Jul. 27, 2000, 406:361–364; Mc Laren, A., *Nature*, Nov. 1, 2001, 414:129–131), implied in the use of embryos. Secondly, cells immortalized from the host would not require immunosuppression as the present treatments (Lindvall, O. and P. Hagell, *Clin. Chem. Lab. Med.*, April 2001, 39(4): 356–61; Dunnett, S. et al., *Nature Reviews Neuroscience*, 2002, 2:365–69; Jankovic, J., *Archives of Neurology*, July 1999, 56:785; Fischbach, G. and G. McKhann, *N. Engl. J. Med*, March 2001, 344:763–765), therefore diminishing the risks associated with this type of therapeutic approach.

In summary, with the present study, the presence of RCSN3 neurons in the striatum of transplanted rats is confirmed, as evidenced by $TH^+$ staining. In addition, the presence of cytoplasmic processes could be the morphologic base of the reestablishment of the synaptic connections with the interneurons of the striatum that would explain the improvement in the rotational conduct induced by apomofina in hemiparkinsoniano model of rat.

EXAMPLE 10

Amperimetric Detection of Dopamine Secretion in RCSN-3 Cells

Electrochemical detection of catecholamine release was performed as described previously (Kawagoe, K. T. et al., *Analytical Chemistry*, 1991, 63:1589–1594). Briefly, carbon fiber sensors were constructed by inserting single carbon fibers (of 10 μm diameter) into pulled glass capillaries. The carbon fiber electrode was then coated with a thin and uniform isolation film using the technique of anodic electrophoretic deposition of paint. The polymer film was then heat cured. Before each experiment, the electrodes were polished at a 45 degree angle on a micropipette beveling wheel (NARISHIGE, Tokyo, Japan). Electrochemical currents were amplified with a List EPC-5 patch-clamp amplifier. The potential of the carbon fiber electrode was set at +650 mV. The current signal was filtered at 10 kHz through a low pass filter, stored, and analyzed with an IBM PC-compatible computer.

Cells were cultured in 1 cm diameter coverslips using either growth media (F 10 supplemented in 10% adult bovine serum, 2.5% fetal bovine serum, 100 U/ml penicillin and 100 μg/ml), or differentiation media, where adult serum was reduced to 2% and fetal serum was omitted.

Figure 18C:
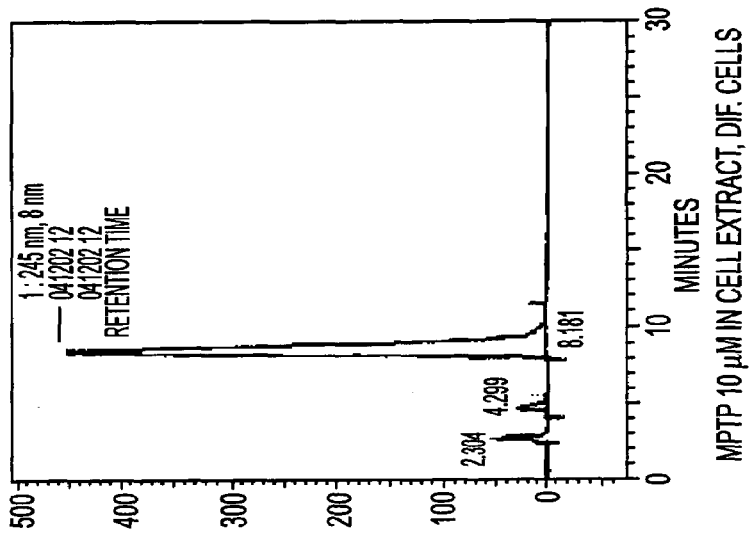
FIGS. 18A–18C show the evaluation of $MPP^+$ production by RCSN-3 cell (differentiated and non-differentiated) lysates incubated with MPTP.
Figure 18B:
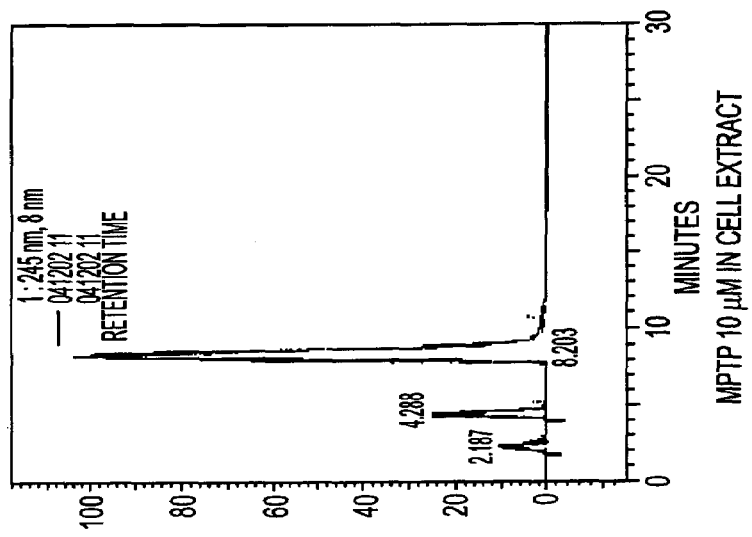
Figure 18A:
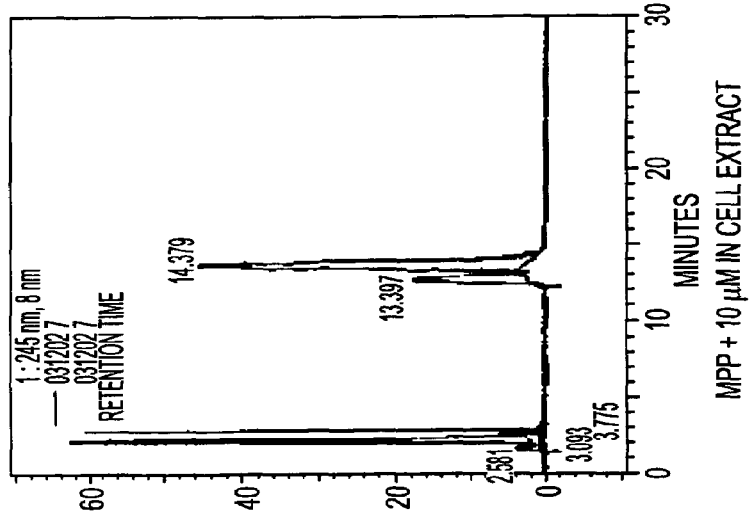

To verify if RCSN-3 cells can produce $MPP^+$ from MPTP, lisates of RCSN-3 cells (differentiated and non-differentiated) were incubated with MPTP. Differentiation was induced by culturing in F10 media+2% adult bovine serum for one week. Non-differentiated conditions were attained with F10 media+10% adult bovine serum and 2.5% fetal bovine serum. Lisate buffer was PBS with 50 μM PMSF and a protease inhibiting cocktail (leupeptin, pepstatine, chemostatin). Samples were incubated with MPTP and $MPP^+$ for 15 min. at 37° C. HPLC studies were carried out in a SHIMADZU HPLC with reverse osmosis, reading at 245 nm. Results are shown in FIGS. 16A–C, FIGS. 17A–D, and FIGS. 18A–C. FIGS. 18A–C demonstrate no production of $MPP^+$ (absence of peak at 14.4 min.) when cell extracts are incubated with MPTP, suggesting that MAO B activity is not present in these cells.

EXPERIMENT 11

Apoptosis in the RCSN-3 Cell Line

Figure 20A:
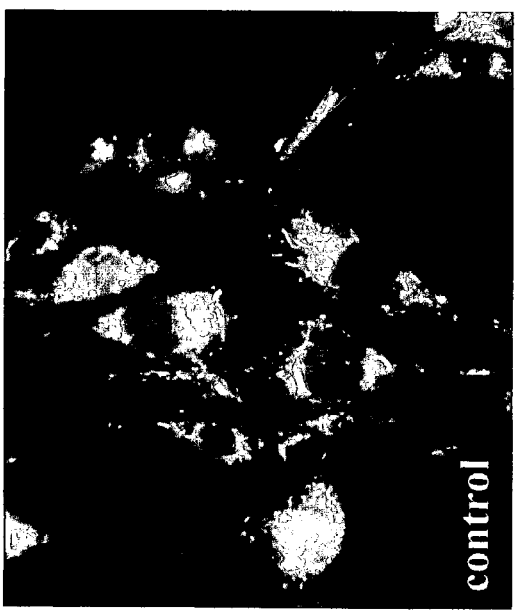
FIGS. 20A–20C show mitochondrial membrane potentials of RCSN-3 cells as detected with potassium tetrachloride or tetraethylbenzimidazolilcarbocianine (JC-1).
Figure 20B:
Figure 20C:
Figure 21B:
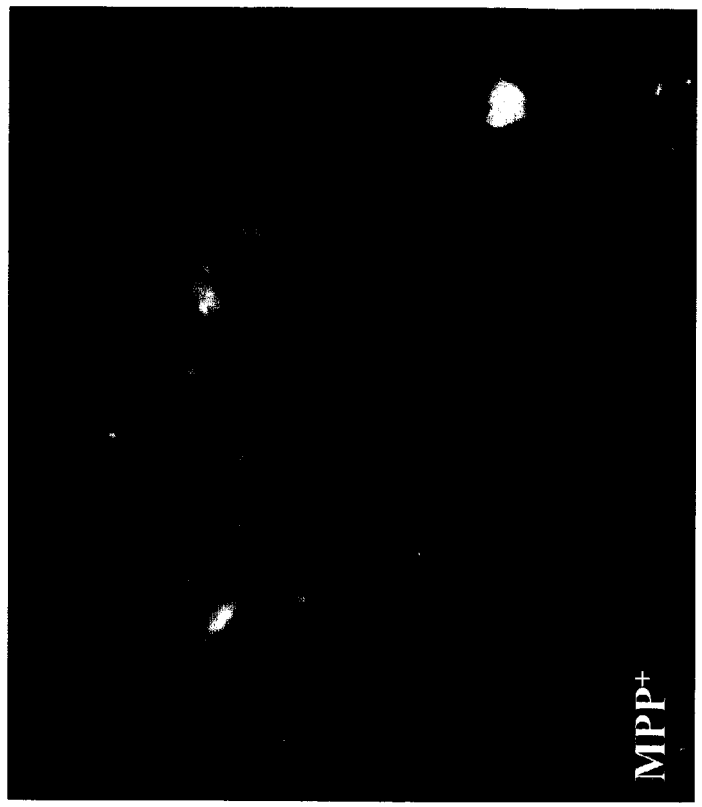
FIGS. 21A and 21B show mitochondrial membrane potentials of RCSN-3 cells.
Figure 21A:
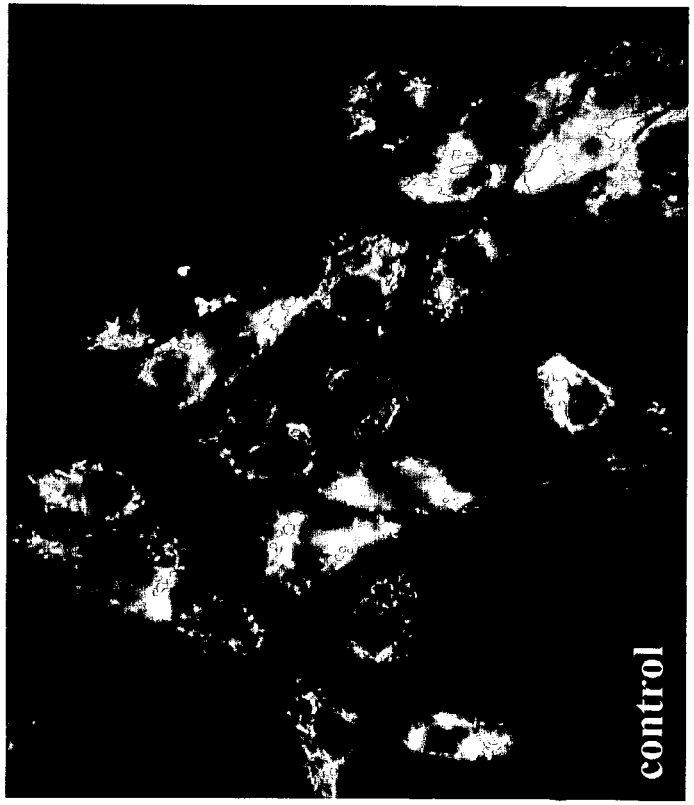
Figure 23:
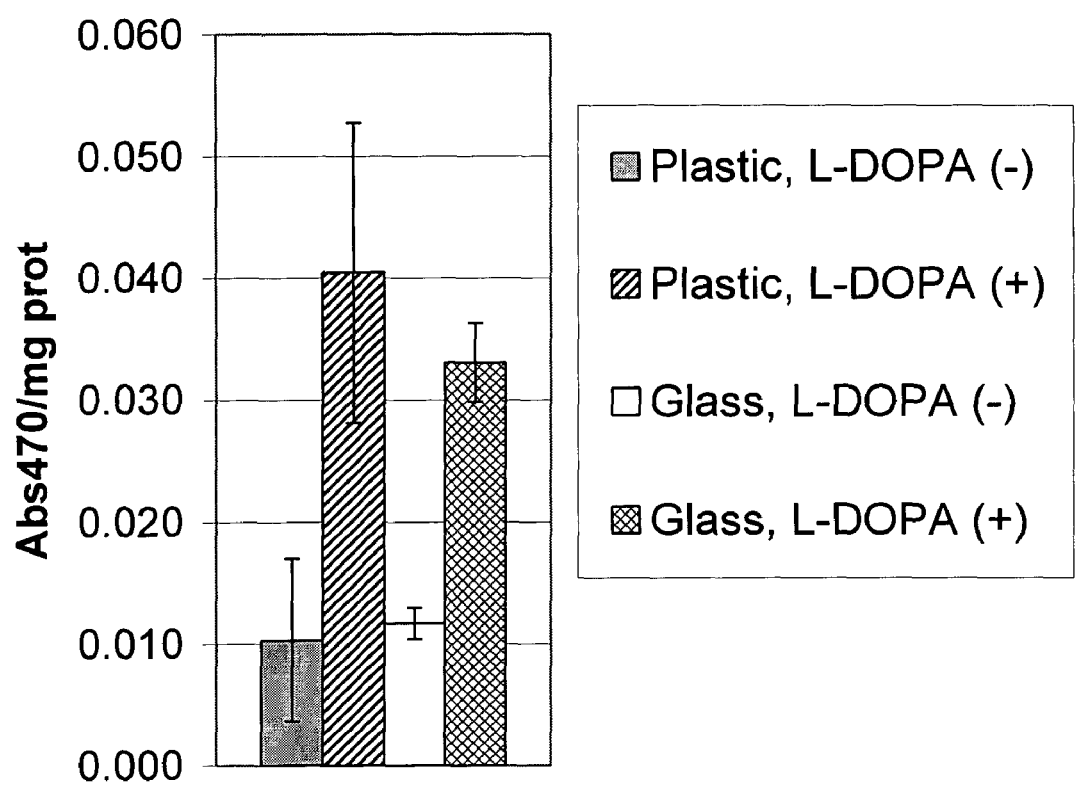
FIG. 23 shows the results of melanin experiments conducted on RCSN-3 cells in the presence or absence of levodopa (L-Dopa).
Figure 24:
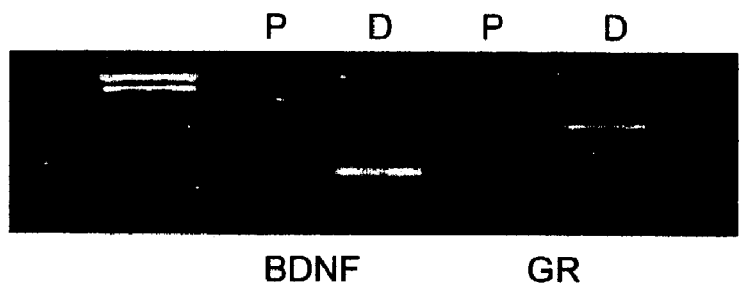
FIG. 24 shows SDS-PAGE demonstrating expression of brain-derived neurotrophic factor (BDNF) and the glucocorticoid receptor (GR) in cells of the H1b cell line (normal fetal mouse hippocampal cells with neuronal phenotype), which were previously cultured in UCHT1 conditioned medium, and were either proliferating (P) or differentiated (D).

FIGS. 19A and 19B show DNA fragmentation studies (TUNEL) in the RCSN-3 cell line cultured in control conditions (FIG. 19A) and after treatment with MPP+ (FIG. 19B). Note the fragmentation of DNA in MPP+ treated cells, indicating an apoptotic mechanism is involved. FIGS. 20A–20C show mitochondrial membrane potential changes with the JC-1 dye. JC-1 is a novel cationic carbocyanine dye that accumulates in mitochondria. The dye exists as a monomer at low concentrations and yields green fluorescence, similar to fluorescein. At higher concentrations, the dye forms J-aggregates that exhibit a broad excitation spectrum and an emission maximum at ~590 nm. These characteristics make JC-1 a sensitive marker for mitochondrial membrane potential (MOLECULAR PROBES, Eugene, Oreg.). The lower flourescence in dopamine and Mn treated cells indicates a decrease in membrane potential, suggesting that mitochondrial dysfunction underlies the effect of these substances. FIGS. 21A and 21B also show JC-1 staining in the presence of MPP+, suggesting that this toxin also affects mitochondrial function. FIGS. 22A and 22B show the ratio of emission between JC-1 and J monomer, normalized according to basal fluorescence. Dopamine, manganese and MPP+ exhibit significant differences from controls.

EXAMPLE 12

Oxidation of Melanin in RCSN-3 Cells

RCSN-3 cells were preincubated for 24 hrs in the presence of 100 microM L-Dopa. Cells were lysed with a hypotonic buffer. Melanin oxidized in situ exhibited a lipofuscin-like yellow fluorescence. Oxidation of melanin in vitro degraded the melanin polymer, resulting in a fluorescent solution. Fluorescence spectroscopy gave an excitation maximum at approximately 470 nm and an emission maximum at approximately 540 nm for both natural and synthetic melanin. Increasing the time of exposure to light or hydrogen peroxide increased melanin fluorescence (Kayatz, P et al., *Invest Ophthalmol Vis Sci, January* 2001,42(1):241–6).

TABLE 3

|  | Average | STD |
|---|---|---|
| Plastic L-DOPA (−) | 0.010 | 0.007 |
| Plastic L-DOPA (+) | 0.040 | 0.012 |
| Glass L-DOPA (−) | 0.012 | 0.001 |
| Glass L-DOPA (+) | 0.033 | 0.003 |

Tables 4 and 5 show a one-way analysis of variance (ANOVA) summary table (Table 9) and a Student's t-Test summary table (Table 10).

TABLE 4

| d | | Group 1 | Group 2 | Group 3 | Group 4 |
|---|---|---|---|---|---|
| | name | Plastic, Control | Plastic, L-DOPA | Glass, Control | Glass, L-DOPA |
| | n | 2 | 3 | 3 | 3 |
| | mean | 0.010334745 | 0.040450776 | 0.011709213 | 0.03305022 |
| | SD | 0.006677779 | 0.012301669 | 0.001290085 | 0.003228081 |

1-way ANOVA
$F = 11.7508$
$p = 0.004021309$
Reject that groups have no differences (thus, at least one pair of groups will reach statistically significant difference)

TABLE 5

Results of Student's T Test

T value of the Student's t-tests for unpaired observations

| P value 2-tailed | Names | Plastic, Control | Plastic, L-DOPA | Glass, Control | Glass, L-DOPA |
|---|---|---|---|---|---|
| | Plastic, Control | | −3.06637 | −0.37672 | −5.32810 |
| | Plastic, L-DOPA | 0.037425 | | 4.02468 | 1.00786 |
| | Glass, Control | 0.725512 | 0.015803 | | −10.63299 |
| | Glass, L-DOPA | 0.005973 | 0.370539 | 0.000443 | |

EXAMPLE 13

Pancreatic Cell Line

A sample of newborn *Cebus* monkey pancreas was obtained and digested enzymatically with collagenase 0.2%. Cells have undergone six passages and most cells express insulin content (80%). Approximately 20% express glucagon. This proportion could be due to selection due to the high content of glucose of our standard DME/HamF12 media (3.15 g/l) used in the UCHT1 protocol. However, the sample was taken from the tail, which has a higher proportion of insulin containing cells. Established from the tail of a pancreas of a newborn *Cebus* monkey. The cell line has undergone 4–5 passages, with over 20 population doublings. The cells look epithelial in morphology. Immunofluorescent studies show over 90% positive reaction for insulin, and less than 5% for glucagon, in culture media with 3.15 g/l glucose. These cultures will continue to be proliferated until immortalization is evident and cultures become independent of UCHT1 media, at which point a full characterization will be carried out.

EXAMPLE 14

Immortalized Neural Cell Lines and Implantation for Treatment of Neurological Disorders Serotonergic cell lines can be derived from the lateral hypothalamus, dorsal raphe nucleus, or hindbrain of embryonic, neonatal, or adult origins. Such cells can be transplanted for the treatment of pain and spinal cord injuries, among other neurologic disorders.

A noradrenergic cell line can also be obtained, derived from the locus ceruleus, the nucleus interstialis striae terminalis, the dorsomedial nucleus, or the raphe nucleus from embryonic, neonatal, or adult donors. Such a cell line can be used for the treatment of epilepsy or memory disorders, for example.

Purkinje cells of the cerebellum can be proliferated from fetal, neonatal, or adult sources for transplantation in cerebellar ataxia disorders, including hereditary or sporadic cerebellar ataxias, familial cerebello-olivary atrophy, ischemia affecting the cerebellum, ataxia-telangiectasia, or immunopathological paraneoplastic degeneration, as well as other forms of ataxia.

Another neuronal cell line of the subject invention includes spinal cord or brain stem motor neurons, which can be proliferated from embryonic, neonatal, or adult sources for transplantation for the treatment of amyotrophic lateral sclerosis or following peripheral nerve injury.

Glial cells from other sites, such as cortical oligodendrocytes, oligodendrocyte progenitor cells, glial neural stem cells, as well as cortical or other glial cells, and peripheral Schwann cells can be proliferated for treatment of multiple sclerosis, peripheral nerve injury, other demyelinating disorders, as well as following head trauma, spinal trauma, hypoxia, ischemic brain disorders/stroke, or optic neuropathy. Such cells can be derived from stem cells, precursor or progenitor cells, or mature cells, from embryonic, neonatal, or adult sources.

Using the methods of the subject invention, striatal, as well as mesencephalic, glial cell lines can be established. Such cell lines will be useful for numerous therapies, including co-grafting with dopamine neurons, co-grafting with striatal neurons, transplantation adjacent, rather than mixed in with, other transplants in order to encourage elongation or branching of neurites, as desired for the particular transplant paradigm. Alternatively, such cell lines can be used as a stand-alone therapy, e.g., to slow or reverse the progression of degenerative disorders affecting the substantia nigra or the striatum, as in Parkinson's disease or Huntington's disease. Such cells are useful for transplantation purposes following a stroke that involves the striatum in other brain regions. Likewise, glial cells can participate in providing trophic support for nigral or striatal neurons, and may ameliorate the neurodegeneration seen in Parkinson's disease or Huntington's disease. These glial cells can be useful in preventing toxin-induced neurodegeneration or neurotoxicity, and provide neuroprotection or rescue of damaged nigral or striatal neurons. These cells or other glial cells can be used in treating demyelinating disorders.

Establishment of a mesencephalic glial cell line can be achieved by obtaining glial cells from the fetal, neonatal, adolescent, or adult substantia nigra (mesencephalon). The striatal cell line includes glial cells derived from the fetal, neonatal, adolescent, or adult striatum. Such cell lines are created by exposing or contacting primary tissue derived from these sites to proliferative factor from the UCHT1 rat thyroid cell line, as previously described. The UCHT1 proliferative factor can be isolated or contained within a composition, such as conditioned medium from the UCHT1 cell line. Human dopamine cell lines derived from the fetal mesencephalon, if used, is preferably dissected from Carnegie Stage 18–23 donors (Freeman T. B. and Kordower J. H., *Human cadaver embryonic substantia nigra grafts: effects of ontogeny, preoperative graft preparation and tissue storage*, in *Intracerebral Transplantation in Movement Disorders: Experimental Basis and Clinical Experience*, 1991, Elsevier Science Publishers, Amsterdam 15:163–169; Freeman T. B. et al., *Exp. Neurol.*, 1991, 113:344–353; Freeman T. B. et al, *Annals of Neurol.*, 1995, 38:379–388). The ontogeny of glial cells also occurs within this window, but these cells also have a broader ontogeny window than the dopamine neurons that develop in a restricted time frame.

Nigral tissue is exposed to the proliferation factor from the UCHT1 rat thyroid cell line, as described above, wherein after about 1–8 months of exposure, cells enter a permanently dividing but differentiated state. Several different cell lines are derived from the mesencephalon, including dopaminergic cell lines as well as glial cell lines. Immunohistochemical markers of neuronal differentiation, such as tyrosine hydroxylase, and glial differentiation, such as GFAP, will be used. Furthermore, in vitro tissue culture methods are utilized to demonstrate that such a cell line induces neuritic outgrowth in dopamine neurons in vitro for the step in characterization, among others.

A striatal glial cell line can be established using fetal, neonatal, adolescent, or adult striatal tissue dissected using known methods (Freeman T. B. et al., *Cell Transplant*, 1995, 4:539–545; Freeman T. B. et al., *Human fetal tissue transplantation for the treatment of movement disorders*, in *Neurosurgical Treatment of Movement Disorders*, AANS Publications, New York, N.Y., pages 177–192; Freeman T. B. and Borlongan C. V., *Soc. Neurosci. Abst.*, 2000, 26:209.6; Freeman, T. B. et al., *Proc. Nt. Acad. Sci.*, 2000, 97:13877–13882). Similar tissue culture methods for the creation of the cell line and characterization of the glial component can be performed. It is anticipated that GABAergic, cholinergic, and other cell types found within the striatum would be found within the culture, and such cell lines can also be characterized immunohistochemically, in vitro, and following transplantation, as above.

Another aspect of the invention is directed to a method for producing a cell line useful for transplantation purposes in patients with Parkinson's disease, comprising the steps of dissecting cells from the human neonatal, adolescent, or adult substantia nigra or the human fetal mesencephalon at Carnegie Stages 18–23. During these stages of development, dopamine neurons develop in the embryonic nigra, and grafts from this stage survive transplantation, form neuritic extensions, and connect to the rodent and human brain, inducing behavioral and clinical benefit, respectively. Success of the use of this donor age has been demonstrated clinically (Freeman, T B et al. *Ann. Neurol.*, 1995, 38:379–388), as well as at autopsy, where grafts were found to survive 18 months after transplantation (Kordower, J H et al., *N England J Med*, 1995, 332:1118–1124; Kordower, J H et al., *J Comp Neurol*, 1996, 370:203–230; Kordower, J H et al., *Cell Transplant*, 1997, 6:213–219).

The nigral tissue or human fetal mesencephalon, which contains 10% dopaminergic nigral neurons, is exposed to the UCHT1 proliferation factor, for example, by exposure to UCHT1 conditioned medium. This procedure has been performed using rodent nigral tissue. The cell lines created in this way differ from cells known prior art in that: (1) The cells are grown in vitro rather than derived directly from a human fetus; (2) the cell line comprises exclusively dopamine neurons of nigral origin; (3) cells are able to be produced using good manufacturing practices in a reproducible and reliable way; (4) the cells can be cryopreserved with preservation of adequate viability in vitro as well as in vivo; and (5) the cells are available electively for surgery.

As mesencephalic dopamine neurons constitute about 10% of the total cells found in the ventral mesencephalon, numerous types of cell lines can be derived from this region, including dopamine neurons from the substantia nigra, which normally project to the striatum; dopamine neurons from the ventral tegmental area, which normally have mesolimbic and frontal projections; as well as mesencaphalic glia and other neuronal types of cells. Dopamine neurons can be classified using tyrosine hydroxylase immunohistochemistry, as well as markers for tyrosine hydroxylase RNA. Specific markers of nigral dopamine neurons, as opposed to those from the ventral tegmental area, may be used, such as aldehyde dehydrogenase immunohistochemistry. In addition, as neuritic outgrowth of nigral grafts is seen within the striatum, as opposed to dopamine neurons from the VTA, where striatal outgrowth is not seen, confirmation of appropriate cell-cell interactions can be tested in vivo with transplantation of specific dopaminergic cell lines in a 6-OHDA rat model, where appropriate neuritic outgrowth within the striatum is expected to be observed (Schultzberg, M. et al., *Neurosci*, 1984, 12:17–32).

Thus, this method, as opposed to other methods known in the art, uses human nigral tissue as the starting tissue, rather than rodent nigral tissue, permitting the creation of an allogenic cell line that can be used clinically without a need for immunosuppression. Also, graft-derived neuritic outgrowth from a human-derived cell line is anticipated to be significantly greater than that from a rodent or porcine cell line.

Another aspect of the invention is a method for creating a GABAergic (gamma-aminobutyric acid-producing) proliferated cell line that is transplantable in multiple patients having Huntington's disease, and also for creating such a cell line for use in other diseases where transplantation of GABAergic cells is useful, such as in the treatment of Parkinson's disease, epilepsy, schizophrenia, spinal cord injury, stroke, or other neurodegenerative diseases (Winkler, C. et al., *Experimental Neurology*, 1999, 155:165–186).

In Parkinson's disease, transplantation of GABAergic neurons into the subthalamic nucleus is beneficial in inhibiting output from this nucleus and ameliorates some symptoms or other movement disorders. In the case of epilepsy, transplants around a seizure focus, or in other regions of the eleptogenic pathway suppress, seizure activity. In the case of schizophrenia, GABAergic inhibition of the ventral tegmental area dopaminergic projections down-regulates the dopamine input to the frontal and mesolimbic cortex and diminishes the symptoms. Following a stroke involving the striatum, striatal transplants can provide clinical benefit, as has been demonstrated in similar animal models.

Stable human GABAergic neuronal lines that retain differentiated properties in continuous culture can be constructed by exposing human neonatal, adolescent, adult, or fetal striatum to the UCHT1 proliferation factor, e.g., via UCHT1 conditioned medium, as taught herein. For example, human adult striatum or far lateral ventricular eminence tissue can be exposed to UCHT1 conditioned medium. Fetal tissue is preferably derived from a human embryo with a donor stage of approximately 7.5–9 weeks post-conception.

After exposure, stable, proliferating differentiated cell lines are derived from the cell types found in the far lateral ventricular eminence. GABAergic and cholinergic cell types, among others found in the developing striatum, can be found within the different clones in the culture. Cell lines of each type of neuronal phenotype found can be created. Cells can be characterized using immunohistochemical methods known in the art. Two different striatal GABAergic cell lines can be created, one that co-labels with CCK and one that co-labels with enkaphalin (ENK), representing two different classes of GABAergic projection neurons found in the striatum (Freeman, T. B. et al. *Proc. Nat. Acad. Sci.*, 2000, 97:13877–13882).

Following the creation of the cell lines, the transformed cells can be characterized immunohistochemically and transplanted into a Huntington's disease model in rats. If successful, such a cell line is then used clinically for transplantation purposes, and may be mixed with other striatal cell types, such as cholinergic interneurons or striatal glia, among others. Such a cell line can also be used to explore the therapeutic benefit in models of Parkinson's disease, epilepsy, spinal cord injury, stroke, and schizophrenia.

Another aspect of the invention includes methods for producing a cell line of striatal cholinergic interneurons for co-transplantation purposes with a similar GABAergic cell line. Here human neonatal, adolescent, or adult striatal neurons, or human fetal cells derived from the medial ventricular eminence (Carnegie Stages 18–23) or the far lateral ventricular eminence (Carnegie Stages 23–29) after migration of cholinergic progenitors to this region occur, are exposed to the UCHT1 proliferation factor, as taught herein. It has been demonstrated that the UCHT1 conditioned medium, for example, can transform primary parenchymal cultures into a substantially permanently dividing differentiated cell line. Such a human cell line is able to be transplanted without the need for lifelong immunosuppression, since the transplant represents an allograft, from the immunologic perspective.

Another aspect of the invention involves the amelioration of memory disorders associated with loss of cholinergic input in the human brain by transplantation of cholinergic neurons. Such neurons can be supplied from cell lines derived from either the nucleus basalis or the septum/diagonal band pathway as being the most likely to provide appropriate reinnervation of the brain in memory disorders.

Cholinergic neurons derived from the human septum and nucleus basalis can be dissected from neonatal, adolescent, or adult brains or a human embryo using known techniques. As previously discussed, the tissue is exposed to the UCHT1 proliferation factor, and the cell line created for transplantation purposes. The cells can be characterized using immunohistochemical markers of cholinergic neurons, including cholinacetyl transferase and acytyl cholinacetyl transferase, among others.

EXAMPLE 15

Sertoli Cell Lines and Other Cells Providing Immunoprivilege

Sertoli cells can also be proliferated using the methods of the subject invention. Sertoli cells can be dissected from any of a variety of mammals (e.g., rodent, pig, human). Preferably, the Sertoli cells are dissected from the testicles in the prepubescent stage of the donor. During this stage, Sertoli cells provide maximum trophic support, as well as expression of Fas-L, for example. Non-proliferated Sertoli cells have been found to survive, provide neurotrophic effects on the brain, neurotrophic support of co-grafts, as well as provide local immunoprotection for neural xenografts via Fas-L or other mechanisms, as well as systemic allo- and xenografts (Sanberg, P. R. et al., *Transplant. Proc.*, 1997, 29:1926–1928;

Willing, A. E. et al., *Brain Res.*, 1999, 246–250; Willing, A. E. et al., *Brain Res. Bull.*, 1999, 48(4):441–444); Kin, T. et al., *Cell Transplantation*, 2002, 11:547–552).

As previously described with respect to all cells, Sertoli cells can be exposed to the UCHT1 cell line's proliferation factor (e.g., by culturing in UCHT1 conditioned medium) for a duration of about 1 to about 8 months, until cells are transformed into a continuously dividing but differentiated state. Thus, Sertoli cells can be proliferated, using the methods of the subject invention, for their FasL expression and co-transplanted to produce local immunosuppression without the need for systemic immunosuppression.

Sertoli cells proliferated using the methods of the subject invention have several advantages, including: (1) the cells are able to be proliferated in vitro, allowing for a generation of adequate quantities of Sertoli cells for a variety of uses (e.g., manufacture of biomolecules, therapeutic implantation, and biological response models), as the availability of donor Sertoli cells is normally limited; (2) a human Sertoli cell line can facilitate xenograft or allograft co-graft survival, minimizing antigenic stimulation of the recipient; (3) the cell line can consist exclusively of Sertoli cells, and therefore could not be contaminated by other mesenchymal cells that may contaminate fresh batches of Sertoli cells; and (4) the cell line can be manufactured using good manufacturing practices and cells can be stored using cryopreservation for use electively.

Furthermore, ovarian stromal cells can be utilized in the subject invention to provide the same benefits as Sertoli cells (e.g., immunosuppressive or trophic properties). For example, cografting of islet cells with placental tissue can normalize blood glucose in diabetic mice (Suzuki, K. et al., *Cell Transplantation*, 2002, 11:45–457), thus preventing rejection in a similar fashion to Sertoli cells. Therefore, proliferation of placental tissue and ovarian stromal cells can be carried out according to the methods of the subject invention. Cells can be genetically modified to express genes encoding apoptotic products, such as those produced by Sertoli cells, ovarian stromal cells, and placental cells.

Lumbar disc material is relatively immune-privileged due to minimal blood supply found in the disc, as well as expression of Fas ligand. Therefore, disc material can be proliferated using the methods of the subject invention and administered to patients with degenerative disc disease with or without immunosuppression, or with short-term immunosuppression. Proliferated disc cells can be transplanted following discectomy or trauma involving the disc. The cells can be administered via an open procedure or percutaneously under radiologic control (i.e., fluoroscopy), for example.

EXAMPLE 16

Purification and Characterization of UCHT1 Proliferation Factor

The UCHT1 proliferation factor that causes immortalization of cell lines has been partially characterized. The proliferation factor, a putative glycoprotein, differs from the many transforming growth factors (TGFs) derived from conditioned media of normal and neoplastic cells, in that known TGFs induce a proliferating effect which is reversible upon removal of the conditioned media; the effect of the UCHT1 proliferation factor is long lasting, even after the medium is withdrawn. Studies in laboratory animals clearly demonstrate the influence of thyroid hormones on induction and growth of several types of experimental tumors (i.e., lymphoma, mammary tumors, primary and transplanted hepatomas). Triiodothyronine plays a role in neoplastic transformation of cultured cells by X rays, chemical carcinogens, and DNA and RNA viruses. The fact that the cellular counterpart of a viral oncogene (v-erbA) encodes a thyroid hormone receptor suggests that this hormone has either a direct or indirect effect on tumor growth. Nevertheless, the presence of the hormone by itself seems insufficient to induce transformation since no cell transformation or tumor promotion has been documented in response to the sole effect of the hormone, and therefore the simultaneous presence of known and unknown growth factors is required.

As described herein, the UCHT1 cell line has been shown to release one or more factors (e.g., in culture media) that are capable of inducing proliferation and later immortalization in primary cell cultures, with preservation of hystotypic and functional properties. Conditioned media derived from cell lines established by the UCHT1 conditioned media (e.g., RCMH, RCVC, and UCHCC1), and other clonal cell lines (e.g., NIH3T3, PTK2, MDCK and KFR) do not show proliferating or transforming activities when added to primary cultures.

Figure 26:
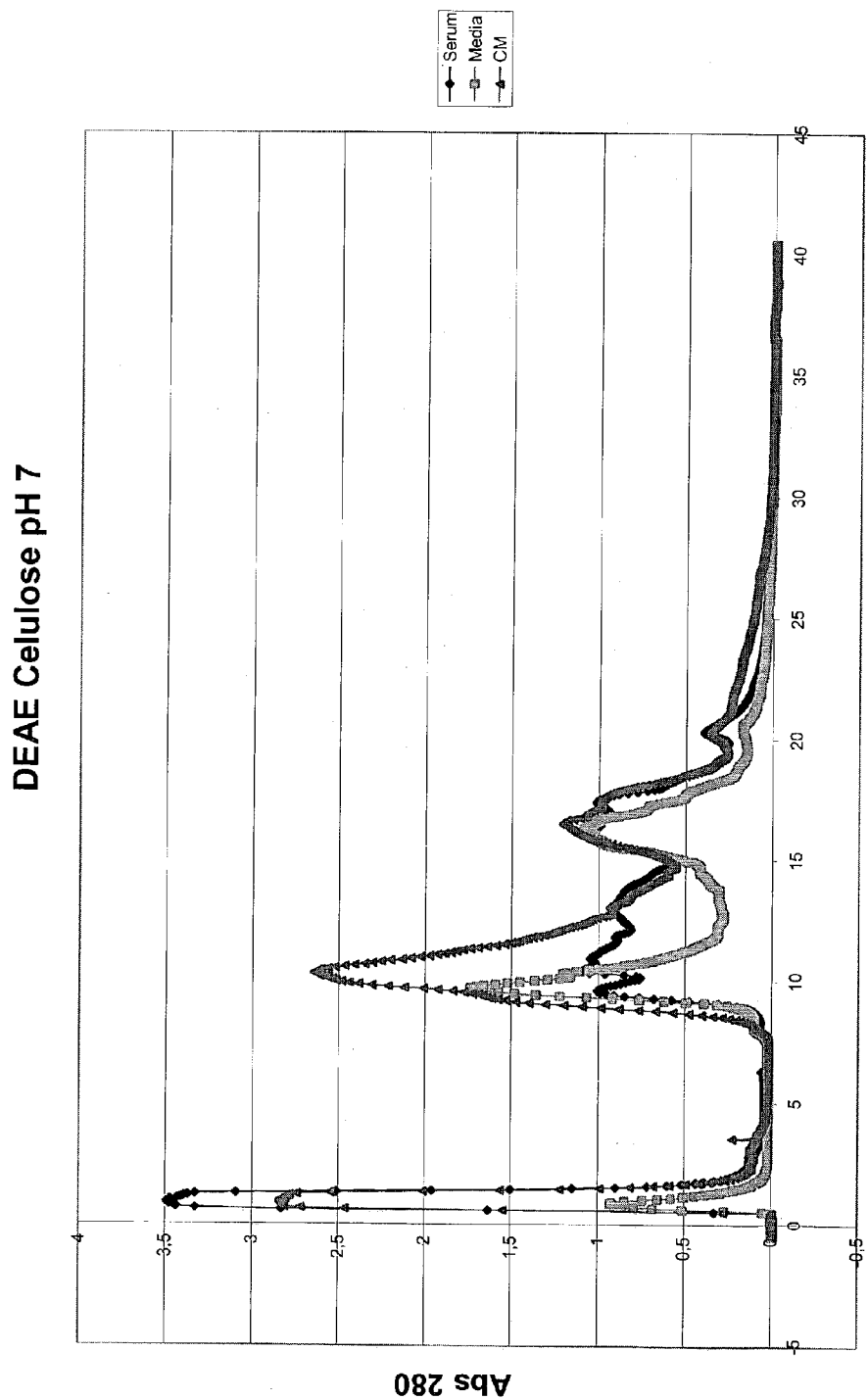
FIG. 26 shows curves associated with samples in ionic exchange chromatography. Although scales are not comparable, the sensitivity of the method is determined by the major components. The curve of serum and culture media may have slight differences due to the presence of amino acids and salts in the basal media. Greater differences between conditioned media and culture media would suggest the presence of secreted proteins. However, after correcting for actual protein content, no significant differences were found to justify a direct comparative analysis.
Figure 27:
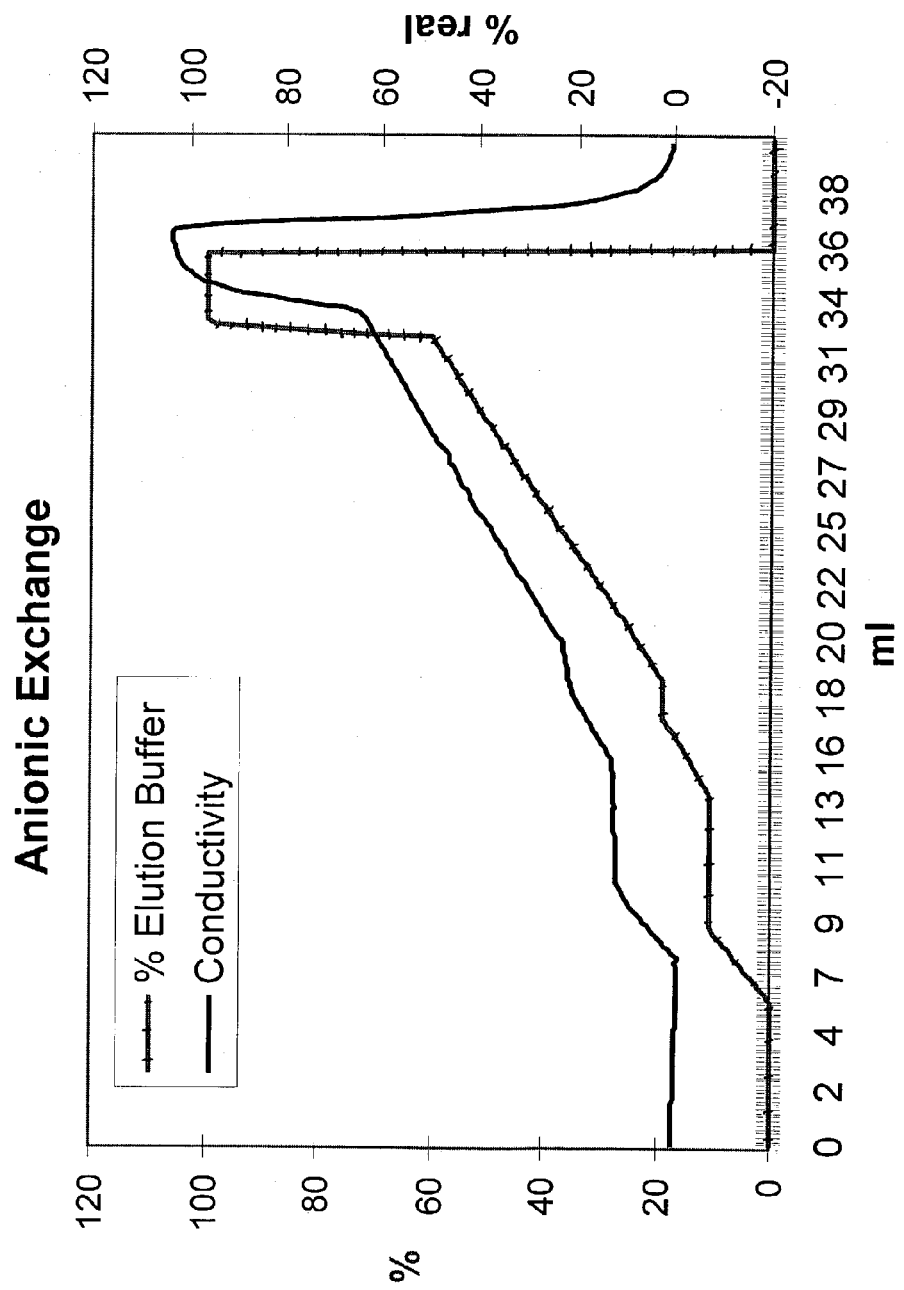
FIG. 27 shows anionic exchange chromatography (DEAE cellulose). Buffer solutions are Bis-Tris 20 mM pH 7 for balance and binding, and Bis-Tris 20 mM pH 7 1M NaCl for elution, considering 20 volumes of column. When compared to FIG. 26, the patterns for transferrin and bovine serum albumin (BSA) are clearly identifiable in fractions 10 and 13–22, respectively. A break exists in the peak for BSA, related to the maintenance of a 20% gradient of the molarity of the salt.
Figure 28:
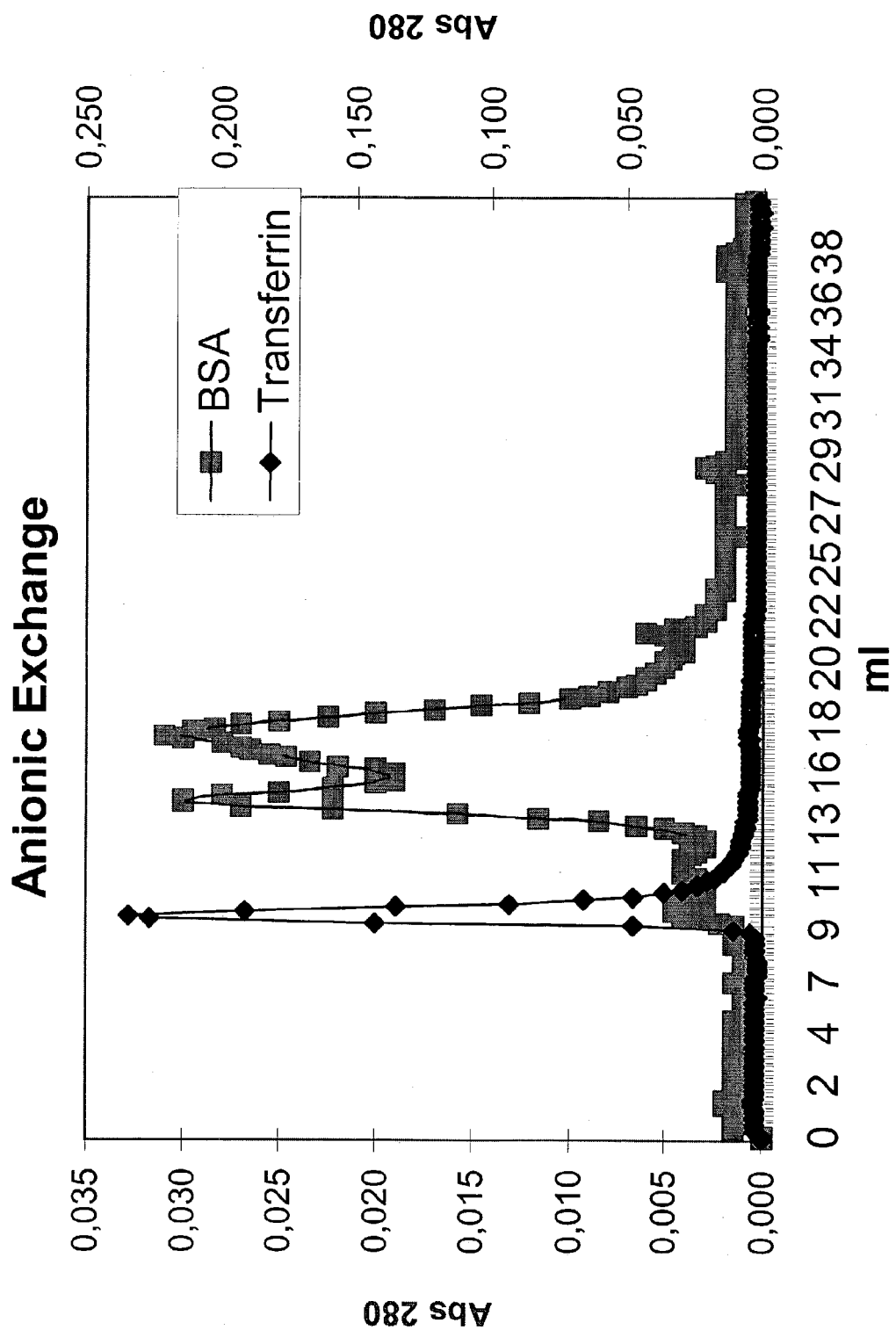
FIG. 28 shows anionic exchange chromatography (DEAE cellulose). The resolution between pure albumin and transferrin is 1.7, which is less than that seen for conditioned media (as shown in FIG. 26), where a resolution of 0.89 for equivalent peaks can be seen. Ideally, resolution levels should be 1.5 or more.
Figure 29:
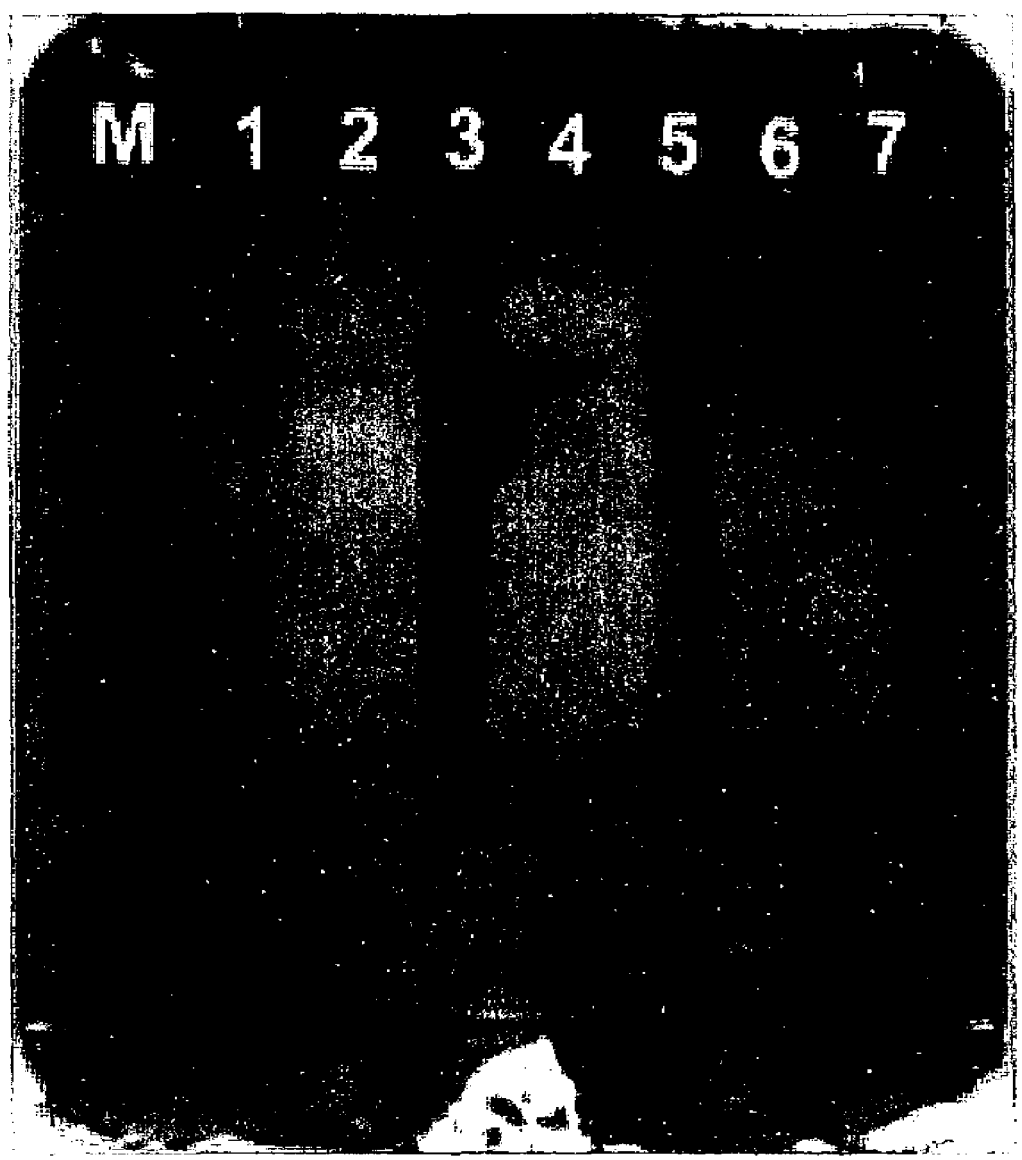
FIG. 29 shows an isolectric focusing gel (IEF) of DEAE-cellulose chromatographic fractions of conditioned media. Albumin predominates in the indicated fractions, but the effect is attenuated in the extremities of the peak, although not enough to allow an adequate resolution of the remaining proteins.
Figure 30:
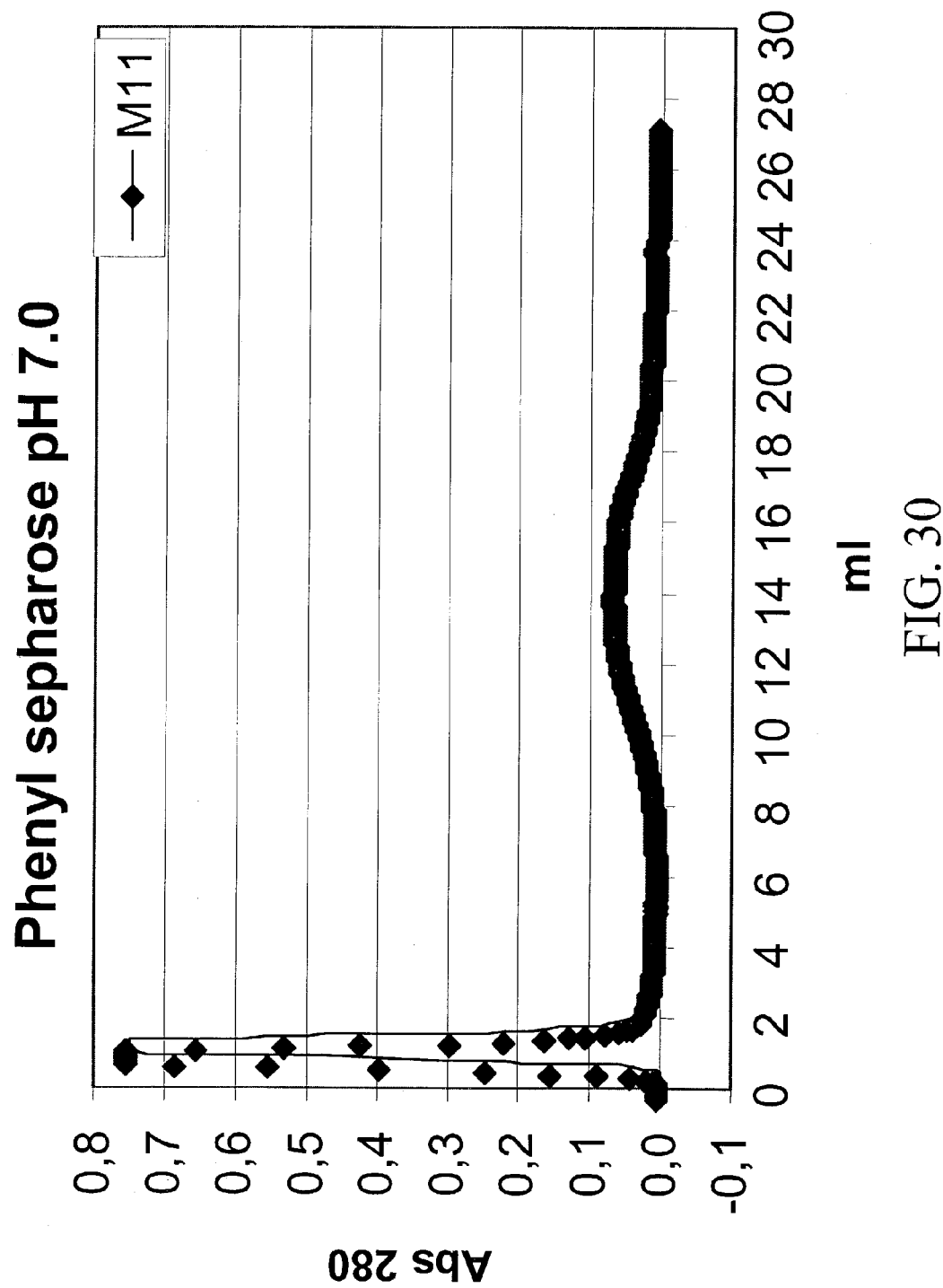
FIG. 30 shows hydrophobic interaction chromatography, presenting the visible peak for the scale associated to the concentrations for the main contaminants. These peaks are readily identifiable after comparing the chromatographic profile in a similar study done in with pure albumin and transferrin (FIG. 31). Correspondence is not identical, possibly due to non-specific hydrophobic interactions associated with the mixture of media proteins. Resolution is superior to 2.
Figure 31:
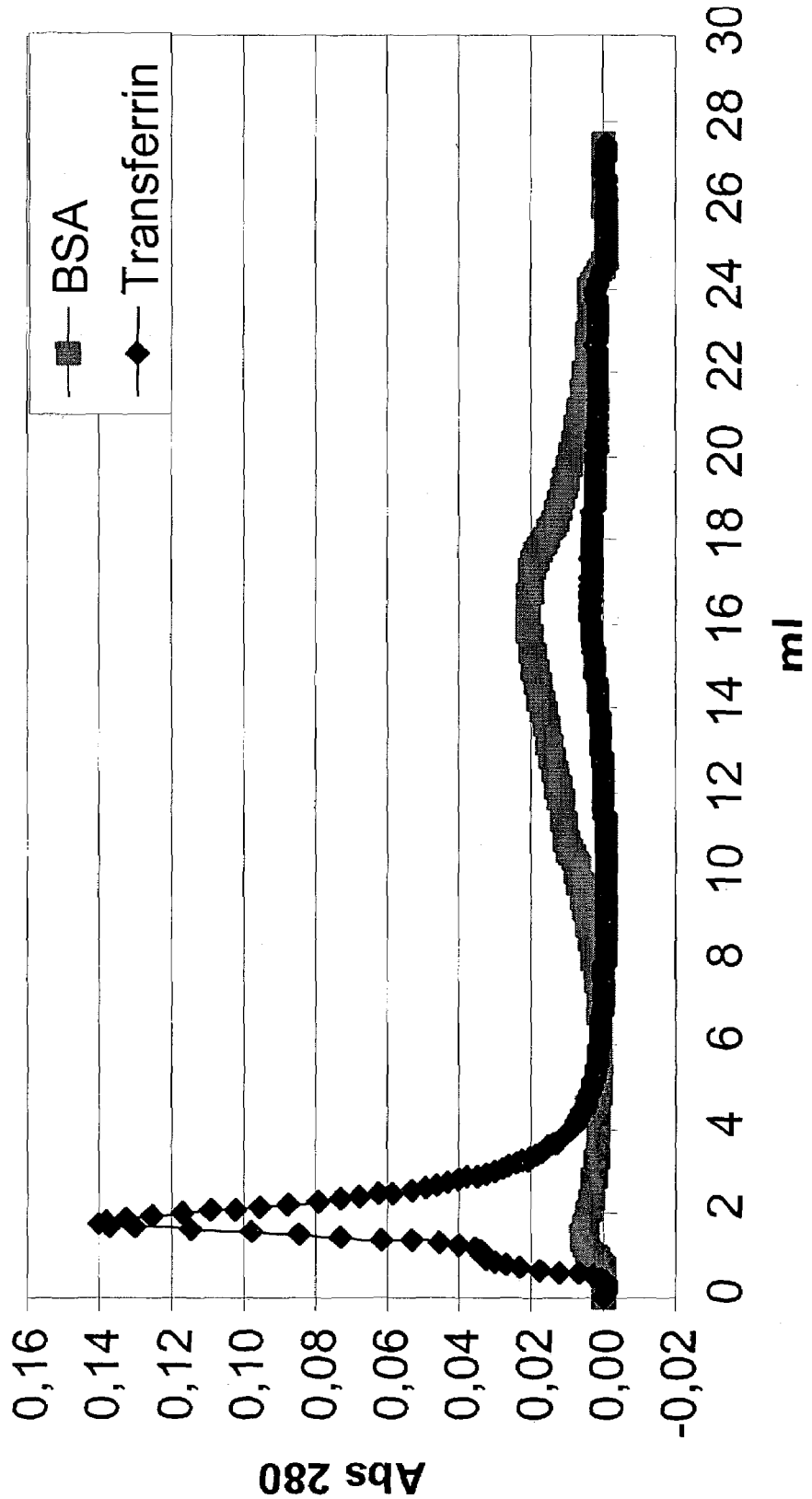
FIG. 31 shows hydrophobic interaction chromatography for pure albumin and transferrin. Resolution is superior to 1.9.
Figure 32A:
FIGS. 32A–32D show the results of bioassays using the KGFR cell line. HSS and conditioned media exert a proliferating effect, although no significant differences are apparent among them. The pro-proliferative effect is evident in FIG. 32B.
Figure 32B:
Figure 32C:
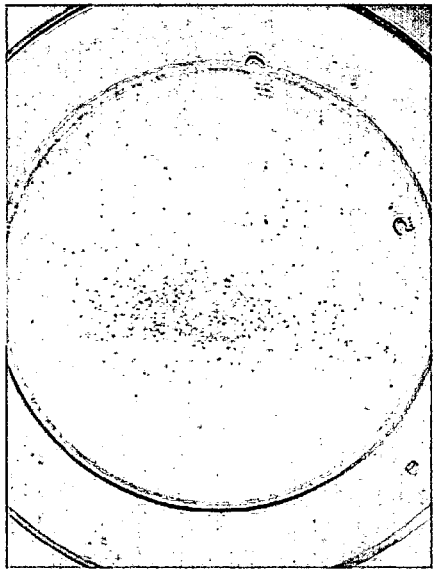
Figure 32D:
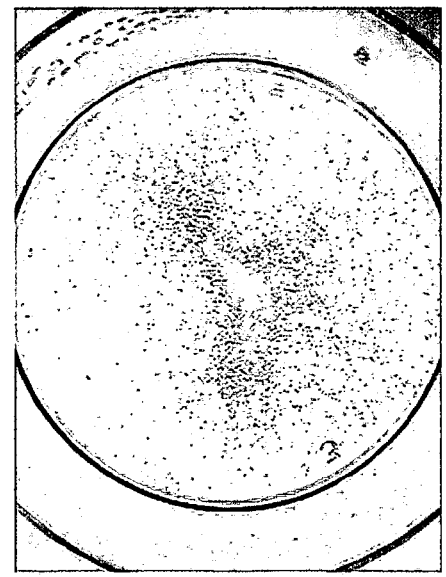
Figure 33:
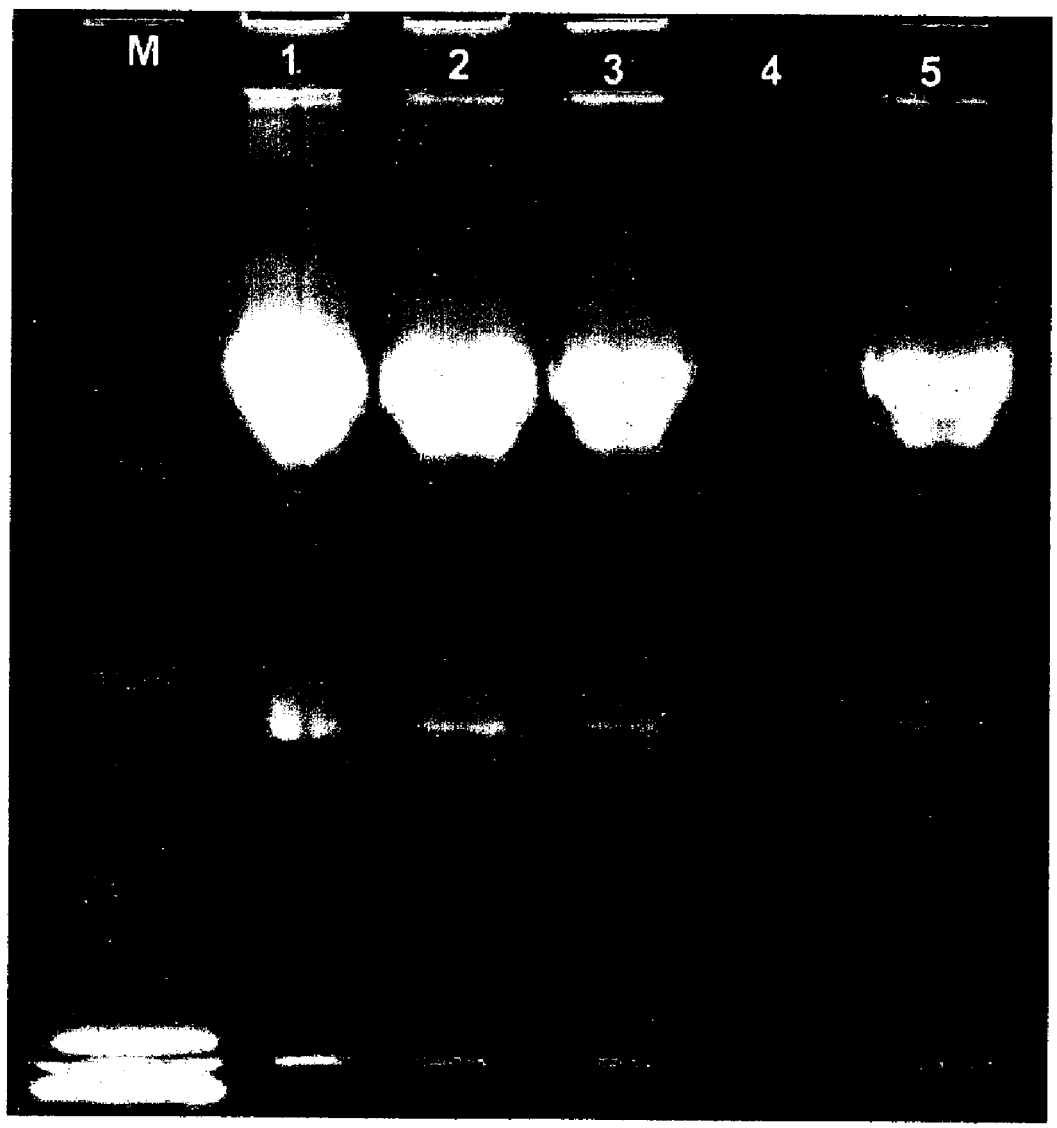
FIG. 33 shows a control SDS-PAGE dyed with Coomassie blue to determine possible protein loss during the pretreatment of the conditioned media. The results show that the loss due to desalinization is negligible.

Crude UCHT1 conditioned media, ultra-centrifuged at high supernatant speed (HSS) at 100,000 rpm for 3 hours, and filtered through 0.2 μm cellulose acetate membranes, stimulate cell proliferation and DNA synthesis in several human, canine, murine, and rat primary cultures and cell lines. In primary cultures of a dysgenic human neuroblastoma and embryonic brain of C57Bl fetal mice, the appearance of transformation foci in periods of 20 to 30 days was detected, which evidenced chromosomal abnormalities. The same UCHT1-conditioned media HSS preparation, when ultra-filtered in CENTRICON (AMICON) molecular filter membranes, at cut levels of 10, 20, and 100 kD, the pro-proliferating activity was recovered in the 30–100 kD range. The fraction proved very stable (thermoresistant; resistant to trypsin). Precipitation of the soluble, 0.2 μm filtered, UCHT1-conditioned media HSS preparation, with acetone 25%, 40%, 50%, 60%, and 80%, shows that the fraction of 40% retained the greatest proliferation inducing activity, using KGFR cells growing in serum free conditions (FIGS. 25 and 32A–D). Differences with culture media and animal sera are present when using ionic exchange chromatography (FIG. 26), where UCHT1 media exhibits a larger peak at approximately 11 ml, suggesting the presence of secreted protein. Anionic chromatography gives values of resolutions for pure albumin and transferrin of 1.7, which is less than that seen for UCHT1 conditioned media (FIGS. 27 and 28), suggesting the presence of proteins other than these two. Further, ioselectric focusing gels indicate albumin predominates as a protein in conditioned media, the attenuation in the extremities of the peak suggest the presence of other protein, but the resolution is insufficient to discriminate them (FIG. 29). Hydrophobic interaction chromatography of conditioned media gives a pattern similar to the combination of transferrin and albumin, with slight differences in correspondence, which could be due to non-specific protein interactions (FIGS. 30 and 31).

Figure 25:
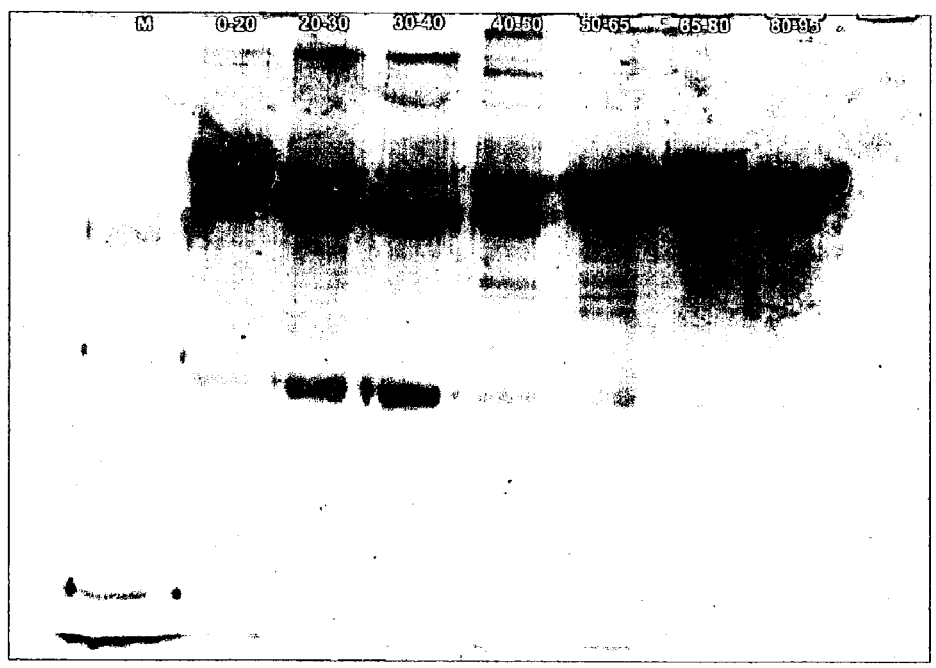
FIG. 25 shows SDS-PAGE dyed with Coomassie blue stain at every saturation level in precipitation with ammonium sulfate, as shown in Table 5. The first column contains molecular weight markers.

FIG. 25 shows SDS-PAGE dyed with Coomassie blue stain at every saturation level in precipitation with ammonium sulfate, as shown in Table 7. The first colunm contains molecular weight markers. FIG. 25 shows that the main components are located at approximately 65 kD and 15 kD, which are associated with albumin and lactoalbumin, respectively. Most protein precipitates at 65%–80% of saturation with ammonium sulfate, but there are a greater number of proteins in the range of 40%–50% and 50%–65%. Theoretically, thyroglobulin precipitates at 40%–50%.

TABLE 6

| Line | Culture media | % Fetal serum | % Bovine Serum | Other |
|---|---|---|---|---|
| UCHT-1 | D/F12 | 2.5 | 10.0 | — |
| " | " | 2.0 | — | — |
| " | " | 2.3 | 9.0 | * |
| " | " | 1.9 | 7.5 | * |
| " | " | 1.3 | 5.0 | * |
| " | " | 0.6 | 2.5 | * |
| " | " | 0.3 | 1.0 | * |
| KGFR | D/F12 | 2.5 | 10.0 | — |
| Neuroblastoma | D/F12 | 10.0 | 10.0 | NGF |
| " | " | 7.5 | 10.0 | " |
| NRK 52E | D/F12 | 10.0 | — | — |
| | DMEM | 10.0 | — | — |

Table 6: Summary of cell lines cultured and the respective culture conditions to which they have adapted. * Insulin, Transferrin, Somatostatin, Hydrocortisone, GlyLysElis, and TSH.

TABLE 7

| Sample | Absorbance | Protein [μg/μl] |
|---|---|---|
| 30% | 3.336 | 38.688 |
| 37% | 1.833 | 11.656 |
| 45% | 3.168 | 35.681 |
| 60% | 3.039 | 33.387 |
| 80% | 1.239 | 0.961 |
| Blank | 0.201 | 0.000 |

Table 7: Results of quantitation of protein (BCA method) in different acetone precipitations of UCHT1-CM (shown as %). Values are normalized to the volume of the re-suspended pellet in 1 ml sterile PBS.

TABLE 8

| Protein | mg/ml |
|---|---|
| CM 2% FS | 0.997 |
| HSS 10-2.5% | 0.662 |
| CM 10-2.5% | 6.482 |
| CM 10-2.5% Pellet 30% | 0.035 |
| CM 10-2.5% N/S 30% | 0.013 |
| CM-N/S 80% | 1.536 |
| CM-N/S 60% | 4.231 |
| CM-N/S 50% | 8.195 |
| CM-N/S 40% | 0.108 |
| CM-N/S 25% | 3.411 |

Table 8: Results of protein quantitation by Bradford's method. CM: UCHT1-conditioned media, ES: fetal serum, 10–2.5%: complex media, N/S: no serum. Values of acetone precipitation are normalized to that of the resuspended pellet.

TABLE 9

| Protein | mg/ml |
|---|---|
| Saturation 0%–20% | 0.25 |
| Saturation 20%–30% | 2.11 |
| Saturation 30%–40% | 5.17 |
| Saturation 40%–50% | 3.42 |
| Saturation 50%–65% | 3.73 |
| Saturation 65%–80% | 11.91 |
| Saturation 80%–95% | 3.24 |

Table 9: Protein quantitation by Bradford's method, for desalinization of ammonium sulfate precipitate. Results show a protein dilution 1:4 of the pellet.

EXAMPLE 17

Purification and Characterization of Tumor Cell Line Proliferation Factors

The original supernatant of the tumor cell line culture, together with subfractions thereof, are used to compare their effectiveness in immortalizing some normal cell type. Preferably, the normal cell line is one that becomes rapidly immortalized. Next, the tumor supernatant fraction is size fractionated on gel filtration columns, preferably using HPLC technology. Next, which of the fractions the immortalizing component resides in is determined. Once the proliferation-bearing fraction or fractions are identified, the active fractions are further subfractioned using HPLC, or general laboratory chromatography columns that separate proteins on the basis of charge, hydrophobicity, or adsorption, for example. Both one-dimensional and two-dimensional SDS-PAGE gels are then run to assay the purity of the fractions. If the fractions are not pure, further separation can be conducted on the basis of size, charge, adsorption, etc., until the number of bands that appear on the gels is reduced to the smallest possible number. These fractions are then cut out of the gels.

Once the fractions are purified, any among a battery of tests (particularly bioassays) of the purified fractions can be carried out to evaluate the effects of the fractions on eukaryotic or prokaryotic cells. For example, direct or indirect measurements of cellular proliferation can be utilized, which often involve incorporation of a labeled nucleoside into genomic DNA. Specific examples include tritiated thymidine ($^3$H-dT) and bromodeoxyoridine (BrdN) methods (Waldman et al., *Modern Pathol.*, 1991, 4:718–722; Gratzner, *Science*, 1982, 218:474–475; U.S. Pat. No. 6,461,806). Assays at the genetic level can also be carried out. For example, the Ames test, micronucleus test, comet assay on *Tradescantia* nuclei, or the pink mutation test on *Tradescantia* staminal hairs, can be used. The Ames test (also referred to as the reverse mutation assay) is widely used to evaluate the mutagenic potential of test substances, such as chemicals, formulations, or extracts (Ames, B. et al., *Proc. Natl. Acad. Sci. USA*, 1973, 70:782–786; McCann, J. et al., *Proc. Natl. Acad. Sci. USA*, 1975, 72:979–983; McCann, J. et al., *Proc. Natl. Acad. Sci. USA*, 1975, 72:5135–5139; Mortelmans, K. and E. Zeiger *Mutat. Res.*, 2000, 455:29–60). The micronucleus test is used to screen test substances for clastogenic (chromosome-breaking) and aneugenic (loss of whole chromosome) activity. The test is based on the observation that mitotic cells with chromosome breaks exhibit disturbances in the anaphase distribution of their chromatin. After the telophase, the displaced chromatin can be excluded from the nuclei of the daughter cells and is found in the cytoplasm as a micronuclei (Schmid, W., *Mutation Res.*, 1975, 31:9; Salamone et al., *Mutation Res.*, 1980, 74:347; Salamone, M. F., *Mutation Res.*, 1983, 123:61; U.S. Pat. No. 6,387,618). Scoring of micronuclei can be performed relatively easily and on a variety of cell types, such as lymphocytes, fibroblasts, and exfoliated epithelial cells. As indicated above, tests for genotoxicity using *Tradescantia* can also be used (Ichikawa, S., *Mutat. Res.*, 1992, 270:3–22; Alvarez-Moya, C. et al., *Salud Publica de México*, November-December 2001, 43(6): 1–7). Other applicable assays are disclosed in Ames, A. et al. "An Improved Bacterial Test System for the Detection and Classification of Mutagens and Carcinogens", in Miller, J. ed. *Discovering Molecular Genetics*, Los Angeles: Cold Spring Harbor Laboratory Press, 1996, pp. 367–376; U.S. Pat. No. 6,489,099; U.S. Pat. No. 6,461,806; U.S. Pat. No. 6,010,846; and U.S. Pat. No. 5,910,403).

Preferably, the cell type used in the bioassay(s) would be one that can be immortalized by the proliferation factor in a rapid manner. The cells can then be compared to the wild type starting material. Examples of suitable cell lines for use in the bioassays include, but are not limited to, NIH-3T3, CHO, MDCK, KGFR, PTK2 (having only 14 chromosomes, this cell line is useful for determination of alterations at the genomic level), Indian Muntjac cells (which has six chromosomes), BALB/c-3T3 (immortalized mouse cell line), C3H 10T1/2 (immortalized mouse cell line), RLV (virally infected rat cell line), and SA7 (virally infected rat cell line. In addition, the Syrian Hamster Embryo Cell Transformation Assay can be used (Kerckaert, G. et al., The Second NIEHS Predictive-Toxicology Evaluation Experiment: 30 Chemical Carcinogenicity Bioassays; Environmental Health Perspectives 104, Supp. 5, [October, 1996 ] "Use of the Syrian Hamster Embryo Cell Transformation Assay for Carcinogenicity Prediction of Chemicals Currently Being Tested by the National Toxicology Program in Rodent Bioassays"). The cells can be suspended in a chemically defined medium without protein. Two-dimensional gels are then run against subfractions from both cell types (starting material and treated material). Components that can be examined include, but are not limited to, organelles such as the nucleus, endoplasmic reticulum, plasma membrane, and mitochondria. Fractionation would be performed with ion exchange, hydrophobic, and gel filtration chromatography. Next, certain unique protein fractions from the proliferating cells would be identified. The fraction that appears first would be preferred for the most rapid assay. A mass spectroscopy analysis of the molecular weight of the fastest, uniquely expressed protein (preferably to four significant figures), would identify which protein fragment is present. This protein can then be sequenced or identified from a protein library. The rapid assay would then be to identify the two-dimensional gel protein fraction that first correlates with immortalization.

Once the protein is fully purified, the protein can be compared to a gene library for determination of the nucleic acid sequence encoding the protein. The gene can then be amplified. The cDNA and an operably linked promoter can be inserted into a plasmid for transfection into a suitable host, such as bacteria, to recombinantly produce the protein inducing cell proliferation.

EXAMPLE 18

Target Cells

As described previously, there are over 200 cell types in the human body and the methods of the subject invention are useful in proliferating any of these cell types, therapeutic, manufacturing, or other purposes. Examples of cell types that can be proliferated using methods of the subject invention are listed in the table below. Other examples of cell types that can be proliferated are disclosed herein.

TABLE 10

Examples of Target Cells

Keratinizing Epithelial Cells
keratinocyte of epidermis
basal cell of epidermis
keratinocyte of fingernails and toenails
basal cell of nail bed
hair shaft cells
medullary
cortical

TABLE 10-continued

Examples of Target Cells cuticular
hair-root sheath cells
cuticular
of Huxley's layer
of Henle's layer
external
hair matrix cell
Cells of Wet Stratified Barrier Epithelia
surface epithelial cell of stratified squamous epithelium of cornea tongue, oral cavity, esophagus, anal canal, distal urethra, vagina
basal cell of these epithelia
cell of urinary epithelium
Epithelial Cells Specialized for Exocrine Secretion
cells of salivary gland
mucous cell
serous cell
cell of von Ebner's gland in tongue
cell of mammary gland, secreting milk
cell of lacrimal gland, secreting tears
cell of ceruminous gland of ear, secreting wax
cell of eccrine sweat gland, secreting glycoproteins
cell of eccrine sweat gland, secreting small molecules
cell of apocrine sweat gland
cell of gland of Moll in eyelid
cell of sebaceous gland, secreting lipid-rich sebum
cell of Bowman's gland in nose
cell of Brunner's gland in duodenum, secreting alkaline solution of mucus and enzymes
cell of seminal vesicle, secreting components of seminal fluid, including fructose
cell of prostate gland, secreting other components of seminal fluid
cell of bulbourethral gland, secreting mucus
cell of Bartholin's gland, secreting vaginal lubricant
cell of gland of Littré, secreting mucus
cell of endometrium of uterus, secreting mainly carbohydrates
isolated goblet cell of respiratory and digestive tracts, secreting mucus
mucous cell of lining of stomach
zymogenic cell of gastric gland, secreting pepsinogen
oxyntic cell of gastric gland, secreting HCl
acinar cell of pancreas, secreting digestive enzymes and bicarbonate
Paneth cell of small intestine, secreting lysozyme
type II pneumocyte of lung, secreting surfactant
Clara cell of lung
Cells Specialized for Secretion of Hormones
cells of anterior pituitary, secreting
growth hormone
follicle-stimulating hormone
luteinizing hormone
prolactin
adrenocorticotropic hormone
thyroid-stimulating hormone
cell of intermediate pituitary, secreting melanocyte-stimulating hormone
cells of posterior pituitary, secreting
oxytocin
vasopressin
cells of gut and respiratory tract, secreting
serotonin
endorphin
somatostatin
gastrin
secretin
cholecystokinin
insulin
glucagons
bombesin
cells of thyroid gland, secreting
thyroid hormone
calcitonin
cells of parathyroid gland, secreting
parathyroid hormone
oxyphil cell
cells of adrenal gland, secreting
epinephrine
norepinephrine
steroid hormones
mineralocorticoids
glucocorticoids
cells of gonads, secreting
testosterone
estrogen
progesterone
cells of juxtaglomerular apparatus of kidney
juxtaglomerular cell
macula densa cell
peripolar cell
mesangial cell
Epithelial Absorptive Cells in Gut, Exocrine Glands, and Urogenital Tract
brush border cell of intestine
striated duct cell of exocrine glands
gall bladder epithelial cell
brush border cell of proximal tubule of kidney
distal tubule cell of kidney
nonciliated cell of ductulus efferens
epididymal principal cell
epididymal basal cell
Cells Specialized for Metabolism and Storage
hepatocyte
fat cells (e.g., adipocyte)
white fat
brown fat
lipocyte of liver
Epithelial Cells Serving Primarily a Barrier Function, Lining the Lung, Gut, Exocrine Glands, and Urogenital Tract
type I pneumocyte
pancreatic duct cell
nonstriated duct cell of sweat gland, salivary gland, mammary gland, etc.
parietal cell of kidney glomerulus
podocyte of kidney glomerulus
cell of thin segment of loop of Henle
collecting duct cell
duct cell of seminal vesicle, prostate gland, etc.
Epithelial Cells Lining Closed Internal Body Cavities
vascular endothelial cells of blood vessels and lymphatics (e.g., microvascular cell)
fenestrated
continuous
splenic
synovial cell
serosal cell
squamous cell lining perilymphatic space of ear
cells lining endolymphatic space of ear
squamous cell
columnar cells of endolymphatic sac
with microvilli
without microvilli
"dark" cell
vestibular membrane cell
stria vascularis basal cell
stria vascularis marginal cell
cell of Claudius
cell of Boettcher
choroid plexus cell
squamous cell of pia-arachnoid
cells of ciliary epithelium of eye
pigmented
nonpigmented
corneal "endothelial" cell
Ciliated Cells with Propulsive Function
of respiratory tract
of oviduct and of endometrium of uterus
of rete testis and ductulus efferens
of central nervous system
Cells Specialized for Secretion of Extracellular Matrix
epithelial:
ameloblast
planum semilunatum cell of vestibular apparatus of ear
interdental cell of organ of Corti
nonepithelial:
fibroblasts
pericyte of blood capillary (Rouget cell)
nucleus pulposus cell of intervertebral disc
cementoblast/cementocyte
odontoblast/odontocyte
chondrocytes TABLE 10-continued Examples of Target Cells of hyaline cartilage
of fibrocartilage
of elastic cartilage
osteoblast/osteocyte
osteoprogenitor cell
hyalocyte of vitreous body of eye
stellate cell of perilymphatic space of ear
Contractile Cells
skeletal muscle cells
red
white
intermediate
muscle spindle-nuclear bag
muscle spindle-nuclear chain
satellite cell
heart muscle cells
ordinary
nodal
Purkinje fiber
Cardiac valve tissue
smooth muscle cells
myoepithelial cells:
of iris
of exocrine glands
Cells of Blood and Immune System
red blood cell (erythrocyte)
megakaryocyte
macrophages
monocyte
connective tissue macrophage
Langerhan's cell
osteoclast
dendritic cell
microglial cell
neutrophil
eosinophil
basophil
mast cell
plasma cell
T lymphocyte
helper T cell
suppressor T cell
killer T cell
B lymphocyte
IgM
IgG
IgA
IgE
killer cell
stem cells and committed progenitors for the blood and immune system
Sensory Transducers
photoreceptors
rod
cones
blue sensitive
green sensitive
red sensitive
hearing
inner hair cell of organ of Corti
outer hair cell of organ of Corti
acceleration and gravity
type I hair cell of vestibular apparatus of ear
type II hair cell of vestibular apparatus of ear
taste
type II taste bud cell
smell
olfactory neuron
basal cell of olfactory epithelium
blood pH
carotid body cell
type I
type II
touch
Merkel cell of epidermis
primary sensory neurons specialized for touch
temperature
primary sensory neurons specialized for temperature TABLE 10-continued Examples of Target Cells cold sensitive
heat sensitive
pain
primary sensory neurons specialized for pain
configurations and forces in musculoskeletal system
proprioceptive primary sensory neurons
Autonomic Neurons
cholinergic
adrenergic
peptidergic
Supporting Cells of Sense Organs and of Peripheral Neurons
supporting cells of organ of Corti
inner pillar cell
outer pillar cell
inner phalangeal cell
outer phalangeal cell
border cell
Hensen cell
supporting cell of vestibular apparatus
supporting cell of taste bud
supporting cell of olfactory epithelium
Schwann cell
satellite cell
enteric glial cell
Neurons and Glial Cells of Central Nervous System
neurons
glial cells
astrocyte
oligodendrocyte
Lens Cells
anterior lens epithelial cell
lens fiber
Pigment Cells
melanocyte
retinal pigmented epithelial cell
iris pigment epithelial cell
Germ Cells
oogonium/oocyte
spermatocyte
Spermatogonium
blast cells
fertilized ovum
Nurse Cells
ovarian follicle cell
Sertoli cell
thymus epithelial cell (e.g., reticular cell)
placental cell

The invention claimed is:

1. A UCHT1 rat thyroid cell line, having deposit number DSM ACC2535.

2. A method for proliferating cells, comprising culturing one or more target cells with conditioned medium prepared from the UCHT1 rat thyroid cell line having deposit No. DSM AC2535 for a period of time sufficient to increase the proliferation potential of the one or more target cells.

3. A method for producing a continuous cell line, comprising culturing one or more target cells with conditioned medium prepared from the UCHT1 rat thyroid cell line having deposit No. DSM ACC2535 for a period of time sufficient to increase the proliferation potential of the one or more target cells such that the one or more target cells proliferate indefinitely.

4. The method of claim 3, wherein the period of time is within the range of about 1 month to about 8 months.

5. The method of claim 3, wherein the one or more target cells are mammalian cells.

6. The method of claim 3, wherein the one or more target cells are human cells.

7. The method of claim 3, wherein the one or more target cells produce a biomolecule, and wherein said method further comprises harvesting the biomolecule from the one or more target cells following said culturing.

8. The method of claim 3, wherein the one or more target cells are selected from the group consisting of skeletal muscle cells, neural cells, myocardial cells, hypothalamus cells, atrial cardiocytes, corneal endothelial cells, and pancreatic cells.

9. A method for determining the effect of an agent on one or more cells, comprising culturing one or more cells with conditioned medium prepared from the UCHT1 rat thyroid cell line having deposit No. DSM ACC2535 for a period of time sufficient to increase the proliferation potential of the one or more cells, exposing the one or more cells to an agent to be tested, and determining the effect of the agent on the one or more cells.

10. The method of claim 9, wherein said exposing comprises contacting the one or more cells to the agent to be tested.

* * * * *

UNITED STATES PATENT AND TRADEMARK OFFICE
CERTIFICATE OF CORRECTION

| | | |
|---|---|---|
| PATENT NO. | : 7,416,885 B2 | |
| APPLICATION NO. | : 10/359854 | |
| DATED | : August 26, 2008 | |
| INVENTOR(S) | : Thomas B. Freeman, Pablo Caviedes and Raúl Caviedes | |

It is certified that error appears in the above-identified patent and that said Letters Patent is hereby corrected as shown below:

Column 9,
Line 33, "isolectric" should read --isoelectric--.

Column 11,
Line 58, "hydrosylates" should read --hydrolysates--.

Column 35,
Line 14, "nueroblastoma" should read --neuroblastoma--.

Column 36,
Line 49, "gentamicyn" should read --gentamycin--.

Column 37,
Line 63, "50 mg/i" should read --50 mg/l--.

Column 41,
Line 12, "a actinin" should read --α actinin--.

Column 44,
Line 61, "pathwaye" should read --pathway--.

Column 45,
Line 11, "adhacent to the space left by the veedle tract" should read --adjacent to the space left by the needle tract--.

UNITED STATES PATENT AND TRADEMARK OFFICE
CERTIFICATE OF CORRECTION

PATENT NO. : 7,416,885 B2
APPLICATION NO. : 10/359854
DATED : August 26, 2008
INVENTOR(S) : Thomas B. Freeman, Pablo Caviedes and Raúl Caviedes It is certified that error appears in the above-identified patent and that said Letters Patent is hereby corrected as shown below:

Column 54,
Line 19, "GlyLysElis" should read --GlyLysHis--.
Line 51, "ES: fetal serum" should read --FS: fetal serum--.

Column 60,
Lines 50-51, "deposit No. DSM AC2535" should read --deposit number DSM ACC2535--.

Signed and Sealed this

Twenty-sixth Day of May, 2009

JOHN DOLL
*Acting Director of the United States Patent and Trademark Office*